US007744617B2

(12) United States Patent
Lunsford et al.

(10) Patent No.: US 7,744,617 B2
(45) Date of Patent: **\*Jun. 29, 2010**

(54) METHOD AND INFLATABLE CHAMBER APPARATUS FOR SEPARATING LAYERS OF TISSUE

(75) Inventors: John P. Lunsford, San Carlos, CA (US); Charles Gresl, San Francisco, CA (US); Jeffrey A. Smith, Sunnyvale, CA (US); Daniel T. Wallace, Mountainview, CA (US); Albert K. Chin, Palo Alto, CA (US)

(73) Assignee: Covidien AG, Neuhausen AM Rheinfall (CH)

( * ) Notice: Subject to any disclaimer, the term of this patent is extended or adjusted under 35 U.S.C. 154(b) by 952 days.

This patent is subject to a terminal disclaimer.

(21) Appl. No.: 10/392,465

(22) Filed: Mar. 19, 2003

(65) Prior Publication Data
US 2003/0236544 A1 Dec. 25, 2003

Related U.S. Application Data

(63) Continuation of application No. 09/023,134, filed on Feb. 12, 1998, now abandoned, which is a continuation of application No. 08/583,563, filed on Jan. 5, 1996, now Pat. No. 5,779,728, which is a continuation-in-part of application No. 08/542,666, filed on Oct. 13, 1995, now Pat. No. 5,728,119, which is a continuation-in-part of application No. 08/405,284, filed on Mar. 16, 1995, now Pat. No. 5,632,761, which is a continuation-in-part of application No. 08/365,096, filed on Dec. 28, 1994, now abandoned, which is a continuation-in-part of application No. 08/319,552, filed on Oct. 7, 1994, now abandoned, which is a continuation-in-part of application No. 08/282,287, filed on Jul. 29, 1994, now Pat. No. 5,704,372, which is a continuation-in-part of application No. 07/911,714, filed on Jul. 10, 1992, now abandoned, which is a continuation-in-part of application No. 07/794,590, filed on Nov. 19, 1991, now Pat. No. 5,309,896, which is a continuation-in-part of application No. 07/706,781, filed on May 29, 1991, now abandoned.

(51) Int. Cl.
*A61B 17/00* (2006.01)
*A61M 29/02* (2006.01)

(52) U.S. Cl. .................. 606/190; 600/184; 600/207; 604/96.01; 606/191; 606/195

(58) Field of Classification Search ......... 606/190–200; 600/115, 116, 184, 207; 604/96.01, 101.01, 604/101.02, 101.05
See application file for complete search history.

(56) References Cited

U.S. PATENT DOCUMENTS 1,060,350 A 4/1913 Miller (Continued)

FOREIGN PATENT DOCUMENTS

AU B-516114 5/1981

(Continued)

OTHER PUBLICATIONS

Ed. G. Berci, ENDOSCOPY, Appleton-Century-Crofts, 1976, pp. 382-385 and 412.

(Continued)

*Primary Examiner*—Anhtuan T Nguyen
*Assistant Examiner*—Kathleen Sonnett

(57) ABSTRACT

An apparatus for tissue dissection and instrument anchoring and methods for using such apparatus are disclosed. The apparatus includes a cannula, a dissection balloon releasably attached to the cannula at the distal end, an anchoring balloon disposed on the cannula, and a means for inflating both balloons.

18 Claims, 36 Drawing Sheets

U.S. PATENT DOCUMENTS

| | | | |
|---|---|---|---|
| 1,275,520 A | 8/1918 | Bell | |
| 1,947,649 A | 2/1934 | Kadavy | |
| 2,663,020 A | 12/1953 | Cushman | |
| 3,039,468 A | 6/1962 | Price | |
| 3,168,092 A * | 2/1965 | Daniel Silverman | 600/7 |
| 3,626,949 A | 12/1971 | Shute | |
| 3,774,596 A | 11/1973 | Cook | |
| 3,782,370 A | 1/1974 | McDonald | |
| 3,831,587 A | 8/1974 | Boyd | |
| 3,863,639 A | 2/1975 | Kleaveland | |
| 3,882,852 A | 5/1975 | Sinnreich | |
| 3,961,632 A | 6/1976 | Moossun | |
| 4,077,412 A | 3/1978 | Moossun | |
| 4,083,369 A | 4/1978 | Sinnreich | |
| 4,137,906 A | 2/1979 | Akiyama et al. | |
| 4,183,102 A | 1/1980 | Guiset | |
| 4,240,433 A | 12/1980 | Bordow | |
| 4,254,762 A | 3/1981 | Yoon | |
| 4,271,839 A | 6/1981 | Fogarty et al. | |
| 4,291,687 A | 9/1981 | Sinnreich | |
| 4,318,410 A | 3/1982 | Chin | |
| 4,357,940 A | 11/1982 | Muller | |
| 4,364,392 A * | 12/1982 | Strother et al. | 606/195 |
| 4,430,076 A | 2/1984 | Harris | |
| 4,447,227 A | 5/1984 | Kotsanis | |
| 4,493,711 A | 1/1985 | Chin et al. | |
| 4,535,773 A | 8/1985 | Yoon | |
| 4,589,410 A * | 5/1986 | Miller | 128/207.15 |
| 4,598,699 A | 7/1986 | Garren et al. | |
| 4,601,710 A | 7/1986 | Moll | |
| 4,630,609 A * | 12/1986 | Chin | 606/194 |
| 4,651,717 A | 3/1987 | Jakubczak | |
| 4,654,030 A | 3/1987 | Moll et al. | |
| 4,661,095 A | 4/1987 | Taller et al. | |
| 4,685,447 A | 8/1987 | Iversen et al. | |
| 4,709,697 A | 12/1987 | Muller | |
| 4,744,363 A | 5/1988 | Hasson | |
| 4,775,371 A | 10/1988 | Muller, Jr. | |
| 4,779,611 A | 10/1988 | Grooters et al. | |
| 4,784,133 A * | 11/1988 | Mackin | 606/7 |
| 4,800,901 A | 1/1989 | Rosenberg | |
| 4,863,440 A | 9/1989 | Chin | |
| 4,913,701 A | 4/1990 | Tower | |
| 4,919,152 A | 4/1990 | Ger | |
| 4,944,443 A | 7/1990 | Oddsen et al. | |
| 4,966,583 A | 10/1990 | Debbas | |
| 4,984,564 A | 1/1991 | Yuen | |
| 5,002,557 A | 3/1991 | Hasson | |
| 5,007,898 A | 4/1991 | Rosenbluth et al. | |
| 5,029,574 A | 7/1991 | Shimamura et al. | |
| 5,082,005 A | 1/1992 | Kaldany | |
| 5,083,576 A | 1/1992 | Ruiz-Razura et al. | |
| 5,122,122 A | 6/1992 | Allgood | |
| 5,122,155 A | 6/1992 | Eberback | |
| 5,137,512 A | 8/1992 | Burns et al. | |
| 5,141,515 A | 8/1992 | Eberbach | |
| 5,147,316 A | 9/1992 | Castillenti | |
| 5,163,949 A | 11/1992 | Bonutti | |
| 5,176,128 A | 1/1993 | Andrese | |
| 5,176,687 A * | 1/1993 | Hasson et al. | 606/114 |
| 5,176,692 A | 1/1993 | Wilk et al. | |
| 5,176,697 A | 1/1993 | Hasson et al. | |
| 5,183,463 A | 2/1993 | Debbas | |
| 5,183,464 A | 2/1993 | Dubrul et al. | |
| 5,188,630 A * | 2/1993 | Christoudias | 606/1 |
| 5,195,507 A | 3/1993 | Bilweis | |
| 5,195,972 A | 3/1993 | Inoue | |
| 5,197,948 A | 3/1993 | Ghodsian | |
| 5,197,971 A | 3/1993 | Bonuitti | |
| 5,269,753 A | 12/1993 | Wilk | |
| 5,295,994 A | 3/1994 | Bonutti | |
| 5,308,327 A | 5/1994 | Heaven et al. | |
| 5,309,896 A | 5/1994 | Moll et al. | |
| 5,318,586 A | 6/1994 | Ereren | |
| 5,330,497 A | 7/1994 | Freitas et al. | |
| 5,331,975 A | 7/1994 | Bonutti | |
| 5,334,146 A | 8/1994 | Ozasa | |
| 5,354,270 A | 10/1994 | Wilk et al. | |
| 5,359,995 A * | 11/1994 | Sewell, Jr. | 600/204 |
| 5,361,752 A * | 11/1994 | Moll et al. | 600/205 |
| 5,366,442 A | 11/1994 | Wang et al. | |
| 5,419,765 A * | 5/1995 | Weldon et al. | 604/99.02 |
| 5,425,357 A | 6/1995 | Moll et al. | |
| 5,425,760 A | 6/1995 | Rosenberg | |
| 5,445,615 A | 8/1995 | Yoon | |
| 5,468,248 A * | 11/1995 | Chin et al. | 606/192 |
| 5,478,320 A | 12/1995 | Trotta | |
| 5,484,420 A | 1/1996 | Russo | |
| 5,496,345 A | 3/1996 | Kieturakis et al. | |
| 5,514,091 A | 5/1996 | Yoon | |
| 5,514,153 A | 5/1996 | Bonutti | |
| 5,522,790 A | 6/1996 | Moll et al. | |
| 5,540,711 A | 7/1996 | Kieturakis et al. | |
| 5,549,625 A | 8/1996 | Bircoll | |
| 5,575,759 A | 11/1996 | Moll et al. | |
| 5,601,581 A | 2/1997 | Fogarty et al. | |
| 5,601,589 A | 2/1997 | Fogarty et al. | |
| 5,607,441 A | 3/1997 | Sierocuk et al. | |
| 5,607,443 A * | 3/1997 | Kieturakis et al. | 606/192 |
| 5,653,726 A | 8/1997 | Kieturakis | |
| 5,656,013 A | 8/1997 | Yoon | |
| 5,667,479 A | 9/1997 | Kieturakis | |
| 5,681,342 A | 10/1997 | Benchetrit | |
| 5,693,031 A | 12/1997 | Ryan et al. | |
| 5,707,382 A | 1/1998 | Sierocuk et al. | |
| 5,713,869 A | 2/1998 | Morejon | |
| 5,720,762 A | 2/1998 | Bass | |
| 5,725,545 A | 3/1998 | Bircoll | |
| 5,730,748 A | 3/1998 | Fogarty et al. | |
| 5,738,628 A | 4/1998 | Sierocuk | |
| 5,746,762 A | 5/1998 | Bass | |
| 5,762,604 A | 6/1998 | Kieturakis | |
| 5,779,728 A | 7/1998 | Lunsford et al. | |
| 5,782,813 A | 7/1998 | Yoon | |
| 5,797,947 A | 8/1998 | Mollenauer | |
| 5,814,060 A | 9/1998 | Fogarty et al. | |
| 5,823,947 A | 10/1998 | Yoon et al. | |
| 5,865,802 A | 2/1999 | Yoon et al. | |
| 5,868,707 A | 2/1999 | Williams et al. | |
| 5,873,880 A | 2/1999 | Williams et al. | |
| 5,876,376 A | 3/1999 | Schwab et al. | |
| 5,964,730 A | 10/1999 | Williams et al. | |
| 5,972,015 A | 10/1999 | Scribner et al. | |
| 5,984,942 A | 11/1999 | Alden et al. | |
| 6,007,483 A | 12/1999 | Kieturakis | |
| 6,055,989 A | 5/2000 | Rehnke | |
| 6,120,437 A | 9/2000 | Yoon et al. | |
| 6,146,401 A | 11/2000 | Yoon et al. | |
| 6,152,895 A | 11/2000 | Wilk | |
| 6,159,219 A | 12/2000 | Ren | |
| 6,238,376 B1 | 5/2001 | Peterson | |
| 6,264,604 B1 | 7/2001 | Kieturakis et al. | |
| 6,264,670 B1 | 7/2001 | Chin | |
| 6,277,137 B1 | 8/2001 | Chin | |
| 6,361,543 B1 | 3/2002 | Chin et al. | |
| 6,364,892 B1 | 4/2002 | Jervis | |
| 6,364,894 B1 | 4/2002 | Healy et al. | |
| 6,368,337 B1 | 4/2002 | Kieturakis et al. | |
| 6,375,637 B1 | 4/2002 | Campbell et al. | |
| 6,432,121 B1 | 8/2002 | Jervis | |
| 6,451,042 B1 | 9/2002 | Bonutti | |
| 6,471,673 B1 | 10/2002 | Kastenhofer | |
| 6,524,283 B1 * | 2/2003 | Hopper et al. | 604/264 |
| 6,562,056 B2 | 5/2003 | Jervis | |

| | | | |
|---|---|---|---|
| 6,607,534 B2 | 8/2003 | Bonutti | |
| 6,632,234 B2 | 10/2003 | Kieturakis et al. | |
| 6,866,676 B2 | 3/2005 | Kieturakis et al. | |
| 6,953,467 B2 | 10/2005 | Kieturakis et al. | |
| 2004/0015182 A1 | 1/2004 | Kieturakis et al. | |
| 2004/0097792 A1 | 5/2004 | Moll et al. | |

FOREIGN PATENT DOCUMENTS

| | | |
|---|---|---|
| DE | A 2 847 633 | 5/1979 |
| DE | U 91-04-383 | 7/1991 |
| EP | A 0 010 650 | 5/1980 |
| EP | A 0 246 086 | 11/1987 |
| EP | A 0 251 976 | 1/1988 |
| EP | A 0 275 230 | 7/1988 |
| EP | 0 573 273 A2 | 12/1993 |
| FR | 2 474 304 | 7/1981 |
| FR | 2 646 088 | 10/1990 |
| FR | A 2 688 695 | 5/1992 |
| GB | A 2 071 502 | 9/1981 |
| SU | 797 668 | 1/1991 |
| WO | WO83/03188 | 9/1983 |
| WO | WO93/11824 | 12/1992 |
| WO | WO93/09722 | 5/1993 |
| WO | WO93/10850 | 6/1993 |
| WO | WO97/13464 | 4/1997 |
| WO | WO 99/12602 | 3/1999 |

OTHER PUBLICATIONS

Unknown—Laparoscopy for Sterilization, Section 1, A Chronology of Laparoscopy.
"New Surgical Procedures for Indirect Hernias"—Product leaflet for Herniastat™ disposable automatic surgical stapling device published by Innovative Surgical Devices, Inc., date unknown.
"A Tiny TV Camera is Fast Transforming Gallbladder Surgery," Wall Street Journal, Dec. 10, 1990, p. A1, continued on p. A5.
A Comprehensive Guide to Purchasing (Hospital Supplies), V. Mueller & Co., Chicago, 1956, p. 829.
H. Nagai et al., A New Method of Laparoscopic Cholecystectomy: An abdominal Wall Lifting Technique Without Pneumoperitoneum, Surgical Laparoscopy and Endoscopy, vol. 1, No. 2, 1991, p. 126.
M.M. Gazayerli, "The Gazayerli Endoscopic Retractor, Model 1;" Surgical Laparoscopy & Endoscopy, vol. 1 No. 2, pp. 98-100, Raven Press, New York, Jun. 1991.
Geza J. Jako & Stephen Rozsos, "Preliminary Report: Endoscopic Laser Microsurgical Removal of Human Gallbladder," J. Laparoendoscopic Surgery, vol. 1, No. 4, 1991.
European Search Report dated Jul. 15, 2009 for EP 96945432.

* cited by examiner

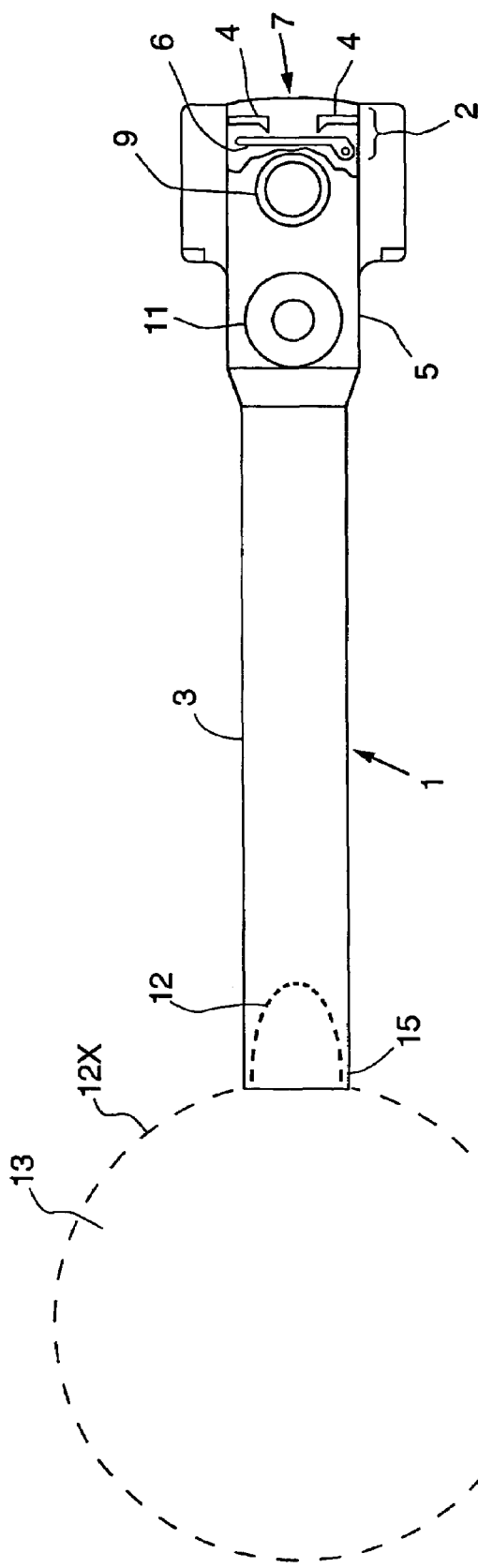
FIG. 1A
FIG. 1B
FIG. 1C

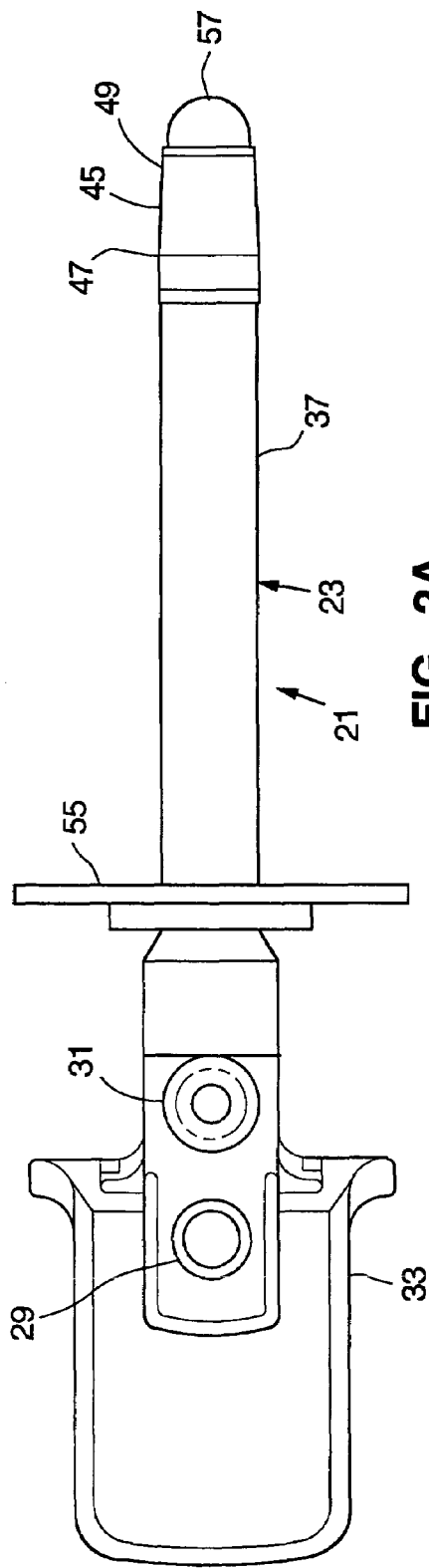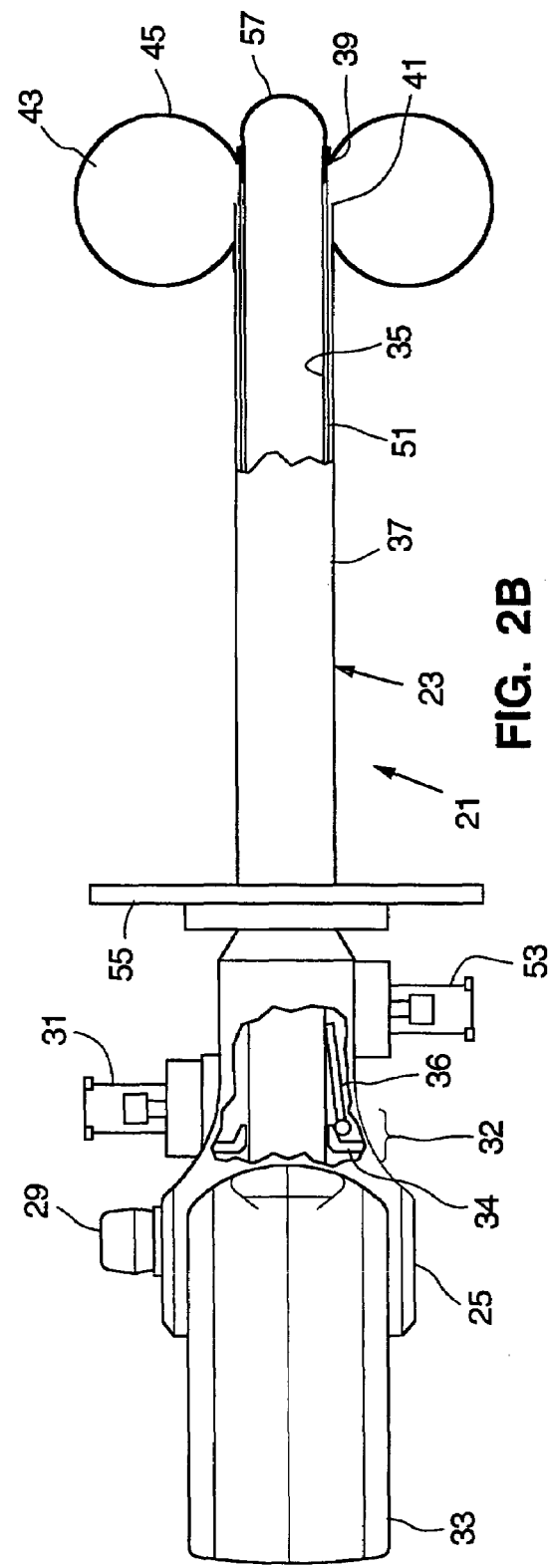

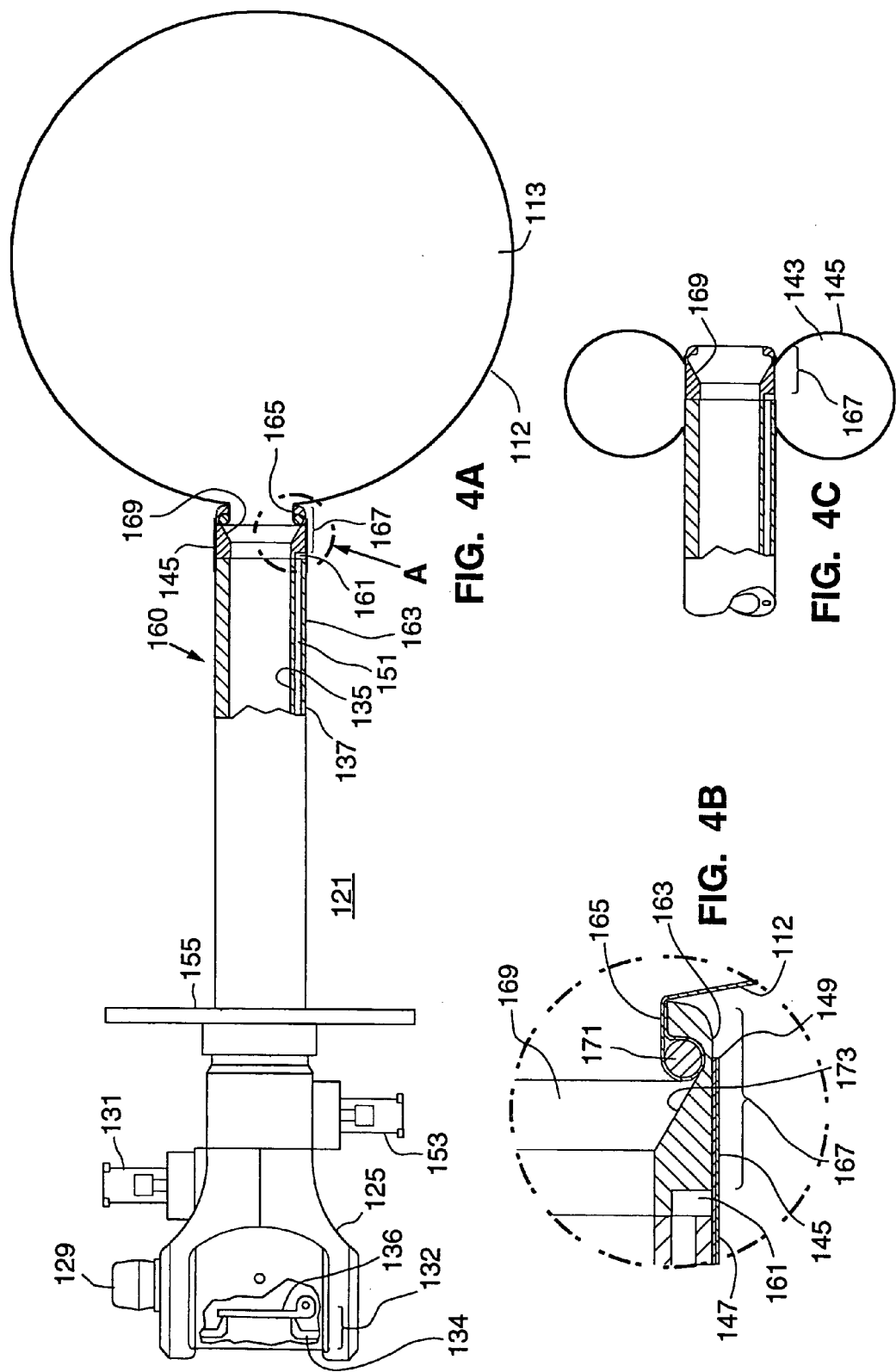

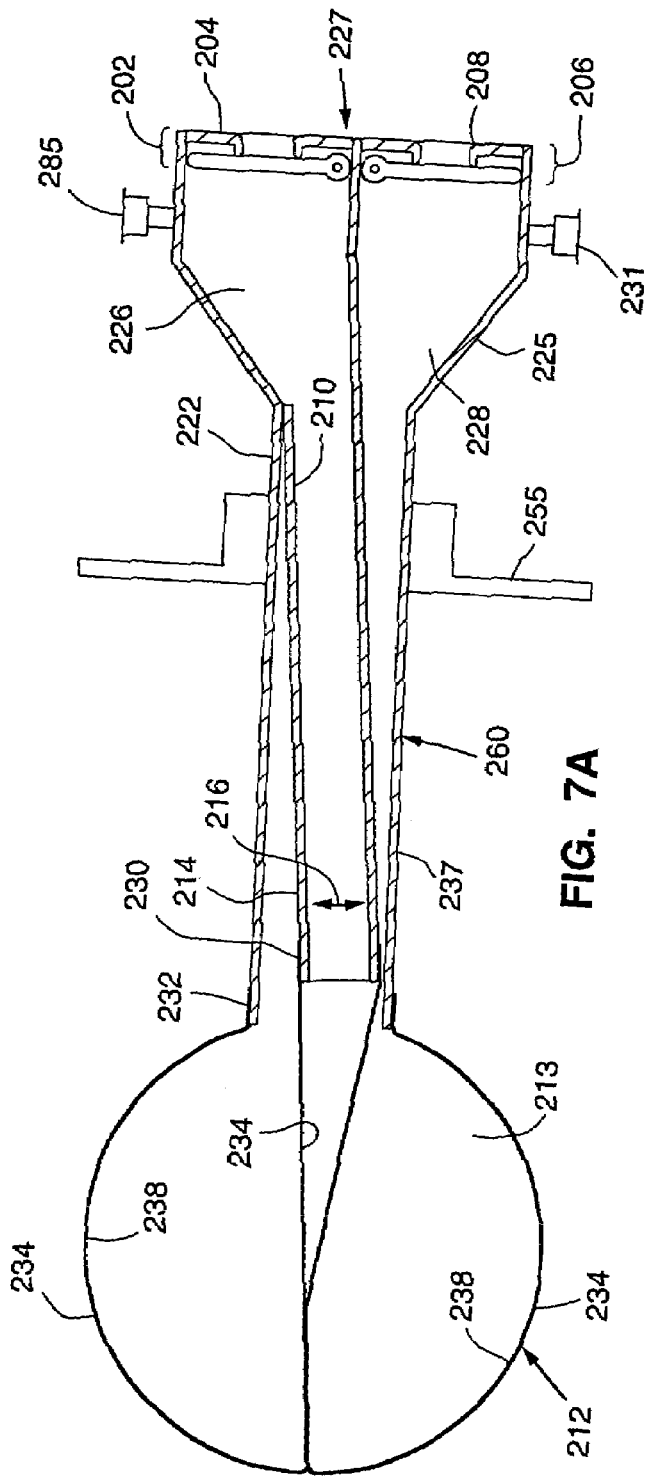
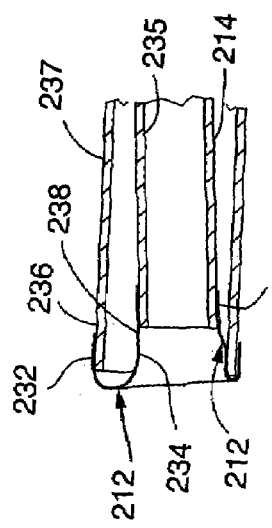
FIG. 7A
FIG. 7B

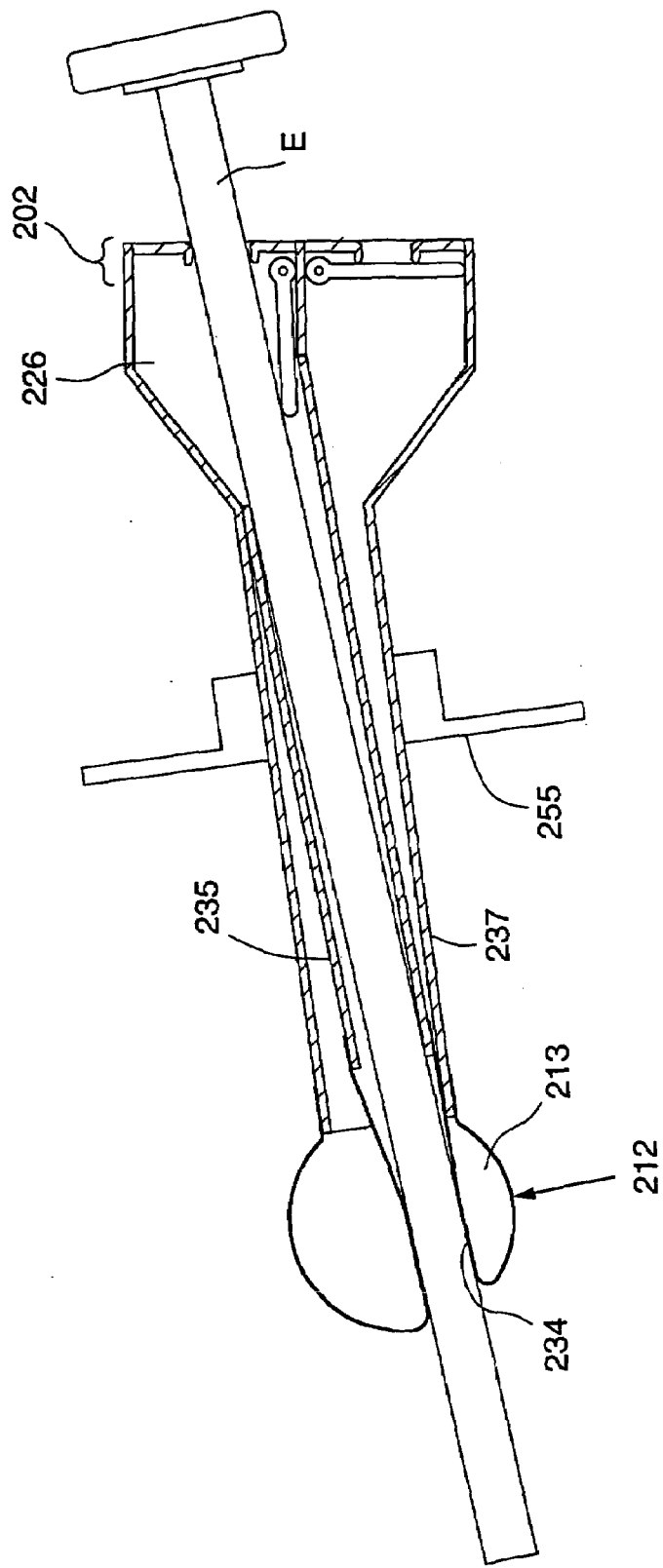

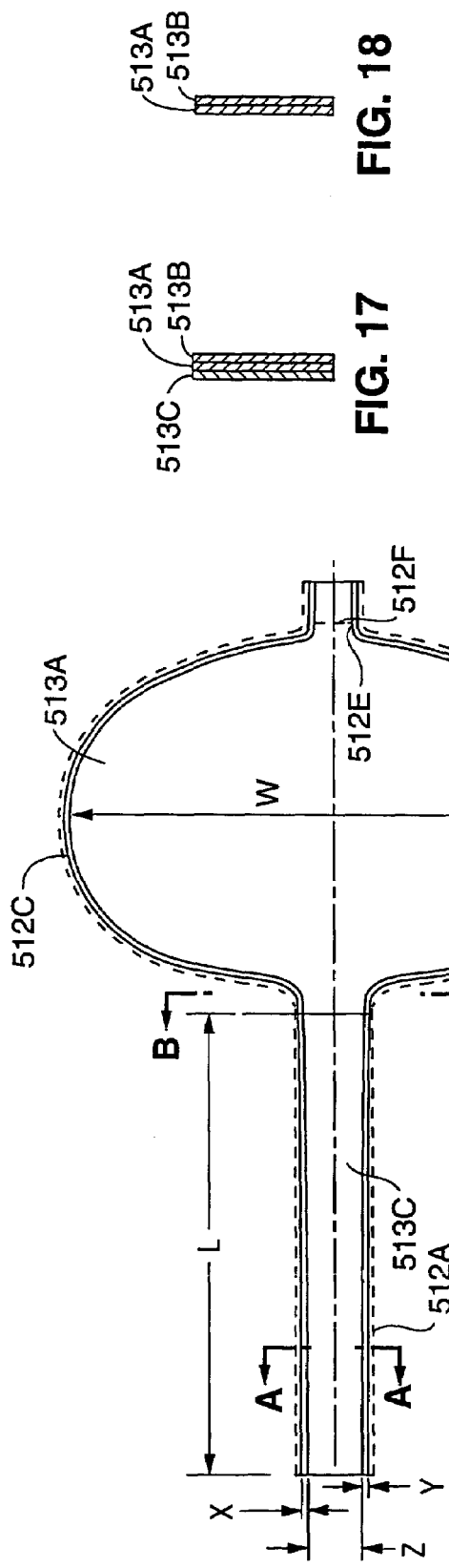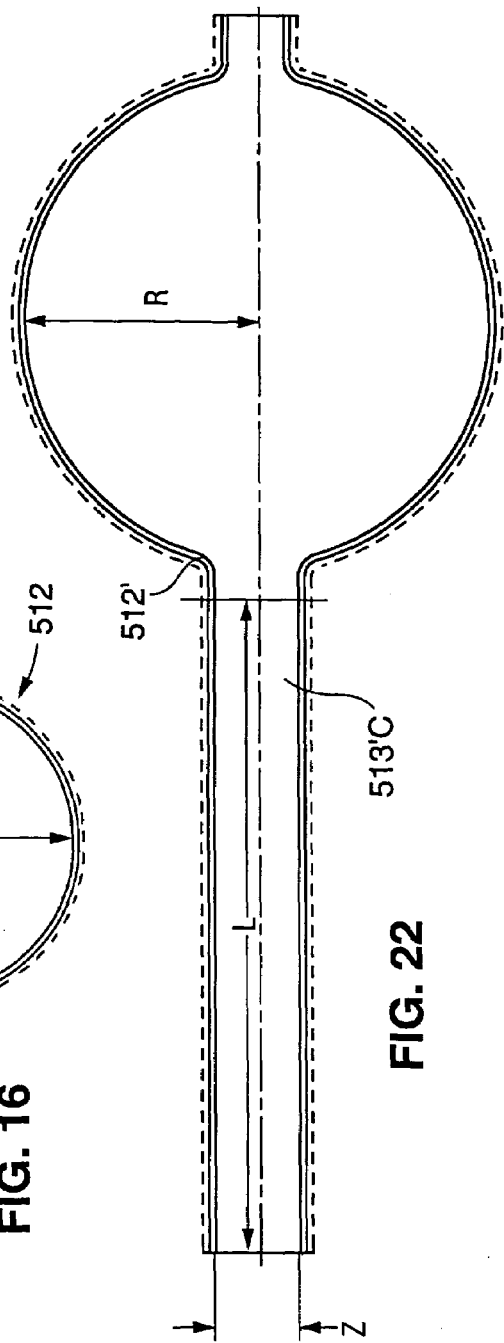

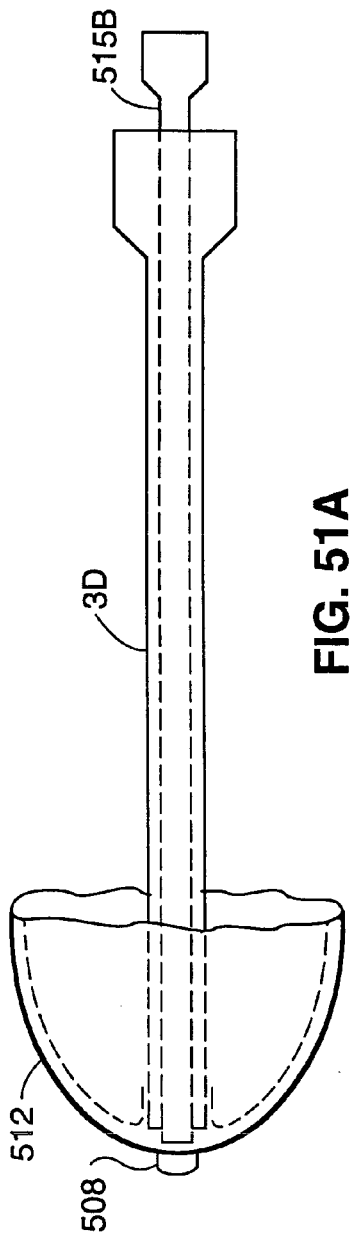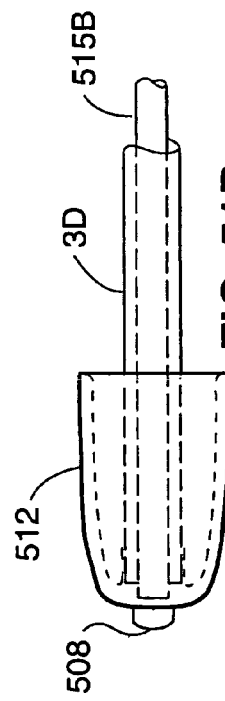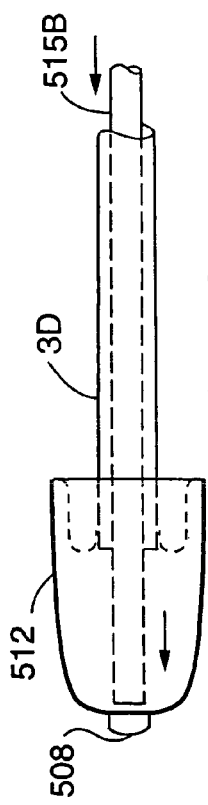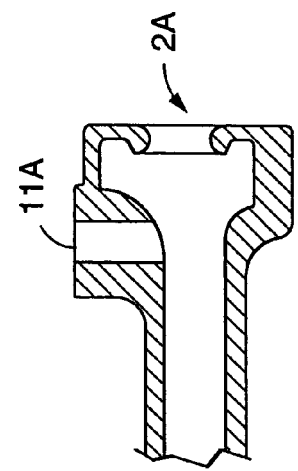

METHOD AND INFLATABLE CHAMBER APPARATUS FOR SEPARATING LAYERS OF TISSUE

This application is a continuation of application Ser. No. 09/023,134, filed Feb. 12, 1998 now abandoned, which is a continuation of application Ser. No. 08/583,563, filed Jan. 5, 1996, now U.S. Pat. No. 5,779,728 which is a continuation-in-part (C.I.P.) of Ser. No. 08/542,666, filed Oct. 13, 1995, now U.S. Pat. No. 5,728,119 of inventors Jeffrey A. Smith, Daniel T. Wallace, Edwin J. Hlavka, Charles Gresl, John P. Lunsford, and Albert K. Chin, which is a C.I.P. of U.S. application Ser. No. 08/405,284, filed Mar. 16, 1995, now U.S. Pat. No. 5,632,761 of inventors Jeffrey A. Smith, Albert K. Chin, and Frederic H. Moll, which is a C.I.P. of Ser. No. 08/365,096, filed Dec. 28, 1994, now abandoned, of inventors Albert K. Chin and Todd Thompson, which is a C.I.P. of Ser. No. 08/319,552, filed Oct. 7, 1994, now abandoned, of inventors Albert K. Chin, Jeffrey A. Smith, John P. Lunsford and Frederic H. Moll, which is a C.I.P. of Ser. No. 08/282,287, filed Jul. 29, 1994, now U.S. Pat. No. 5,704,372 of inventors Frederic H. Moll, Jeffrey A. Smith, John P. Lunsford and Albert K. Chin, which is a C.I.P. of Ser. No. 07/911,714, filed Jul. 10, 1992, now abandoned, of inventors Albert K. Chin and John P. Lunsford, which is a C.I.P. of Ser. No. 07/794,590, filed Nov. 19, 1991, now issued as U.S. Pat. No. 5,309,896, of inventors Frederic H. Moll, Charles Gresl, Jr., Albert K. Chin, and Philip K. Hopper, which is a C.I.P. of Ser. No. 07/706,781, filed May 29, 1991, now abandoned, of inventors Frederic H. Moll, Albert K. Chin, Diane E. Caramore, and Frank T. Watkins II. The specifications of the above-referenced applications, which are commonly owned with present application, are incorporated by reference into the specification of the present application.

FIELD OF THE INVENTION

The invention pertains to inflatable tissue separation and retraction devices and methods of using such devices. The apparatus and methods of the invention are useful in any procedure requiring dissection and/or retraction of tissue planes throughout the body including inguinal hernia repair, pelvic lymphadenectomy and bladder neck suspension in the preperitoneal space; renal, adrenal, aortic and anterior spinal access in the retroperitoneal space; penile prosthetic reservoir placement in the anterior abdominal wall; plastic surgery; and augmentation mammaplasty prosthetic placement. By way of example only, use of such devices and methods for hernia repair will be described.

BACKGROUND OF THE INVENTION

A hernia is the protrusion of part of a body part or structure through a defect in the wall of a surrounding structure. Most commonly, a hernia is the protrusion of part of abdominal contents, including bowel, through a tear or weakness in the abdominal wall, or through the inguinal canal into the scrotum.

An abdominal hernia is repaired by suturing or stapling a mesh patch over the site of the tear or weakness. The mesh patch has a rough surface that can irritate the bowel and cause adhesions. It is therefore preferred to install the patch properitoneally (the terms properitoneal and preperitoneal are used as synonyms). The mesh patch is preferably attached to the properitoneal fascia of the abdominal wall and covered by the peritoneum. To attach the mesh patch to the properitoneal fascia, the peritoneum must be dissected from the properitoneal fascia. This is a difficult process which involves the risk of puncturing the peritoneum. Moreover, strands of properitoneal fat interconnecting the peritoneum and the properitoneal fascia make it difficult to see the site of the hernia.

The abdominal wall includes various layers of tissue. The peritoneum (P) is the innermost layer. Overlying the peritoneum are several layers of tissue, including the properitoneal fat layer (FL) and the properitoneal fascia (F). The properitoneal fascia is the layer to which a mesh patch is preferably attached in hernia repair. The properitoneal fat layer separates the peritoneum from the properitoneal fascia. The properitoneal fat layer is relatively weak, which enables the peritoneum to be separated relatively easily from the fascia.

When the peritoneum is separated from the fascia, separation takes place at or in the properitoneal fat layer. The properitoneal fat layer can remain attached to the properitoneal fascia, or can come away with the peritoneum. Alternatively, part of the properitoneal fat layer can remain attached to the peritoneum and part of the fat layer can come away attached to the peritoneum. Because of the uncertainty in the point of separation, the layer which is detached will be called the peritoneum, and the layer from which the peritoneum is detached will sometimes be denoted as the overlying layer. Additional layers of tissue lie between the properitoneal fascia and the skin.

An inguinal hernia occurs when the contents of the abdominal cavity break through the abdominal wall. As described above, a hernia is repaired by attaching a piece of mesh to the abdominal wall. To prevent the mesh from causing trauma to the bowel, either through irritation of the bowel by the rough surface of the mesh, or by adhesion of the bowel to the mesh, it is preferred to attach the mesh to the properitoneal fascia. With the mesh attached to the fascia, the peritoneum covers the mesh and isolates the bowel from the mesh.

Conventional techniques of attaching the mesh patch to the properitoneal fascia, both laparoscopic and normal, involve blunt dissecting the peritoneum away from the properitoneal fascia, working from inside or outside the belly. The apparatus and methods according to the invention enable the peritoneum to be separated from the properitoneal fascia and the mesh patch attached to the fascia without entering the belly.

Although the following description will describe apparatus and methods according to the invention with respect to hernia repair, the inventive apparatus and methods are not restricted to hernia repair. The apparatus and methods can also be used in other procedures in which one layer of tissue is separated from another to form a working space between the layers. These procedures include thoracoscopy in patients with pleural adhesions; pericardioscopy, or the introduction of an endoscope into the pericardial cavity, in patients with pericardial adhesions; retroperitoneal lymph node dissection, in which the peritoneum on the distal aspect of the abdominal cavity is separated from the underlying tissue which includes lymph nodes; and in separating a blood vessel from surrounding connective tissue in the course of, for example, a femoropopliteal arterial bypass graft procedure.

Laparoscopic techniques to perform hernia repair are being used increasingly frequently. In the conventional procedure for carrying out a hernia repair laparoscopically, an endoscope and instruments are introduced into the belly through one or more incisions in the abdominal wall, and advanced through the belly to the site of the hernia. Then, working from inside the belly, a long incision is made in the peritoneum covering the site of the hernia. Part of the peritoneum is dissected from the properitoneal fat layer to provide access to the fat layer. This is conventionally done by blunt dissection, such as by sweeping a rigid probe under the peritoneum. In this procedure, it is difficult to dissect the peritoneum cleanly since patchy layers of properitoneal fat tend to adhere to the peritoneum.

In an alternative known laparoscopic hernia repair procedure, the belly is insufflated. An incision is made in the abdominal wall close to the site of the hernia. The incision is made through the abdominal wall as far as the properitoneal fat layer. The peritoneum is then blunt dissected from the properitoneal fat layer by passing a finger or a rigid probe through the incision and sweeping the finger or rigid probe under the peritoneum. After the peritoneum is dissected from the properitoneal fat layer, the space between the peritoneum and the properitoneal fat layer is insufflated to provide a working space in which to apply the mesh patch to the properitoneal fascia.

During the blunt dissection process, it is easy to puncture through the peritoneum, which is quite thin. Additionally, after initial dissection of the properitoneal space, known surgical procedures require introduction of various instruments in the space to conduct the surgery. These instruments can cause inadvertent puncture of the peritoneum wall after the initial dissection. A puncture destroys the ability of the space between the peritoneum and the fascia to hold insulation gas; pressurized gas can travel through a puncture in the peritoneum to allow the fluid to migrate to the abdominal cavity and degrade the pressure differential maintaining the properitoneal cavity. Also, it is difficult to dissect the peritoneum cleanly since patchy layers of properitoneal fat tend to adhere to the peritoneum. Clearing difficult adhesions can sometimes result in a breach of the peritoneum itself.

U.S. Pat. No. 5,309,896 (of which this application is a C.I.P.), discloses a laparoscopic hernia repair technique that enables a mesh patch to be attached to the properitoneal fascia without breaching the peritoneum. An incision is made through the abdominal wall as far as the properitoneal fat layer. A multi-chambered inflatable retraction device is pushed through the incision into contact with the peritoneum, and is used to separate the peritoneum from the overlying tissue layer. The main end chamber of the inflatable retraction device is then inflated to elongate the inflatable retraction device towards the site of the hernia. As it inflates, the inflatable retraction device gently separates more of the peritoneum from the overlying tissue layer. Once the main chamber of the inflatable retraction device is fully inflated, a second inflatable chamber is inflated. The second inflatable chamber enables the inflatable retraction device to continue to separate the peritoneum from the other tissue layers after the main inflatable chamber has been deflated.

One or more apertures are then cut in the envelope of the main inflatable chamber to provide access to the site of the hernia for instruments passed into the main chamber. With such an arrangement, instruments pass through the main chamber while the main chamber remains between the peritoneum and the overlying layers. In this way, a patch can be attached to the properitoneal fascia without breaching the peritoneum.

Until the present invention, it had not been known how to view a space between tissue layers while (or after) dissecting the layers with a balloon, without removing any portion of the dissecting apparatus including the balloon, but also without image degradation resulting from viewing through balloon wall. Nor, until the present invention, had it been known to design a balloon (suitable for tissue dissection, tissue retraction, and/or instrument anchoring) to have any of a wide range of inflated shape and pressure characteristics. For example, it had not been known to design a tissue dissection balloon to have inflated shape and pressure characteristics tailored for producing a working space (between dissected tissue layers) having a particular size and shape selected from a broad range of sizes and shapes.

SUMMARY OF THE INVENTION

In a class of embodiments, the invention is an apparatus for tissue dissection and instrument anchoring, which includes a dissection balloon having a viewing window (preferably a rigid, transparent window) at its distal end. The window can but need not be a lens (such as a wide angle lens) having a desired focal length. The window of the dissection balloon is transparent, and either rigid or non-rigid but sufficiently strong to retain a desired optical shape while (and after) being pushed against tissue layers by a rigid obturator (or other rigid instrument) deployed within the balloon. In preferred embodiments, the window is cup-shaped, in the sense that it has a recessed base for receiving and capturing the distal end of a rigid obturator or endoscope.

In preferred embodiments, the balloon is a long-necked balloon deployed through a cannula. The balloon has an open distal end, and a rigid, transparent window (made of polished, clear polycarbonate or acrylic material or the like) is glued over its open distal end. When the distal end of the balloon has been inserted between tissue layers, an endoscope extending through the cannula within the balloon can view the tissue layers through the window (whether or not the balloon is inflated).

In other embodiments, the invention is a dissection balloon having a viewing window at its distal end, for use in an apparatus for tissue dissection, tissue retraction, and instrument anchoring. The window can but need not be a lens (such as a wide angle lens). In other embodiments, the invention is a dissection balloon assembly including a long-necked dissection balloon having a viewing window at its distal end, and a housing to which the dissection balloon's mouth is attached. The housing is shaped for removable attachment to a tissue retraction and instrument anchoring apparatus including a cannula (with the dissection balloon's neck deployed through the cannula and the window extending beyond the cannula's distal end).

In other, simplified, embodiments, the invention is a dissection balloon, useful for separating tissue layers, attached to the distal end of a trocar or obturator. A viewing window which may or may not be a lens (such as a wide angle lens) is provided at the distal end of the dissection balloon. A longitudinal bore in the trocar or endoscope allows inflation fluid and instruments to be introduced into the balloon. The window may be used to view the tissue layers, via an endoscope inserted through the bore and into the balloon, regardless of whether the balloon is inflated.

In another class of embodiments, the invention is an apparatus for tissue dissection and instrument anchoring, which includes a dissection balloon having nonuniform elasticity selected to achieve desired inflated shape and pressure characteristics. In a preferred embodiment, the dissection balloon comprises a sheet of relatively inelastic material bonded to another sheet of relatively elastic material. In another preferred embodiment, the dissection balloon consists of a first large sheet bonded (such as by RF-welding) to a second large sheet, and a reinforcing sheet bonded to the central portion of each large sheet. The two large sheets are made of material having high elasticity (preferably polyurethane), and the reinforcing sheet can be made of material having high or relatively low elasticity.

In other embodiments, the invention is a balloon (either an anchoring or dissection balloon) having nonuniform elasticity selected to achieve desired inflated shape and pressure characteristics, for use in an apparatus for tissue dissection, tissue retraction, and instrument anchoring.

Other embodiments of the invention are methods for using an apparatus for tissue dissection and instrument anchoring, said apparatus including a long-necked dissection balloon deployed through a cannula. The dissection balloon has a window at its distal end, or nonuniform elasticity selected to achieve desired inflated shape and pressure characteristics, or both such a window and such nonuniform elasticity. The distal end of the dissection balloon is inserted between tissue layers and inflated to dissect the tissue layers. In some embodiments, after dissection using the dissection balloon, the dissection balloon is deflated and withdrawn through the cannula before a medical operation is performed in a working space between the dissected tissue layers. In other embodiments, after dissection using the dissection balloon, the dissection balloon is deflated but retained in the patient during performance of a medical operation. In other embodiments, where the dissection balloon has lobes of other portions shaped so that instruments can be positioned between them, the dissection balloon remains inflated in the patient after the tissue layers have been dissected, instruments are then positioned between the dissected tissue layers without being obstructed by the inflated dissection balloon (e.g., between lobes or other separated portions thereof), and the instruments are manipulated to perform a medical operation.

Another embodiment of the invention is a technique for packing a balloon in a manner which provides a tunnel through the packaged balloon for insertion of a laparoscope or other instrument, and which eliminates the need for packaging the balloon with an obturator positioned within it.

BRIEF DESCRIPTION OF THE DRAWINGS

FIGS. 1A–1C and 2A–2B show a two-component apparatus for separating tissue layers and insufflating the space between the separated layers, where:

FIG. 1A is the separation component of the two-component apparatus;

FIG. 1B is part of the distal part of the separation component of the two-component apparatus with the main envelope in its everted position;

FIG. 1C is part of the distal part of the separation component of the two-component apparatus with the main envelope in its inverted position;

FIG. 2A is the insufflation component of the two-component apparatus with the toroidal inflatable chamber in its collapsed state; and FIG. 2B is the insufflation component of the two-component apparatus with the toroidal inflatable chamber in its expanded state.

FIG. 3A shows an incision made through the abdominal wall, including the properitoneal fat layer, excluding the peritoneum;

FIG. 3B shows the distal part of the separation component of a two-component apparatus inserted into the incision (the separation component includes the main envelope in its collapsed state);

FIG. 3C shows the main envelope inflated to its expanded state to separate the peritoneum from the overlying layer;

FIG. 3D shows the main envelope returned to its collapsed state;

FIG. 3E shows the separation component removed from the incision;

FIG. 3F shows the distal part of the insufflation component of the two-component apparatus inserted into the incision;

FIG. 3G shows the toroidal inflatable chamber of the insufflation component inflated to its expanded state and the anchor flange slid into contact with the skin of the abdominal wall to provide a gas-tight seal;

FIG. 3H shows the working space between the peritoneum and the overlying layer insufflated with a gas passed through the bore of the insufflation component; and FIG. 3I shows additional instruments passed through gas-tight trocar sheaths into the insufflated working space to repair the hernia by attaching a mesh patch to the properitoneal fascia.

FIGS. 4A–4C show an embodiment of a first one-component apparatus for tissue dissection and instrument anchoring, where:

FIG. 4A shows a main embodiment of the one-component apparatus with the main envelope in its expanded state;

FIG. 4B shows details of the area marked "A" at the distal end of the tube assembly in FIG. 4A; and FIG. 4C shows the distal part of the tube assembly with the toroidal inflatable chamber in its expanded state.

FIG. 5A shows the alternative embodiment with the main envelope in its expanded state;

FIG. 5B shows the elongated main envelope of the alternative one-component apparatus;

FIG. 5C shows the distal part of the tube assembly of the alternative one-component apparatus with the main envelope in its everted state; and FIG. 5D shows the distal part of the tube assembly of the alternative one-component apparatus with the main envelope in its inverted state.

FIGS. 6A–6H are longitudinal cross sections of the abdomen illustrating a method of using a one-component apparatus to separate the peritoneum from the overlying layer, wherein:

FIG. 6A shows an incision made through the abdominal wall, including the overlying layer, excluding the peritoneum;

FIG. 6B shows the distal part of the tube assembly of the one-component apparatus inserted into the incision. The tube assembly includes the main envelope in its collapsed state;

FIG. 6C shows the main envelope inflated to its expanded state to separate the peritoneum from the overlying layer;

FIG. 6D shows the main envelope returned to its fully collapsed state;

FIG. 6E shows the apparatus advanced into the incision such that the envelope of the toroidal inflatable chamber clears the incision;

FIG. 6F shows the toroidal inflatable chamber inflated to its expanded state;

FIG. 6G shows the anchor flange slid into contact with the skin of the abdominal wall. The anchor flange together with the expanded toroidal inflatable chamber provides a gas-tight seal; and FIG. 6H shows the space between the peritoneum and the overlying layer insufflated with a gas passed through the bore of the apparatus.

FIGS. 7A and 7B show a second embodiment of a one-component apparatus, wherein:

FIG. 7A shows the second one-component apparatus with the main envelope in its expanded state; and FIG. 7B shows the second one-component apparatus with the main envelope in its collapsed state.

FIG. 8B shows the second one-component apparatus with the main inflatable chamber in its partially expanded state and an endoscope passed through the bore of the inner tube and through the bore of the main envelope.

FIGS. 9A–9H are longitudinal cross sections of the abdomen, wherein:

FIG. 9A shows an incision made through the abdominal wall, including the overlying layer, excluding the peritoneum;

FIG. 9B shows the distal part of the apparatus inserted into the incision. A tube assembly of the apparatus includes a main envelope in its collapsed state;

FIG. 9C shows the main envelope inflated to a partially-expanded state to separate part of the peritoneum from the overlying layer;

FIG. 9D shows the main envelope returned to its collapsed state;

FIG. 9E shows the apparatus advanced in the direction of the groin to bring the main envelope to the limit of the separated part of the peritoneum;

FIG. 9F shows the main envelope re-inflated to a partially-expanded state to separate an additional part of the peritoneum from the overlying layer;

FIG. 9G shows the main envelope advanced to close to the site of the hernia and re-inflated to its fully inflated state to create a working space; and FIG. 9H shows a component of the apparatus advanced through the tunnel into the working space, and the toroidal inflatable chamber inflated to form a gas-tight seal with the entrance of the tunnel.

FIG. 9I is a plan view of the abdomen showing a component of the apparatus in position with its distal end in the working space and its toroidal inflatable chamber forming a gas-tight seal with the entrance of the tunnel. FIG. 9I shows the lesser extent to which the peritoneum is detached in the tunnel compared with in the working space.

FIG. 16 is a plan view of a dissection balloon designed in accordance with the invention.

FIG. 17 is a cross-sectional view of the balloon of FIG. 16, taken along line A—A.

FIG. 18 is a cross-sectional view of the balloon of FIG. 16, taken along line B—B.

FIG. 22 is a plan view of another dissection balloon designed in accordance with the invention.

FIGS. 26–35 are longitudinal cross sections of the abdomen, wherein:

FIG. 26 shows an incision made through the abdominal wall;

FIG. 27 shows the distal end of the apparatus inserted into the incision;

FIG. 28 shows dissection balloon 512 inflated to separate part of the peritoneum from the overlying layer;

FIG. 29 shows balloon 512 returned to its collapsed state;

FIG. 30 shows the apparatus advanced in the direction of the groin to bring balloon 512 to the limit of the separated part of the peritoneum;

FIG. 31 shows balloon 512 re-inflated to separate an additional part of the peritoneum from the overlying layer;

FIG. 32 shows balloon 512 advanced to a position close to the site of a hernia and re-inflated to create a working space;

FIG. 33 shows the dissection balloon assembly (512 and 513) and ring 514 removed from the rest of the apparatus (i.e., the retraction and anchoring subassembly), and anchor balloon 517 inflated;

FIG. 34 shows foam collar 504 advanced into contact with the patient; and

FIG. 35 shows the working space within the patient being insufflated (as a final step prior to performing a repair procedure within the working space).

FIG. 51A is a top view of a tissue dissection apparatus illustrating an alternative embodiment of a technique for packing the balloon according to the present invention.

FIG. 51B is a side view of the tissue dissection apparatus of FIG. 51A further illustrating the inventive packing technique.

FIG. 51C is a side view of the tissue dissection apparatus of FIG. 51B illustrating the use of an obturator to extend the balloon in the distal direction.

FIG. 51D is a cross-sectional side view of the proximal portion of the cannula of the tissue dissection apparatus of FIG. 51A.

DETAILED DESCRIPTION OF THE PREFERRED EMBODIMENTS

Figure 3A:
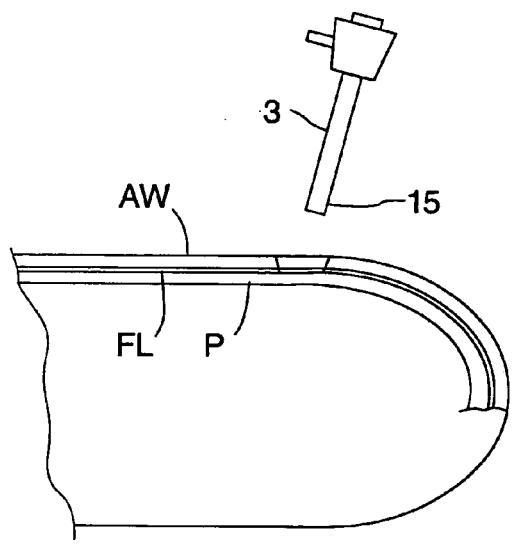
FIGS. 3A–3I are longitudinal cross sections of the abdomen illustrating a method of using a two-component apparatus to separate the peritoneum from the overlying layer, where.

Throughout the disclosure, including in the claims, the term "balloon" is used in a broad sense to denote any inflatable structure, regardless of the elasticity of the material comprising it. For example, the term balloon is employed to denote both a thin-walled, inflatable structure consisting of material of low elasticity (which does not stretch significantly during inflation), and also a thin-walled, inflatable structure consisting of highly elastic material such as a sheet of urethane (which does stretch significantly during inflation). In preferred embodiments to be described, the invention employs a balloon having nonuniform elasticity (elasticity which varies from one place to another on the balloon's surface).

Throughout the disclosure, the term "one-component" apparatus denotes, with reference to an apparatus for tissue dissection and instrument anchoring, an apparatus having a cannula, wherein after the cannula is inserted into a patient, it remains in the patient during tissue dissection using the apparatus and during anchoring of the apparatus in the patient to enable performance of medical procedures (subsequent to dissection) using the apparatus.

Another device for separating tissue layers is disclosed in U.S. patent application Ser. No. 07/911,714, of which this application is a C.I.P. The device includes a main envelope that defines a main inflatable chamber. The apparatus also includes an introducing device for introducing the main envelope in a collapsed state between the first layer of tissue and the second layer of tissue. The introducing device inflates the main envelope into an expanded state to separate the first layer of tissue from the second layer of tissue, and to create a working space between the first layer of tissue and the second layer of tissue. Finally, the apparatus includes an insufflation device for introducing insufflation gas into the working space between the first layer of tissue and the second layer of tissue.

In a method according to U.S. application Ser. No. 07/911,714, a first layer of tissue is separated from a second layer of tissue using a main envelope (defining a main inflatable chamber) and insufflation gas. The main envelope is introduced in a collapsed state between the first and second layers of tissue, and the main envelope is then inflated into an expanded state to create a working space between the first and second layers of tissue. Finally, insufflation gas is introduced into the working space between the first and second layers of tissue.

U.S. Ser. No. 07/911,714 discloses a two-component apparatus including an inflatable main envelope and a device for introducing the main envelope (together constituting a first component which separates a first layer of tissue from a second layer of tissue to create a working space) and an insufflation device which insufflates the working space to maintain separation of the first layer of tissue from the second layer. The insufflation device is tubular, has an anchor flange slidably mounted on it, and has a toroidal inflatable chamber at its distal end. The anchor flange and toroidal inflatable chamber together form a gas-tight seal with the second layer of tissue.

In a method disclosed in U.S. Ser. No. 07/911,714 for using the two-component apparatus, the introducing device pushes the main envelope in a collapsed state through an incision through the second layer of tissue to place the main envelope between the first and second layers of tissue. The main envelope is then inflated to gently separate the first and second tissue layers. An endoscope may be passed through the bore of the introducing device into the main chamber to observe the extent of separation of the layers of tissue. The main envelope is then returned to a collapsed state, and the main envelope and introducing device are removed through the incision. Next, the insufflating device is inserted into the incision so that its distal end projects into the working space between the two layers of tissue, and the toroidal inflatable chamber is inflated. The anchor flange is slid distally along the insufflating device to compress the second layer of tissue between it and the expanded toroidal inflatable chamber, and thus to form a gas-tight seal. Insufflating gas is then passed through the insufflating device into the working space to maintain the separation of the first layer of tissue from the second. An endoscope may be passed through the bore of the insufflating device into the working space to observe within the working space.

A two-component apparatus (of the type disclosed in referenced U.S. Ser. No. 07/911,714) for separating tissue layers and insufflating the space between the separated layers is shown in FIGS. 1A–1C and 2A–2B. FIG. 1A shows a partially cut-away view of separation component 1 of the apparatus. In separation component 1, introducer tube 3 is a rigid tube having a bore with a circular cross section that can accommodate an endoscope.

The proximal end of introducer tube 3 is fitted with a port 5, in the proximal end 7 of which is mounted a flapper valve 2. Shutter 6 of flapper valve is operated by button 9. Seat 4 of the flapper valve additionally forms a gas-tight seal with an endoscope or other instrument inserted though the flapper valve into the bore of introducer tube 3. Port 5 is also fitted with a valve 11 to which a supply of a suitable inflation fluid can be connected.

Main envelope 12 defines a main inflatable chamber 13. Main envelope 12 is fitted to distal end 15 of introducer tube 3. Main envelope 12 is shown in a collapsed state in FIGS. 1B and 1C. Dotted line 12X indicates the extent of main envelope 12 with chamber 13 in its expanded state. It should be noted that although the main envelope 12 is illustrated as generally spherical, it can be formed as oblong, "hockey puck" or disc shaped, kidney bean shaped or in other shapes as suited for the particular dissection contemplated.

Main envelope 12 is preferably formed from an elastomeric material, such as latex, silicone rubber, or polyurethane. The main envelope can also be formed from a thin, inelastic material such as Mylar®, polyethylene, nylon, etc. If an inelastic material is used, it should be suitably packaged to fit inside the bore of introducer tube 3 when in its collapsed state.

The preferred elastomeric main envelope 12 can be simply attached to the distal end 15 of the introducer tube 3 by stretching the main envelope over the distal end of the introducer tube, as shown in FIG. 1B. The main envelope is then kept in place by friction resulting from the tension caused by stretching. A suitable adhesive, such as an epoxy or cyanoacrylate adhesive, may additionally or alternatively be used. Other means of attaching the main envelope to the inside or the outside of the introducer tube can be used.

After attachment, main envelope 12 is inverted into the bore of the introducer tube, as shown in FIG. 1C. Inverting the main envelope into the bore of the introducer tube makes it easier to use the introducer tube to pass the main envelope through an incision and place it adjacent to the peritoneum, as will be described.

The first part of a method (described in U.S. Ser. No. 07/911,714) using separation component 1 of the two-component apparatus of FIGS. 1A–1C and 2A–2B to separate a first layer of tissue from a second layer of tissue will next be described with reference to FIGS. 3A–3E (the entire method, for repairing a hernia, will be described with reference to FIGS. 3A–3D).

Figure 3B:
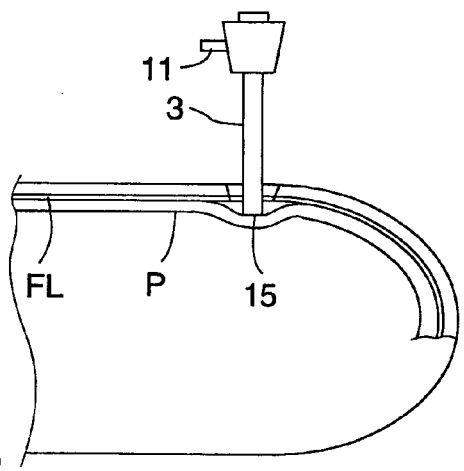

FIGS. 3A–3I show a longitudinal cross section of the lower abdomen. As indicated by FIG. 3A, an incision about 12–15 mm long is made in the abdominal wall (AW), and is carried through the abdominal wall as far as, and including, the properitoneal fat layer (FL). Distal end 15 of introducer tube 3 of separation component 1 is then inserted into the incision to bring the distal end into contact with the peritoneum (P). Additional gentle pressure detaches the part of the peritoneum in the immediate vicinity of the incision from the overlying layer, as shown in FIG. 3B. FIG. 3B shows the peritoneum (P) detached from the properitoneal fat layer (FL). The deflated main envelope cannot be seen in FIG. 3B because it is inverted within the bore of introducer tube 3.

A source of a suitable inflation fluid (not shown) is connected to valve 11. A gas, preferably air, is the preferred inflation fluid, but other gases, such as carbon dioxide, can be used. A liquid, such as saline solution, can be used, but liquids are less preferable than gases because liquids change the optical properties of any endoscope inserted into main inflatable chamber 13. The flow of inflation fluid is turned on, which ejects the main envelope 12 of main inflatable chamber 13 from the bore of introducer tube 3.

Figure 3C:
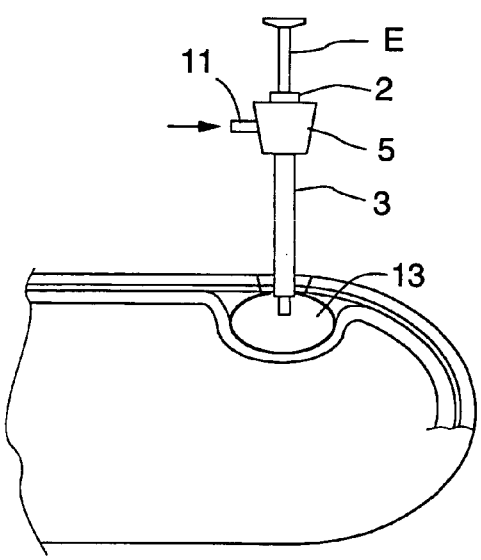

The inflation fluid progressively expands the main envelope 12, and hence the main inflatable chamber 13 defined by the main envelope, into an expanded state (as shown in FIG. 3C). The main envelope expands between the peritoneum and the properitoneal fascia, and gently and progressively detaches an increasing area of the peritoneum from the overlying layer as it expands. When the main envelope is in its expanded state, the main inflatable chamber is preferably about 4"–6" (100–150 mm) in diameter.

Early in the process of expanding the main envelope 12, an endoscope E is inserted into flapper valve 2 in port 5, as shown in FIG. 3C. Endoscope E is passed through the bore of introducer tube 3 into the main inflatable chamber 13. Once partially expanded, main envelope 12 is sufficiently transparent for the extent of the detachment of the peritoneum to be observed through the endoscope.

Figure 3D:
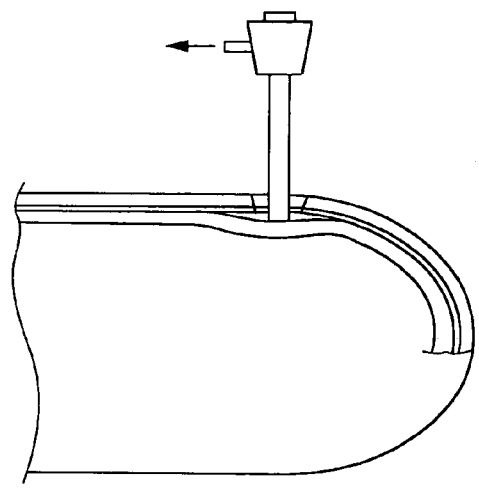
Figure 3E:
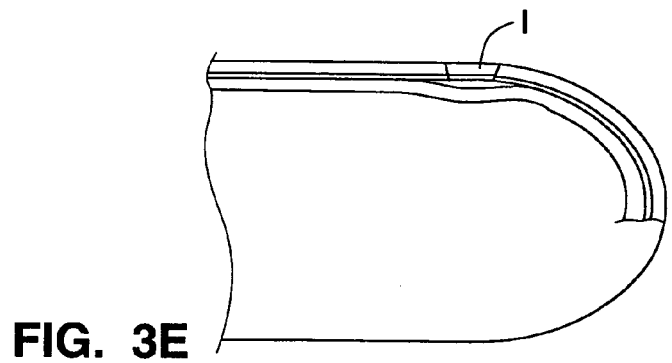

When a sufficient area of the peritoneum has been detached, the supply of inflation fluid is turned off. The inflation fluid is then vented from the main inflatable chamber, and main envelope 12 returns to its collapsed state. The peritoneum remains detached from the properitoneal fascia, however, as shown in FIG. 3D. Separation component 1, including the collapsed main envelope, is then withdrawn from the incision I (FIG. 3E).

Insufflation component 21 (shown in FIGS. 2A and 2B) of the two-component apparatus of FIGS. 1A–1C and 2A–2B will next be described. Insufflation component 21 comprises inner tube 35 and outer tube 37 mounted coaxially, with the outer tube covering the inner tube over most of the length of the inner tube. The inner tube is similar to the introducer tube 3 (FIG. 1A), and is a rigid tube having a bore with a circular cross section that can accommodate a 10 mm endoscope.

The proximal end of inner tube 35 is fitted with a port 25, the proximal end 27 of which has a flapper valve 32. Shutter 36 of the flapper valve is operated by button 29. Seat 34 of the flapper valve forms a gas-tight seal with an endoscope (not shown) or an obturator (such as obturator 33) inserted though the flapper valve into the bore of inner tube 35. Port 25 is also fitted with a first valve 31 to which a supply of a suitable insufflation fluid can be connected.

Distal end 41 of outer tube 37 stops short of distal end 39 of inner tube 35. Insufflation component 21 includes a toroidal inflatable chamber 43. Envelope 45 of toroidal chamber 43 is a cylindrical piece of a thin elastomeric material, such as latex, silicone rubber, or polyurethane. Envelope 45 is placed over the distal ends of the inner tube and the outer tube. Proximal end 47 of envelope 45 is attached to distal end 41 of the outer tube, and distal end 49 of envelope 45 is attached to distal end 39 of the inner tube 35.

The bore of outer tube 37 is spaced from the outer surface of inner tube 35. Annular space 51 between the inner tube and the outer tube interconnects toroidal chamber 43 and a second valve 53. Second valve 53 is connected to a source of a suitable inflation fluid (not shown). Thus, toroidal envelope 45 can be inflated using an inflation fluid passing into toroidal inflatable chamber 43 (the volume enclosed by envelope 45) via the second valve 53 and the annular space 51. Toroidal inflatable envelope 45 is shown in its collapsed state in FIG. 2A, and in its expanded state in FIG. 2B.

Anchor flange 55 is slidably mounted on the outer tube 37, and can be locked in a desired position along the length of the outer tube with a simple over-center action locking lever (not shown). As will be described in detail below, the anchor flange and the toroidal inflatable chamber, in its expanded condition, enable the insufflator component 21 to form a gas-tight seal to prevent insufflation gas passed through the insufflator component from escaping.

The use of insufflation component 21 in the second part of the method of FIGS. 3A–3I using the two-component apparatus of FIGS. 1A–1C and 2A–2B will next be described. It is preferred to use separation component 1 in conjunction with the first part of the method (described with referenced to FIGS. 3A–3E) and for dissecting the first and second tissue layers, but the second part of the method (using insufflation component 21) may be used in following any other dissection operation including manual dissection with an endoscope, graspers, operating scope or any blunt instrument which may be used to dissect the tissue layers by sweeping the area between the layers.

Figure 3F:
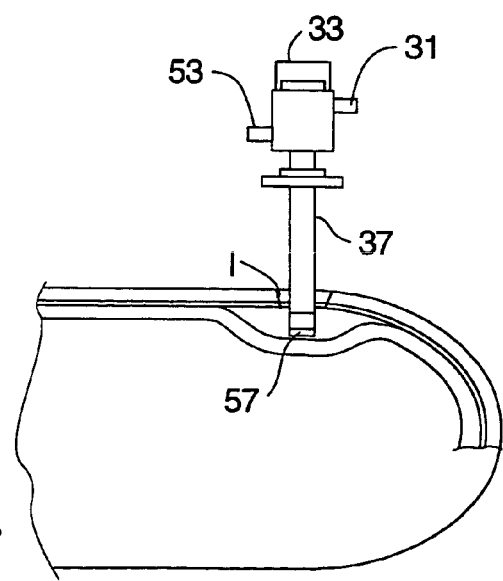

With reference to FIG. 3F, obturator 33 of component 21, having blunt tip 57, is inserted past flapper valve 32 (shown in FIG. 2B) into the bore of inner tube 35. Tip 57 of obturator 33 projects beyond the distal end of the inner tube to provide insufflation component 21 with a blunt nose. The blunt nose enables the distal end of insufflation component 21 to be atraumatically inserted into the properitoneal space through incision I. The insufflation component is advanced through the incision until the proximal end of the cylindrical envelope 45 is in the properitoneal space, clear of the incision, as shown in FIG. 3F.

A suitable source (not shown) of an inflation fluid is attached to second valve 53. A gas, such as air or carbon dioxide, can be used for the inflation fluid; alternatively, a liquid, such as saline can be used. Since the volume of inflation fluid required to inflate the toroidal inflatable chamber is small, about 15 ml in the preferred embodiment, the inflation fluid can be forced into the toroidal inflatable chamber from a large syringe. Inflation fluid is fed into toroidal inflatable chamber 43 to expand the toroidal inflatable chamber to its expanded condition, as shown in FIG. 3G.

Figure 3G:
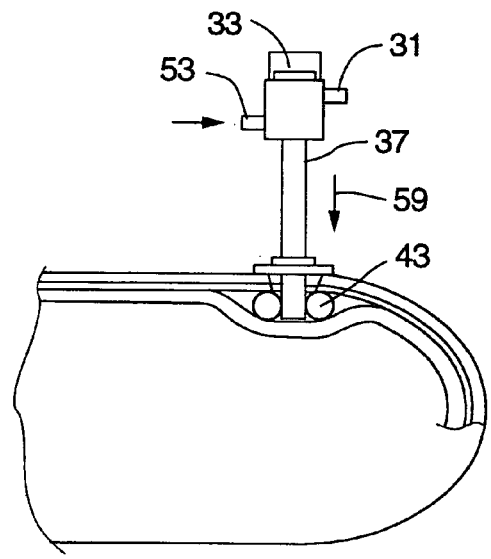
Figure 3H:
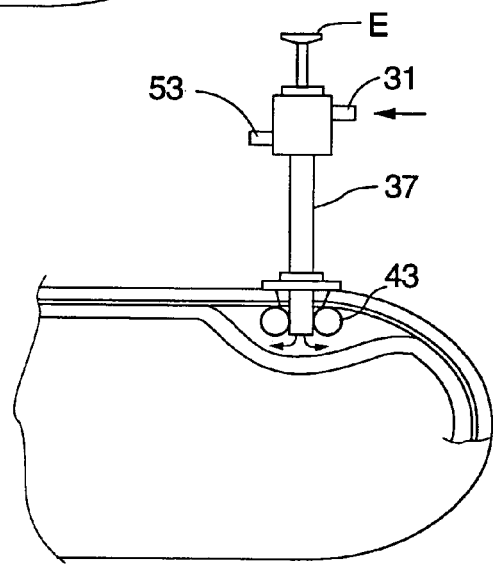

Anchor flange 55 is then advanced in the direction of arrow 59 along outer tube 37 to bring anchor flange 55 into contact with the skin of the abdominal wall (as shown in FIGS. 3G and 3H). Insufflation component 21 is then gripped, and the anchor flange is further advanced slightly. This forces the expanded toroidal inflatable chamber 43 into contact with the overlying layer, and slightly compresses the abdominal wall (including the overlying layer but excluding the peritoneum) between the toroidal inflatable chamber and the anchor flange. Once adjusted, the anchor flange is locked in position on the outer tube. The expanded toroidal inflatable chamber is held against the overlying layer, and forms a gas-tight seal between the insufflation component and the abdominal wall (including the overlying layer but excluding the peritoneum).

A suitable source (not shown) of an insufflation gas is attached to first valve 31, and insufflation gas is passed through the bore of inner tube 35 into the working space between the peritoneum and the overlying layer created by separating by the peritoneum from the overlying layer using the separation component of the apparatus in the first part of the method described above. The pressure of the insufflation gas re-separates the peritoneum from the overlying layer, as shown in FIG. 3H, and provides a working space in which repair of the hernia can be carried out. The obturator is removed from the bore of inner tube 35. The bore of inner tube 35 can then be used to pass instruments, such as the endoscope, into the working space to perform the repair procedure. Insufflation pressure is maintained by flapper valve 32.

Figure 3I:
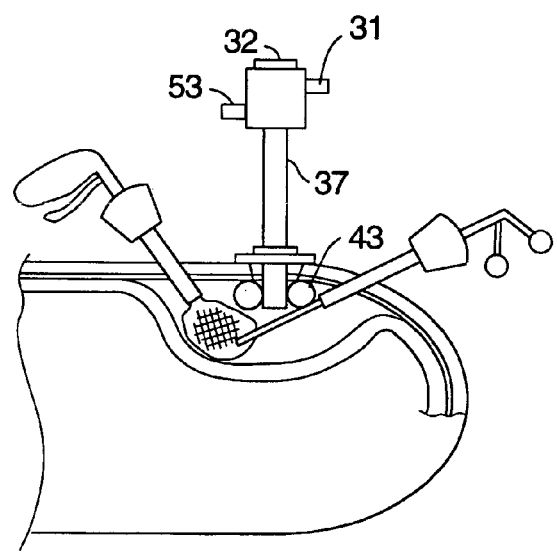

As part of the hernia repair procedure, additional gas-tight trocar sheaths are inserted through the abdominal wall into the working space, as shown in FIG. 3I. An endoscope (not shown) can be passed into the working space through the bore of inner tube 35, or through one of the additional trocar sleeves for observation. If the properitoneal fat layer remains attached to the properitoneal fascia, it is scraped off the fascia around the site of the hernia so that the patch can be attached directly to the fascia.

A patch, preferably a Dacron® or Teflon® mesh, shown gripped by grippers, is passed through the sleeve of one trocar into the working space. Using the grippers, the patch is manipulated to place it in contact with the properitoneal fascia over the site of the hernia. The patch is attached to the properitoneal fascia by staples inserted using a stapler passed through the trocar sleeve into the working space. Sutures can alternatively be used to attach the patch to the properitoneal fascia.

After the treatment procedure is completed, first valve 31 is operated to release the insufflation gas from the working space. Second valve 53 is operated to release the inflation fluid from toroidal inflatable chamber 43. Envelope 45 of the toroidal inflatable chamber returns to its collapsed state, flush with the outer surfaces of the inner tube and outer tube 37. Insufflating component 21 is then withdrawn from the incision, and the incision is closed using sutures or clips. The pressure of the viscera against the peritoneum returns the peritoneum into contact with the overlying layer. Over time, the peritoneum reattaches to the overlying layer.

Several embodiments of a one-component apparatus are disclosed in U.S. Ser. No. 07/911,714. Each such one-component apparatus includes assemblies for performing multiple functions, including: introducing and inflating a main envelope to dissect tissue layers within a patient; anchoring the apparatus to the patient and insufflating the working space; and returning the inflated main envelope to a collapsed state. In some of these embodiments, the main envelope is deployed through an elongated tube, and the anchoring means includes an anchor flange slidably mounted on the elongated tube and a toroidal inflatable chamber at the distal end of the elongated tube. The anchor flange and toroidal inflatable chamber can be controlled to form, together, a gas-tight seal with the second layer of tissue.

One-component apparatus 121 (one of the one-component apparatus embodiments disclosed in U.S. Ser. No. 07/911, 714) is shown in FIG. 4A. Apparatus 121 is similar to insufflation device 21 of FIGS. 2A–2B, and components of apparatus 121 corresponding to those of device 21 are identified by the same reference numbers as in FIGS. 2A–2B with "100" added thereto. Apparatus 121 comprises tube assembly 160, including an inner tube 135 coaxially mounted inside an outer tube 137. Outer tube 137 covers inner tube 135 over most of the length of the inner tube. The inner tube is a rigid tube having a bore with a circular cross section that can accommodate an endoscope (not shown).

The proximal end of the inner tube 135 is fitted with a port 125, the proximal end 127 of which includes a flapper valve 132. The shutter 136 of the flapper valve is operated by the button 129. Additionally, the seat 134 of the flapper valve forms a gas-tight seal with an endoscope (not shown), or other instrument, inserted though the flapper valve into the bore of the inner tube 135. The port 125 is also fitted with a first valve 131 to which a supply of a suitable insufflation fluid can be connected.

Unlike insufflator device 21 of FIGS. 2A and 2B, the distal end of outer tube 137 extends as far as the distal end of inner tube 135. Tubes 135 and 137 are connected together over a distal portion 167 of their lengths (see detail in FIG. 4B). Circumferential groove 169 is formed in the inner wall of distal portion 167. Groove 169 is shown with a wedge-shaped cross section, but can have other cross sections, such as square, or semi-circular. Circumferential groove 169 retains main envelope 112, which defines main inflatable chamber 113, in the bore of inner tube 135.

Envelope 145 of toroidal inflatable chamber 143 covers the distal part of tube assembly 160. Envelope 145 is a cylindrical piece of thin elastomeric material, such as a latex, silicone rubber, or polyurethane. The proximal end 147 and the distal end 149 of the envelope are attached to the outer surface 163 of the tube assembly using a circumferential line of adhesive applied at each end of the envelope. An epoxy or cyanoacrylate adhesive is preferably used. When chamber 143 is in its collapsed state, envelope 145 lies almost flush with the outer surface of tube assembly 160.

Outer tube 137 is spaced from inner tube 135 over at least part of its circumference. Space 151 between the inner tube and the outer tube, and radial passage 161 through the wall of the outer tube interconnect chamber 143 and second valve 153. Second valve 153 is connected to a source of suitable inflation fluid (not shown). Chamber 143 is shown in its collapsed state in FIGS. 4A and 4B, and in its expanded state in FIG. 4C.

Anchor flange 155 is slidably mounted on tube assembly 160, and can be locked in a desired position along the length of the tube assembly with a simple over-center action locking lever (not shown). As will be described below, anchor flange 155 and toroidal inflatable chamber 143 in its expanded condition form a gas-tight seal to prevent insufflation gas from escaping.

The apparatus of FIGS. 4A–4C also includes main envelope 112 detachably attached to the bore of inner tube 135. The main envelope defines main inflatable chamber 113. Main envelope 112 is preferably formed of an elastomeric material such as latex, silicone rubber, or polyurethane (but can also be formed from a thin, inelastic material such as Mylar®, polyethylene, nylon, etc.). If an inelastic material is used for envelope 112, it should be suitably packaged to fit inside the bore of the inner tube when in its collapsed state.

Main envelope 112 is formed such that it has a substantially spherical shape when in its expanded state, and is also formed with a neck 165. Neck 165 has an outside diameter substantially equal to the diameter of the bore of inner tube 135. Neck 165 can be rolled outward a number of times, as in the neck of a common toy balloon, or the neck can be attached to a suitable O-ring 171 as shown in FIG. 4B. The rolled neck, or the O-ring attached to the neck, engages with the circumferential groove 169 in the inner wall in the inner tube to attach main envelope 112 to the inner tube. Main envelope 112 is housed in the bore of the inner tube when the main inflatable chamber is in its collapsed state.

Rip cord 173, attached to neck 165 of main envelope 112, runs proximally up the bore of inner tube 135 and emerges from port 125 through flapper valve 132. The part of the rip cord 173 emerging from the flapper valve can be gripped and pulled in a proximal direction to release the rolled neck 165 or the O-ring 171 from the circumferential groove 169. By pulling further on the rip cord, the entire main envelope can be pulled proximally through the bore of the inner tube.

Figure 5A:
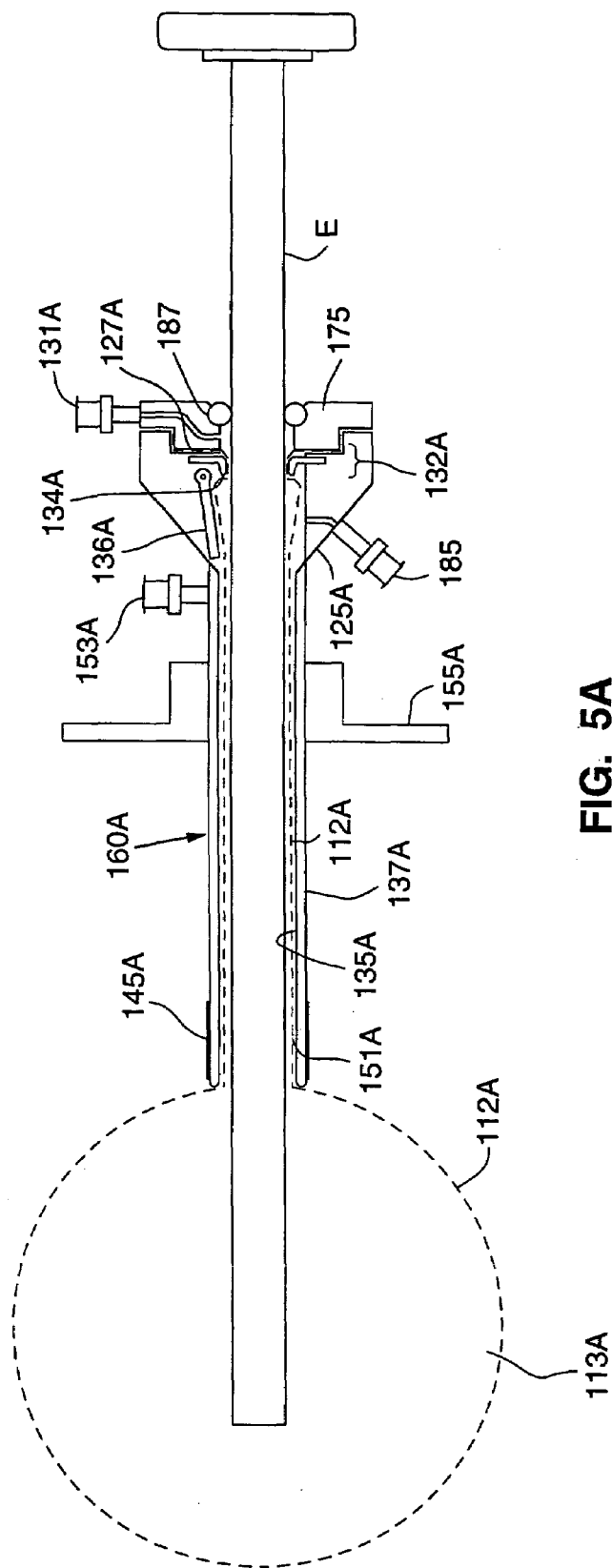
FIGS. 5A–5D show an alternative one-component apparatus for tissue dissection and instrument anchoring, where.

FIG. 5A shows a one-component apparatus (which is a variation on the apparatus of FIGS. 4A–4C) having an elongated main envelope 112A. As shown in FIG. 5A (and described in referenced U.S. application Ser. No. 07/911, 714), tube assembly 160A includes inner tube 135A mounted coaxially inside outer tube 137A, with the proximal and distal ends of the tubes interconnected. Space 151A between the inner tube and the outer tube communicates with the toroidal inflatable chamber through a radial passage in the wall of the outer tube. The space between the inner tube and the outer tube also communicates with the toroidal chamber inflation valve 153A. The bore of the inner tube 135A communicates with the port 125A, fitted with the insufflation valve 185. The port 125A is also fitted with a flapper valve 132A, including the flapper valve seat 134A, which maintains gas pressure when the apparatus is used for insufflation. Flapper valve seat 134A also provides a gas-tight seal around any instrument, such as endoscope E, passed through the flapper valve.

Figure 5B:
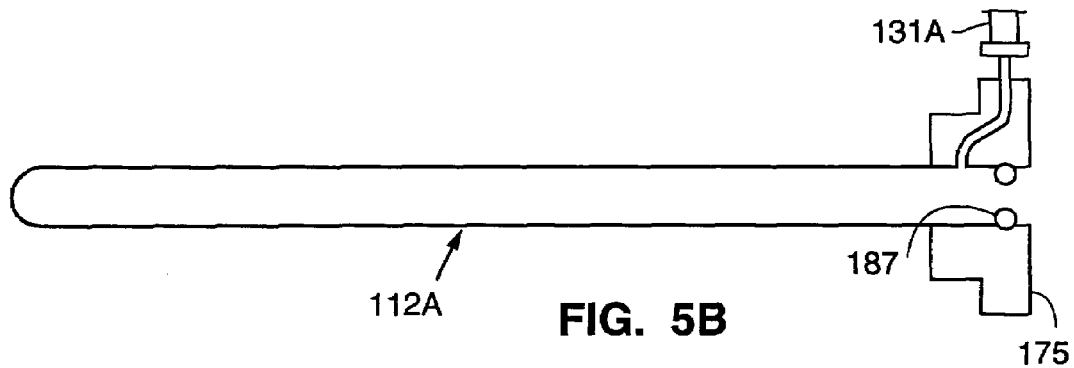

Elongated main envelope 112A is shown in FIG. 5B. The main envelope is an elongated cylinder with a closed distal end 177. The main envelope is preferably formed from an elastomeric material, such as latex, silicon rubber, or polyurethane. Attached to the proximal end of the main envelope is a manifold 175 which mates with the proximal face 127A of the port 125A. The manifold 175 is fitted with an O-ring seal 187, which forms a gas-tight seal with any instrument passed through it. The manifold 175 is also fitted with the main chamber inflation valve 131A to which a supply (not shown) of a suitable inflation fluid can be attached to inflate the main inflatable chamber 112A.

Figure 5C:
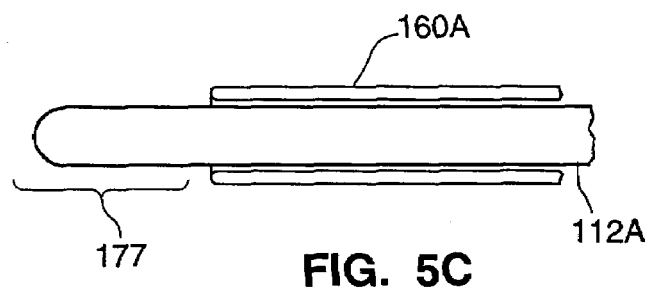
Figure 5D:
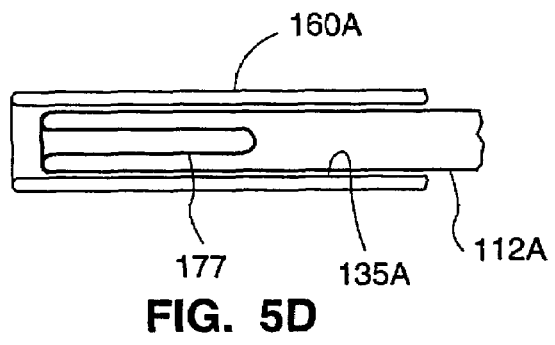

Elongated main envelope 112A is passed through flapper valve 132A into the bore of inner tube 135A. The manifold 175 is engaged with the proximal face 127A of the port 125A. When the manifold is engaged, the distal end 177 of the main envelope projects beyond the distal end of the tube assembly 160A, as shown in FIG. 5C. The distal end of the main envelope is then inverted into the bore of the inner tube 135A, as shown in FIG. 5D.

An endoscope, or other suitable instrument, is inserted through O-ring seal 187 to seal the manifold before inflation fluid is passed through main chamber inflation valve 131A to inflate main inflatable chamber 113A.

Alternatively, seal 187 can be replaced by an additional flapper valve (not shown) so that the main inflatable chamber can be inflated without the need to use an instrument to seal the manifold.

When inflation fluid is passed into main inflatable chamber 113A through valve 131A, distal end 177 of main envelope 112A is ejected from inner tube 135A. The inflation fluid then progressively expands the main envelope 112A, and hence main inflatable chamber 113A defined by the main envelope, into an expanded state as shown in FIG. 5A. The part of the main envelope inside the inner tube is subject to the same inflation pressure as the distal end 177 of the main envelope, but is constrained by the inner tube and so does not inflate.

After using main envelope 112A to separate (dissect) the peritoneum from an adjacent tissue layer, as will be described below, the inflation pressure fluid is vented from main inflatable chamber 113A, and main envelope 112A returns to its collapsed state. When the main envelope is in its collapsed state, it can move freely in the bore of inner tube 135. The main envelope is removed from the inner tube by disengaging manifold 175 from the proximal face 127A of port 125A, and using manifold 175 to pull the main envelope proximally through the bore of the inner tube.

Inflation fluid for the toroidal inflatable chamber (envelope 145A of which is shown in FIG. 5A), is passed through toroidal chamber inflation valve 153A. Insufflation gas is passed through insufflation valve 185.

The toroidal inflatable chamber and anchor flange 155A of the embodiment of FIGS. 5A–5D are the same as in the embodiment of FIGS. 4A–4C, and will not be described again.

In a method according to U.S. Ser. No. 07/911,714 of using a one-component apparatus to separate a first layer of tissue from a second layer of tissue, the elongated tube pushes the main envelope in a collapsed state through an incision through the second layer of tissue to place the main envelope between the first layer of tissue and the second layer of tissue. The main envelope is then inflated to gently separate the first layer of tissue from the second layer of tissue, thereby creating a working space between the two layers of tissue. An endoscope may be passed through the bore of the single elongated tube into the main chamber to observe the extent of separation of the layers of tissue. The main envelope is then returned to a collapsed state, detached from the elongated tube, and removed from the working space between the layers of tissue through the bore of the elongated tube. The toroidal inflatable chamber at the distal end of the elongated tube is then inflated into an expanded state. The anchor flange is slid distally along the elongated tube to compress the second layer of tissue between it and the expanded toroidal inflatable chamber to form a gas-tight seal. Insufflating gas is passed through the elongated tube into the working space to maintain the separation of the first and second tissue layers. An endoscope may be passed through the bore of the single elongated tube into the working space to observe within the working space.

Such a method (described in U.S. Ser. No. 07/911,714) of using either the apparatus of FIGS. 4A–4C or that of FIGS. 5A–5D to separate a first layer of tissue from a second layer of tissue will next be described with reference to FIGS. 6A–6H. For specificity, FIGS. 6A–6H will be described with reference to separation of the peritoneum from the properitoneal fascia in the course of repairing a hernia using the apparatus of FIGS. 4A–4C.

Figure 6A:
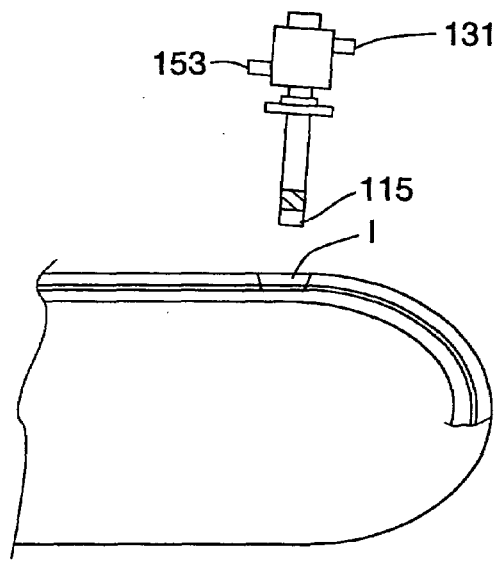
Figure 6B:
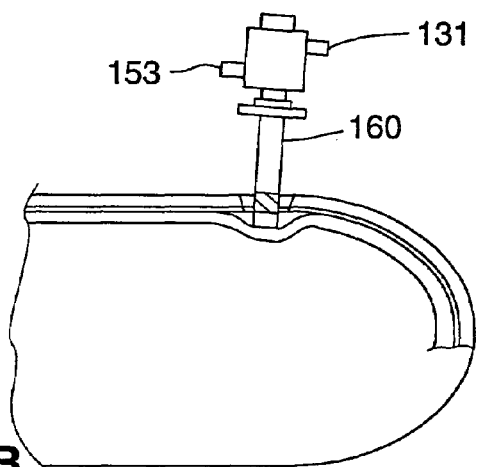

FIGS. 6A–6H show a longitudinal cross section of the lower abdomen. Incision I about 12–15 mm long is made in the abdominal wall, and carried through the abdominal wall as far as, and including the properitoneal fat layer as shown in FIG. 6A. Distal end 115 of tube assembly 160 of apparatus 121 is then inserted into the incision to bring the distal end into contact with the peritoneum. Additional gentle pressure detaches the part of the peritoneum in the immediate vicinity of the incision from the overlying layer, as shown in FIG. 6B. FIG. 6B shows the peritoneum detached from the properitoneal fat layer. The main envelope cannot be seen in FIGS. 6A and 6B because it is inverted within the bore of the tube assembly.

A source of inflation fluid (not shown) is connected to valve 131. A gas, preferably air, is the preferred inflation fluid, but other gases, such a carbon dioxide can be used. A liquid, such as saline solution can be used, but liquids are less preferable because they change the optical properties of any endoscope inserted into main inflatable chamber 113. The flow of inflation fluid is turned on, which ejects main envelope 112 from the bore of tube assembly 160.

Figure 6C:
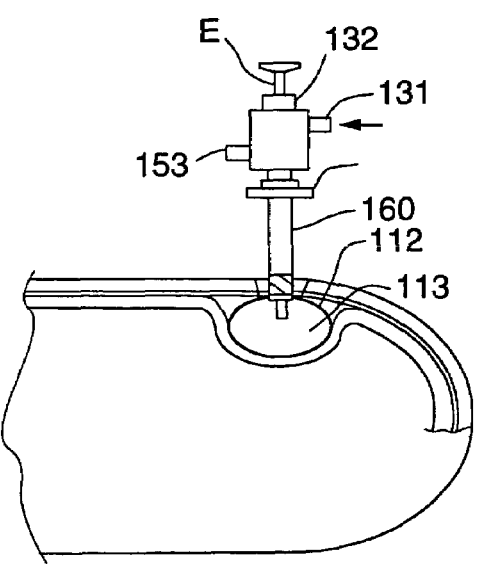

The inflation fluid progressively expands main envelope 112, and hence main inflatable chamber 113 defined by the main envelope, into an expanded state as shown in FIG. 6C. The main envelope expands between the peritoneum and the properitoneal fat layer, and gently and progressively detaches an increasing area of the peritoneum from the overlying layer as it expands. When the main envelope is in its expanded state, the main inflatable chamber is preferably about 4"–6" (100–150 mm) in diameter.

Early in the process of expanding main envelope 112, an endoscope E is inserted into flapper valve 132 in port 125 as shown in FIG. 6C. Endoscope E is passed through the bore of tube assembly 160 into main inflatable chamber 113. Once the main envelope is partially expanded, the main envelope is sufficiently transparent for the extent of the detachment of the peritoneum to be observed using the endoscope.

Figure 6D:
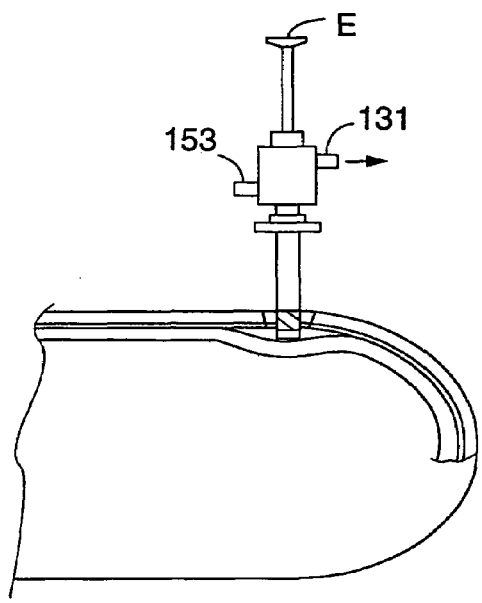

When a sufficient area of the peritoneum is detached, the supply of inflation fluid is turned off. The inflation fluid is then vented from main inflatable chamber 113, and the main envelope progressively returns to its collapsed state. The peritoneum remains detached from the overlying layer, however, as shown in FIG. 6D. The main envelope is then removed from the bore of tube assembly 160. The different methods of removing the main envelope from the bore of the tube assembly for the different forms of the one-component apparatus (that of FIGS. 4A–4C and that of FIGS. 5A–5D) are described above.

Figure 6E:
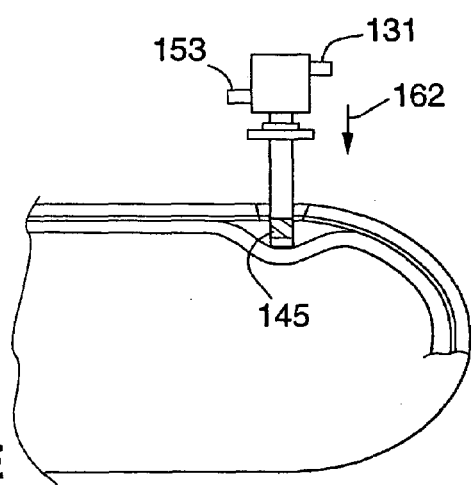

After main envelope 112 has been removed from the bore of the tube assembly, the tube assembly is advanced into the incision in the direction of arrow 162 until the proximal end of envelope 145 of the toroidal inflatable chamber is in the properitoneal space, clear of the incision, as shown in FIG. 6E.

Figure 6F:
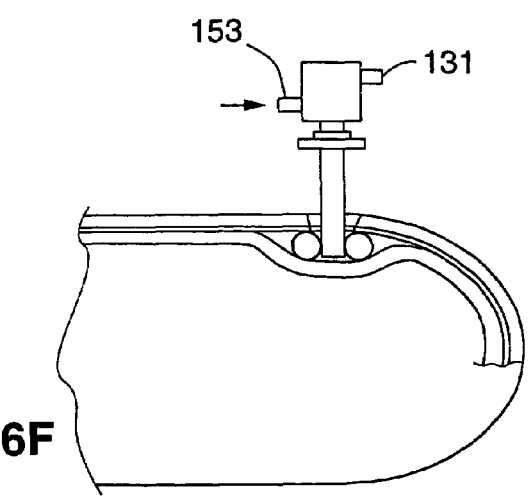

A suitable source (not shown) of an inflation fluid is attached to valve 153. A gas, such as air or carbon dioxide, can be used for the inflation fluid; alternatively, a liquid, such as saline can be used. Since the volume of inflation fluid required to inflate the toroidal inflatable chamber is small, about 15 ml in the preferred embodiment, the inflation fluid can be contained in a large syringe. Inflation fluid is fed into toroidal inflatable chamber 43 to expand the toroidal inflatable chamber to its expanded condition, as shown in FIG. 6F.

Figure 6G:
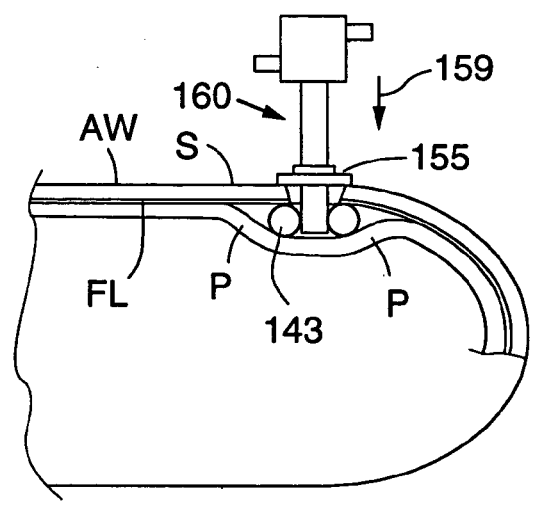

Anchor flange 155 is then advanced in the direction of arrow 159 along tube assembly 160 to bring the anchor flange into contact with the skin S of abdominal wall AW. Tube assembly 160 is then gripped, and the anchor flange is further advanced slightly. This forces the expanded toroidal inflatable chamber 143 into contact with the overlying layer, and slightly compresses abdominal wall AW, including the overlying layer but excluding the peritoneum P, between the expanded toroidal inflatable chamber and the anchor flange, as shown in FIG. 6G. Once adjusted, the anchor flange is locked in position on the tube assembly. The expanded toroidal inflatable chamber is held against the overlying layer and forms a gas-tight seal with the abdominal wall, excluding the peritoneum.

Figure 6H:
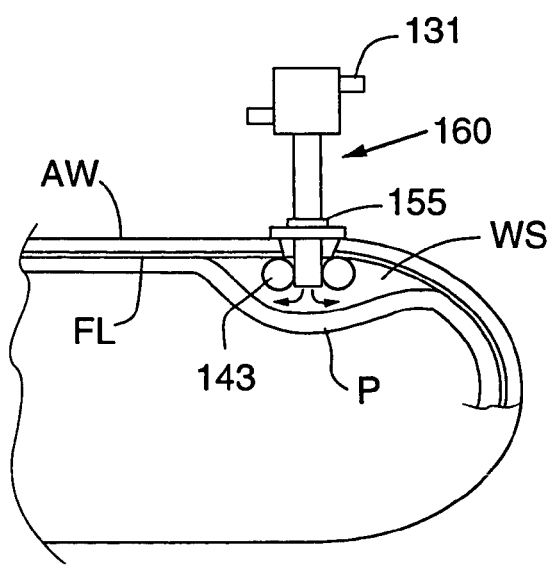

A suitable source (not shown) of insufflation gas is attached to first valve 131, and insufflation gas is passed through the bore of inner tube 135 into working space WS between the peritoneum P and the overlying layer created by separating the peritoneum from the overlying layer. The pressure of the insufflation gas re-separates the peritoneum from the overlying layer, as shown in FIG. 6H, and provides a working space in which repair of the hernia can be carried out. The bore of tube assembly 160 can be used to pass instruments, such as endoscope E, into the working space to perform the repair procedure. When no instrument is inserted into the bore of the tube assembly, insufflation pressure is maintained by the flapper valve.

As part of a hernia repair procedure, additional gas-tight trocar sleeves (not shown) are inserted through the abdominal wall into the working space. The same procedure described above in connection with FIG. 3I is used to attach a mesh patch to the properitoneal fascia over the site of the hernia. The process can be observed using an endoscope passed through the bore of tube assembly 160, or through one of the additional trocar sleeves.

After the treatment procedure is completed, valve 131 is operated to release the insufflation gas from the working space WS. Valve 153 is operated to release the inflation fluid from toroidal inflatable chamber 143, which releases compression of the abdominal wall AW, excluding the peritoneum. Toroidal inflatable chamber 143 returns to its collapsed state, with its envelope 145 flush with the outer surface tube assembly 160. The tube assembly is then withdrawn from the incision, and the incision is closed using sutures or clips. The pressure of the viscera against the peritoneum returns the peritoneum into contact with the overlying layer. Over time, the peritoneum reattaches to the overlying layer.

In a second embodiment of a one-component apparatus according to U.S. Ser. No. 07/911,714, the introducing device is an outer elongated tube, and the insufflating device comprises an inner elongated tube mounted in the bore of the outer tube. The proximal ends of the tubes are flexibly coupled together. One end of the main envelope is everted with respect to the other, and is attached to the distal end of the outer elongated tube. The other end of the main envelope is attached to the distal end of the inner elongated tube. The main inflatable chamber defined by the main envelope is thus substantially toroidal. The outer elongated tube has an anchor flange slidably mounted on it. The anchor flange and the main inflatable chamber together form a gas-tight seal with the second layer of tissue.

Such second embodiment of a one-component apparatus is shown in FIGS. 7A–7B and 8A–8B. In this embodiment, a substantially toroidal shape of the main chamber avoids the need to detach and remove the main envelope at the end of the separation process, and the toroidal main chamber provides both the separating function of the main chamber and the sealing function of the toroidal chamber of the embodiment of FIGS. 4A–4C.

The apparatus of FIGS. 7A and 7B comprises tube assembly 260, including outer tube 237 to which is attached a twin port assembly 225 comprising first port 226 and second port 228. The first port is provided with a first flapper valve 202, including flapper valve seat 204. The second port is provided with a second flapper valve 206, including flapper valve seat 208. Each flapper valve seat forms a gas-tight seal with an instrument passed through it.

Tube assembly 260 also includes inner tube 235. Inner tube 235 is shorter than outer tube 237. The proximal end 210 of the inner tube is flexibly attached to the proximal end 222 of outer tube 237 and to first port 226. The flexible attachment enables the distal end 214 of the inner tube to move in the direction shown by the arrow 216. The first port communicates with the bore of inner tube 235, and the second port communicates with the bore of outer tube 237.

Insufflation valve 285 communicates with first port 226, and the bore of inner tube 235. Main chamber inflation valve 231 communicates with second port 228, and the bore of outer tube 237.

Main envelope 212 defines the main inflatable chamber 213 and comprises a cylindrical piece of an elastomeric material such a latex, silicone rubber, or polyurethane. The apparatus is shown with its main envelope in its collapsed state in FIG. 7B, in which the structure of the main envelope can also be seen. The main envelope preferably has a diameter smaller than the outside diameter of the inner tube. One end 230 of the main envelope is attached to distal end 214 of inner tube 235 by means of a suitable adhesive, such as an epoxy or cyanoacrylate adhesive. The other end 232 of the main envelope is everted (i.e., turned back on itself to bring the inside surface 234 of the main envelope to the outside) and attached to the distal end 236 of the outer tube using the same type of adhesive. The main envelope is preferably attached to the outer surfaces of the inner tube and the outer tube.

FIG. 7A shows main envelope 212 in its expanded state. To reach this state, a source of inflation gas is connected to valve 231 and the gas flows into the main inflatable chamber through the bore of outer tube 237. The pressure acting on surface 238 of the main envelope 212 causes the main envelope to assume the toroidal shape shown in FIG. 7A to define toroidal main chamber 213, with surface 234 defining the "hole" or "bore" through the toroidal main envelope. FIGS. 7A and 7B show the correspondence between the surfaces 234 and 238 of the main envelope when the main envelope is in a collapsed state (FIG. 7B) and in an expanded state (FIG. 7A).

Anchor flange 255 is slidably mounted on tube assembly 260, and can be locked in a desired position along the length of the tube assembly. Anchor flange 255 is identical or similar to anchor flange 55 (of FIG. 2A) and thus will not be described further.

Figure 8A:
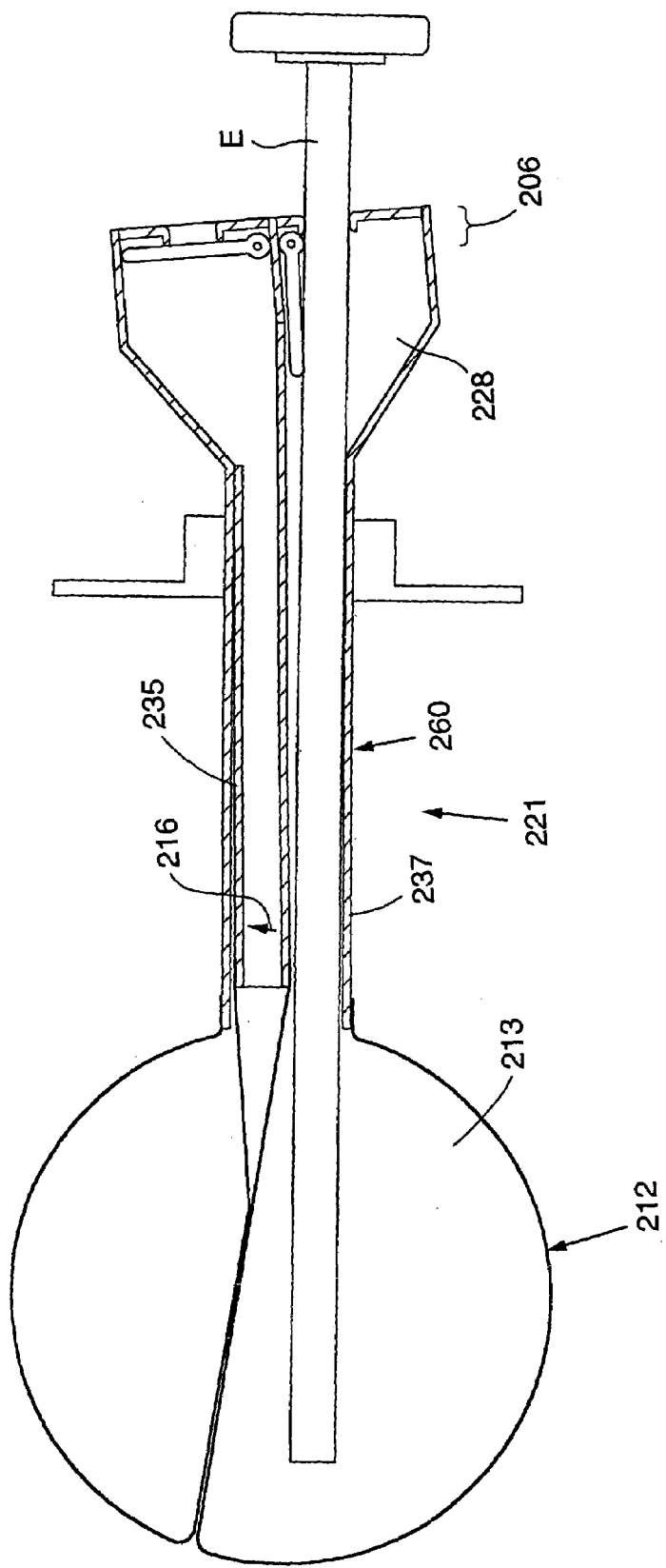
FIG. 8A shows the second one-component apparatus with the main envelope in its expanded state and an endoscope passed through the bore of the outer tube into the main inflatable chamber.

FIG. 8A shows an endoscope E passed through second flapper valve 206, second port 228, and the bore of outer tube 237 into main inflatable chamber 213. The flexible mounting of inner tube 235 in the outer tube enables the endoscope to displace inner tube 235 in direction of the arrow 216 to gain access to the main inflatable chamber. The endoscope is inserted through the second port into the main inflatable chamber during tissue separation using the apparatus to observe the extent of the separation.

FIG. 8B shows an endoscope E passed through first flapper valve 202, first port 226, the bore of inner tube 235, and bore 234 of main envelope 212. The distal part of the endoscope emerges from the bore of the main envelope 212, and can be advanced beyond the main inflatable chamber 213 to observe tissue such as the site of the hernia more closely. The endoscope is inserted through the first port, the inner tube, and the bore of the main envelope during insufflation using the apparatus. Instruments other than endoscopes can also be passed to the site of the hernia through the first flapper valve, the first port, the inner tube, and the bore of the main envelope if desired.

As shown in FIG. 8B, main envelope 212 is in a partially collapsed state that it preferably assumes during the insufflation phase of the procedure. During this part of the procedure, the partially collapsed main inflatable chamber and anchor flange 255 together provide a gas-tight seal to prevent the leakage of insufflation gas. Alternatively, insufflation can be carried out with the main inflatable chamber in a fully expanded state.

In a method described in U.S. Ser. No. 07/911,714 of using the embodiment of FIGS. 7A, 7B, 8A, and 8B to separate a first layer of tissue from a second layer of tissue, the outer elongated tube pushes the main envelope in a collapsed state through an incision through the second layer of tissue to place the main envelope between the first layer of tissue and the second layer of tissue. The main envelope is then inflated to gently separate the first layer of tissue from the second layer of tissue, and to create a working space between the layers of tissue. An endoscope may be passed through the outer elongated tube into the main chamber to observe the extent of separation of the layers of tissue. The anchor flange is slid distally along the introducing device tube to compress the second layer of tissue between it and the main inflatable chamber, to form a gas-tight seal. Insufflating gas is then passed through the bore of the inner elongated tube and the bore of the main envelope into the working space to maintain the separation of the first layer of tissue from the second. An endoscope may be passed through the bore of the inner elongated tube and the bore of the main envelope into the working space to observe within the working space.

More specifically, in performing this method, an incision about 12–15 mm long is made in the abdominal wall, and carried through the abdominal wall as far as, and including, the properitoneal fat layer. The distal end of tube assembly 260 is then inserted into the incision into contact with the peritoneum. Additional gentle pressure detaches the part of the peritoneum in the immediate vicinity of the incision from the overlying layer (at this time, main envelope 212 is inverted within the bore of the tube assembly). A source of inflation fluid is then connected to valve 231. A gas, preferably air, is the preferred inflation fluid, but other gases, such a carbon dioxide can be used. A liquid such as saline solution can be used, but a gas is preferred to a liquid because liquids change the optical properties of any endoscope inserted into the inflatable chamber. The flow of inflation fluid is turned on, which ejects the main envelope 212 from the bore of tube assembly 260.

The inflation fluid progressively expands main envelope 212, and hence main inflatable chamber 213 defined by the main envelope, into an expanded state. The main envelope expands between the peritoneum and the properitoneal fat layer, and gently and progressively separates an increasing area of the peritoneum from the overlying layer as it expands. When the main envelope is in its expanded state, the main inflatable chamber is preferably about 4"–6" (100–150 mm) in diameter.

Early in the process of expanding main envelope 212, an endoscope is inserted into first flapper valve 202. The endoscope is passed through the bore of outer tube 237 into main inflatable chamber 213. Once partially expanded, main envelope 212 is sufficiently transparent for the extent of the separation of the peritoneum to be observed using the endoscope.

When a sufficient area of the peritoneum is separated, the supply of inflation fluid is turned off and the endoscope is removed from main inflatable chamber 213. Valve 231 is then opened to allow inflation fluid to vent partially from main inflatable chamber 213 (allowing main envelope 212 to return at least partially to its collapsed state). Alternatively, main envelope 212 may be kept fully expanded.

Anchor flange 255 is then advanced along tube assembly 260 to bring the anchor flange into contact with the skin of the abdominal wall. Tube assembly 260 is then gripped, and the anchor flange is further advanced slightly. This forces the main envelope 212 into contact with the overlying layer, and slightly compresses the abdominal wall, including the overlying layer but excluding the peritoneum, between the main envelope and the anchor flange. Once adjusted, anchor flange 255 is locked in position on the tube assembly, and main envelope 212 forms a gas-tight seal with the abdominal wall and the peritoneum.

A suitable source of insufflation gas is attached to second valve 285, and insufflation gas is passed through the bore of inner tube 235, and bore 234 of main envelope 212, into the working space between the peritoneum and the overlying layer. The pressure of the insufflation gas re-separates the peritoneum from the overlying layer, and provides a larger working space in which repair of the hernia can be carried out.

An instrument such as an endoscope can be passed through second flapper valve 206, the bore of inner tube 235, and bore 234 of main envelope 212, into the working space to perform a repair procedure. When no instrument is so inserted, insufflation pressure is maintained by second flapper valve 206.

After the treatment procedure is completed, valve 285 is operated to release the insufflation gas from the working space. Valve 231 is operated to release the inflation fluid from main inflatable chamber 213, which releases compression from the abdominal wall, excluding the peritoneum. Main envelope 212 returns to its collapsed state inside the bore of outer tube 237.

The tube assembly is then withdrawn from the incision, and the incision is closed using sutures or clips. The pressure of the viscera against the peritoneum returns the peritoneum into contact with the overlying layer. Over time, the peritoneum reattaches to the overlying layer.

In another method described in U.S. Ser. No. 07/911,714, access is provided through the abdominal wall from near the umbilicus to repair a hernia. This method will be described with reference to FIGS. 9A–9I. This method is often preferable to the hernia repair methods described above in which the incision is placed close to the site of the hernia, since in practice, it is preferred to make the incision at or near the umbilicus because the boundary between the peritoneum and the properitoneal fat layer can be more directly accessed near the umbilicus. The midline location of the umbilicus is devoid of muscle layers that would otherwise need to be traversed to reach the properitoneal fat layer.

In the method of FIGS. 9A–9I, the main envelope is partially expanded, collapsed, and advanced toward the site of the hernia. This sequence is repeated to progressively separate the peritoneum from the overlying layer and form the tunnel from the umbilicus to the site of the hernia. Then, at or near the site of the hernia, the main envelope is fully expanded to provide the working space at the site of the hernia. The working space is then insufflated to maintain the separation of the peritoneum from the overlying layer. The method of FIGS. 9A–9I can be practiced using any of the two-component or one-component apparatuses described above. For specificity, the method will be described with reference to a two-component apparatus.

Figure 9A:
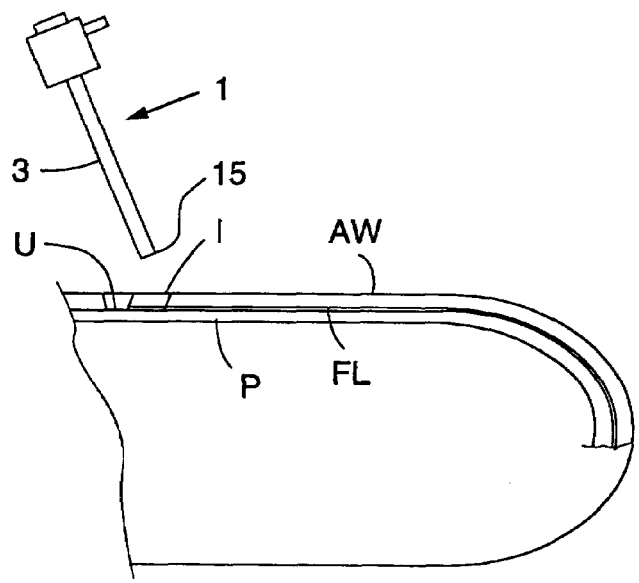
FIGS. 9A–9I show an alternative method of using either a one-component or two-component apparatus to separate the peritoneum from the overlying layer near the groin, with the apparatus inserted through an incision near the umbilicus.

An incision about 12–15 mm long is made in the abdominal wall AW, and is carried through the abdominal wall as far as, and including, the properitoneal fat layer FL. The incision is made at the umbilicus U, as shown in FIG. 9A.

Figure 9B:
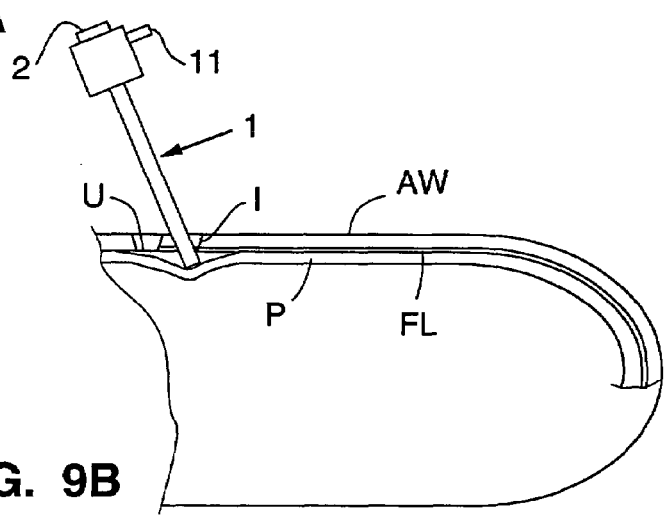

Distal end 15 of introducer tube 3 of separation component 1 is then inserted into the incision to bring the distal end into contact with the peritoneum P. Additional gentle pressure detaches the part of the peritoneum in the immediate vicinity of the incision from the overlying layer, as shown in FIG. 9B. In FIG. 9B, the peritoneum is shown detached from the properitoneal fat layer FL. Main envelope 12 cannot be seen in FIGS. 9A and 9B because it is inverted within the bore of introducer tube 3.

Figure 9C:
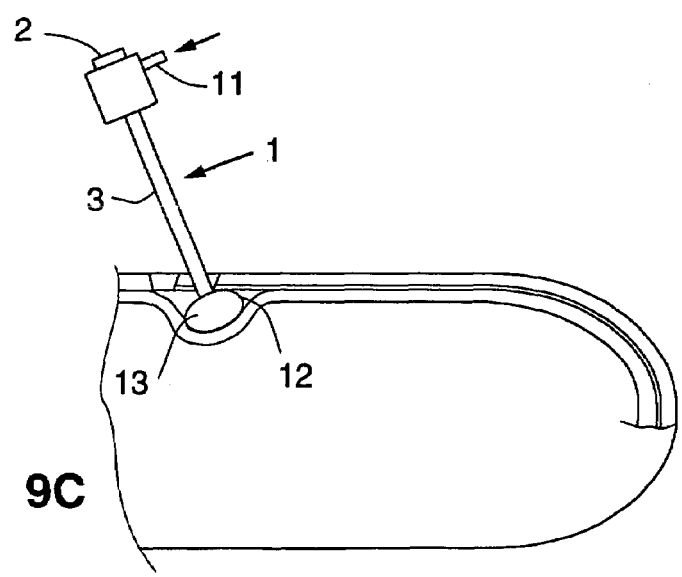

A source of a suitable inflation fluid (not shown), as previously described, is connected to valve 11. The flow of inflation fluid is turned on, which ejects main envelope 12 of main inflatable chamber 13 from the bore of introducer tube 3. The inflation fluid progressively expands main envelope 12, and hence main inflatable chamber 13 defined by the main envelope, into a partially-expanded state, as shown in FIG. 9C. The main envelope expands between the peritoneum and the properitoneal fat layer FL, and gently and progressively detaches an increasing area of the peritoneum P from the overlying layer near the umbilicus as it expands.

An endoscope (not shown) can be inserted into main inflatable chamber 13 through flapper valve 2 and the bore of introducer tube 3. The endoscope can be used to observe the extent of the separation of the peritoneum, as described above.

Figure 9D:
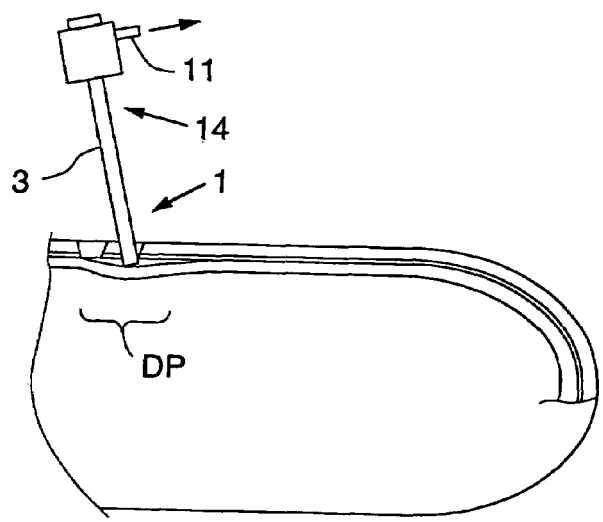

When main envelope 12 expanded such that the main inflatable chamber 13 is about one-fourth of its fully-expanded diameter, i.e., about 1.0"–1.5" (25–37 mm) in diameter, the supply of inflation fluid is turned off. Valve 11 is then operated to vent inflation fluid from the main inflatable chamber 13. The main envelope progressively returns to its collapsed state, as shown in FIG. 9D. The peritoneum portion DP that was separated by the main inflatable chamber remains detached from the overlying layer, as shown. Alternatively, the main envelope can be inflated to a fully-expanded state.

Figure 9E:
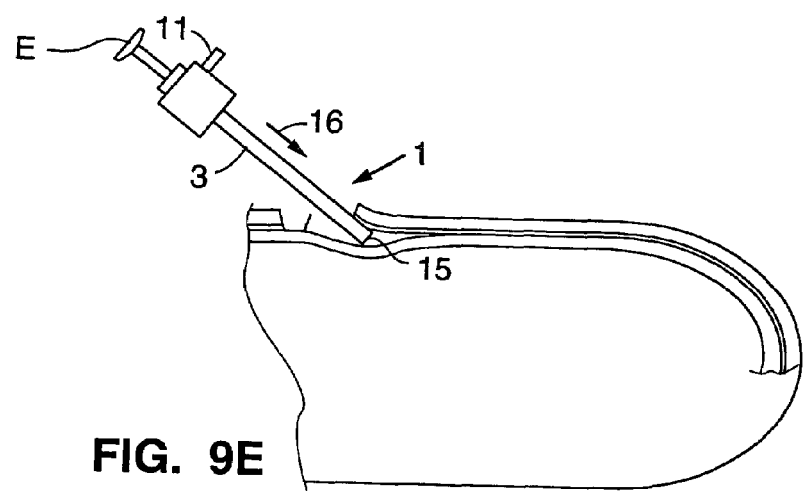

Separation component 1, including the collapsed main envelope 12, is then manipulated in the direction indicated by arrow 14, and then in the direction indicated by arrow 16, to advance distal part 15 of introducer tube 3 to the limit of the detached part DP of the peritoneum in the direction of the groin, as shown in FIG. 9E. An endoscope E inserted through flapper valve 2 into the bore of introducer tube 3 enables the position of the distal part 15 relative to the detached part DP of the peritoneum to be observed.

Figure 9F:
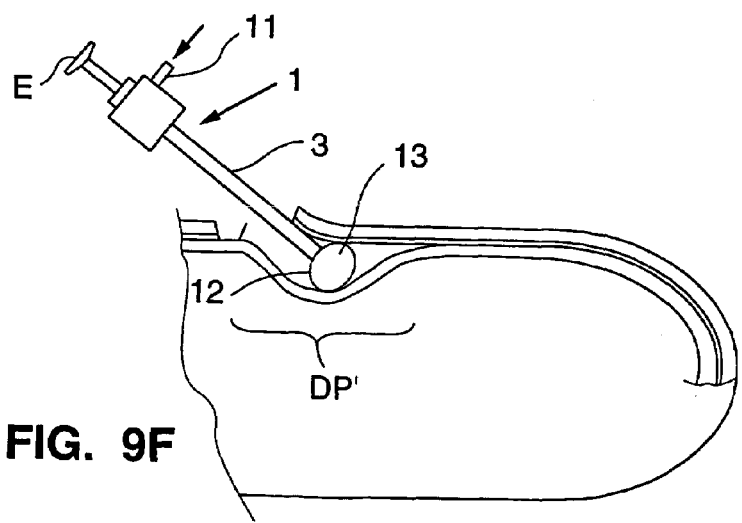

Once distal part 15 of the introducer tube has been positioned, the separation component 1 is clamped in position, or is gripped, and inflation fluid is once more passed through the valve 11 and the bore of introducer tube 3 into main inflatable chamber 13. The main envelope 12 expands once more, increasing the extent of the detached part of the peritoneum towards the groin, as shown in FIG. 9F. The increased extent of the detached part of the peritoneum is indicated by line DP' in FIG. 9F. The extent of the detached part of the peritoneum is increased in the direction from the umbilicus to the groin, but not in the direction transverse to this direction. Endoscope E is used to observe the extent of the separation.

Figure 9G:
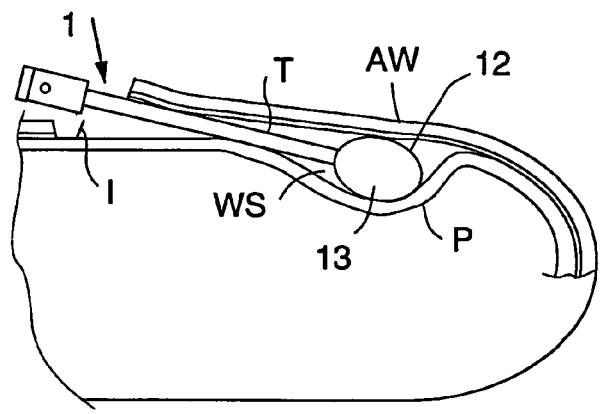
Figure 9H:
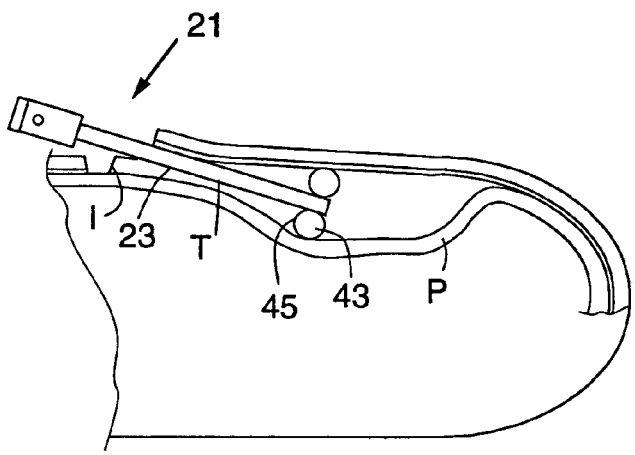

The process of collapsing the main envelope 12, advancing the distal part 15 of the introducer tube to the limit of the detached part DP' of the peritoneum in the direction of the groin, holding the introducer tube in position, and partially re-inflating main envelope 12, is repeated until the detached part of the peritoneum includes the peritoneum over the site of the hernia. This process provides a tunnel T between the incision at the umbilicus and the site of the hernia (as shown in FIGS. 9G, 9H, and 9I).

When the main envelope is in the vicinity of the site of the hernia H, main envelope 12 is fully inflated to form a working space WS including the site of the hernia. This is shown in FIG. 9G.

The working space at the site of the hernia is then insufflated. With the two-component apparatus, inflation fluid is vented from the main inflatable chamber 13 to collapse main envelope 12, and the separation component 1 is withdrawn from tunnel T through incision I. Insufflation component 21 is introduced into the incision, and advanced through the tunnel until envelope 45 of toroidal inflatable chamber 43 lies within the working space WS, clear of the tunnel. Toroidal inflatable chamber 43 is inflated, the anchor flange is clamped in position, and insufflation gas is passed into the working space, as shown in FIG. 9H. Toroidal inflatable chamber 43 provides a gas-tight seal with the entrance of the tunnel.

Figure 9I:
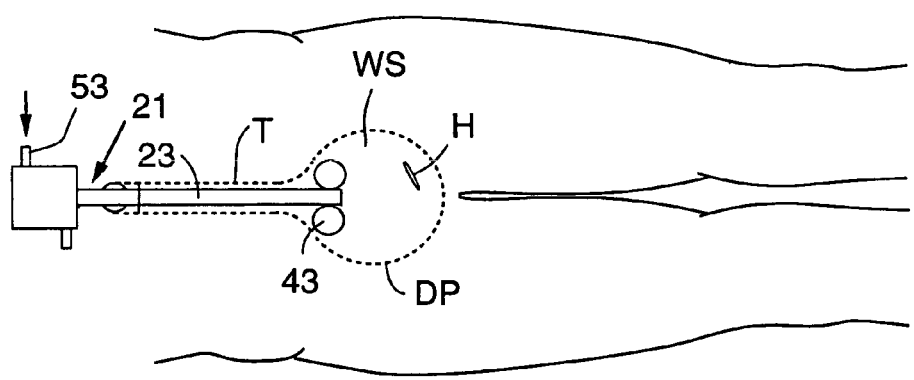

FIG. 9I is a plan view of the abdomen with insufflation component 21 in place. The anchor flange has been omitted for clarity. Toroidal inflatable chamber 43 provides a gas-tight seal with the entrance of tunnel T. The extent of the separated peritoneum is indicated by dotted line DP. It can be seen that the lateral extent of the separated peritoneum is considerably greater in working space WS than in tunnel T.

At this stage, if a one-component apparatus had been used (with the main inflatable chamber remaining in the working space), inflation fluid would be vented from the main inflatable chamber to collapse the main envelope, and the main envelope would be withdrawn from the working space through the bore of the tube assembly. The tube assembly would be partially withdrawn until the envelope of a toroidal inflatable chamber 43 lies within the working space, clear of the entrance to the tunnel. The toroidal inflatable chamber 43 would then be inflated, the anchor flange clamped in position, and insufflation gas passed into the working space, as already described. The toroidal inflatable chamber 43 would seal against the entrance from the tunnel into the working space.

Alternatively, if another type of one-component apparatus had been used (with the main inflatable chamber remaining in the working space), the main envelope would preferably be returned to a partially collapsed state, and the tube assembly partially withdrawn until the main inflatable chamber lies within the working space, adjacent to the entrance of the tunnel. The anchor flange would be clamped in position, and insufflation gas is passed into the working space as already described. The partially-collapsed main chamber would seal against the entrance from the tunnel into the working space.

Regardless of the embodiment of the apparatus used to create the insufflated working space WS shown in FIG. 9I, the hernia is then repaired using a procedure such as that described in connection with FIG. 3I.

Before either component 1 or component 21 (or a one-component apparatus that performs the functions of both components 1 and 21) is inserted into the patient, its inflatable envelopes and chambers are deflated and packed into a sheath. One method of packing an inflatable chamber in its deflated, compact state is to roll the chamber inwardly from opposing lateral sides.

Above-referenced U.S. Ser. No. 08/405,284 discloses a device which performs both dissection and retraction of tissue layers while at least a part of the device remains in the patient throughout the dissection and retraction procedure, so that the user need not remove one assembly from the patient and then insert a second assembly into the patient (searching for the dissected spatial plane in order to deploy the second assembly in the proper position) between the dissection and retraction steps. In a preferred implementation, the distal end of the device is moved to a position between tissue layers in the patient. A first balloon is then inflated between the tissue layers to dissect the tissue layers. A second balloon, which is used to retract the tissue layers, is then inflated between the tissue layers. The distal end of the device for introducing and inflating first balloon remains in the patient until the second balloon has been inflated, so that the tissue layers remain at least partially separated at all times after initial introduction of the device between such layers. After retracting the tissue layers with the second balloon, the first balloon is deflated, e.g., by a puncturing step which creates an opening in the first balloon. Instruments are then introduced into a working space through the opening in the first balloon. The second balloon, which can be positioned in the interior of the first balloon, is inflated to seal the working space so that insufflating fluid is impeded from escaping.

A preferred embodiment of the inventive one-component apparatus (identified by reference numeral 600) for tissue dissection and instrument anchoring, and also tissue retraction, will be described with reference to FIGS. 10, 11, 12, 13, and 14.

Figure 10:
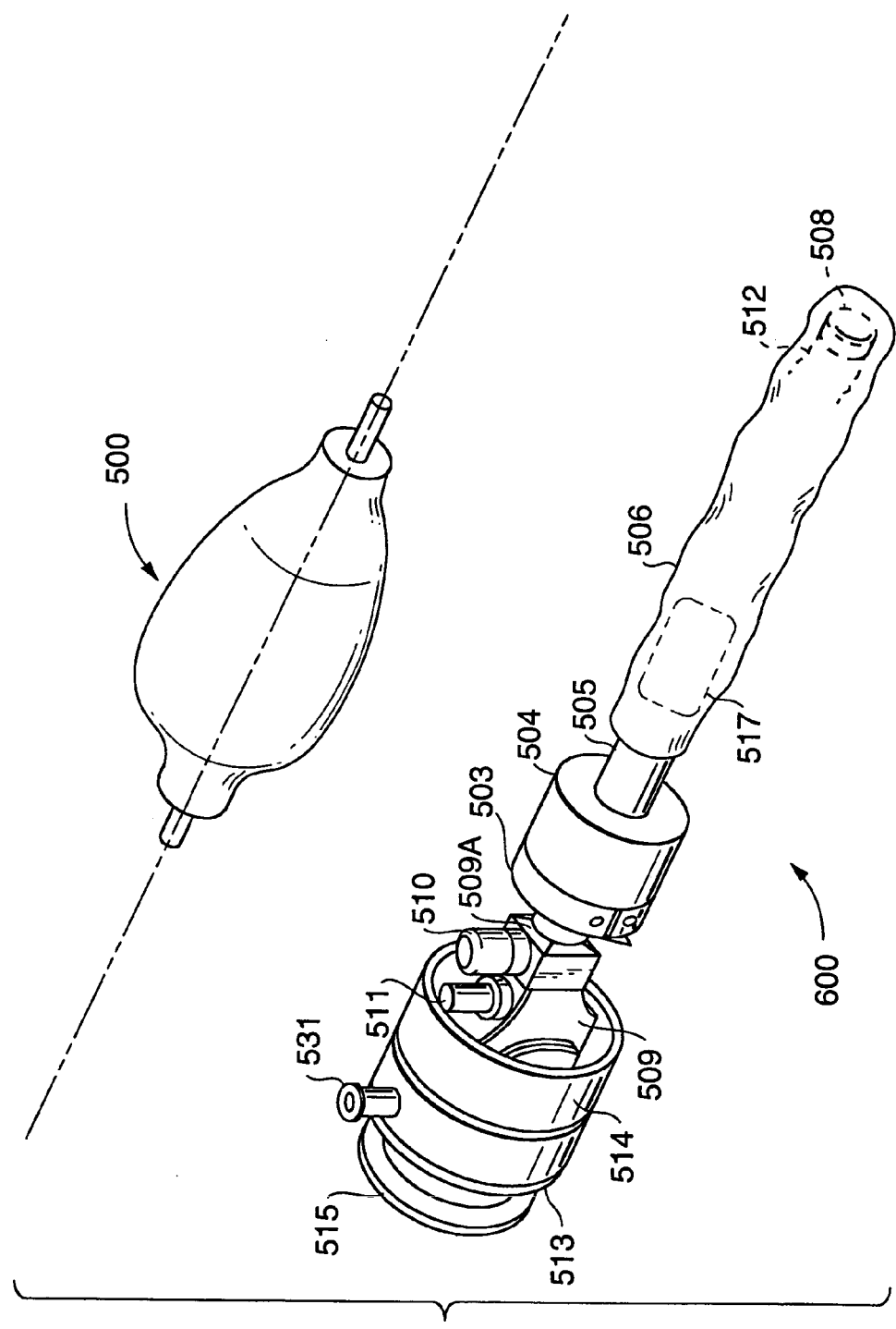
FIG. 10 is a perspective view of a preferred embodiment of the inventive one-component apparatus for tissue dissection, tissue retraction, and instrument anchoring.
Figure 11:
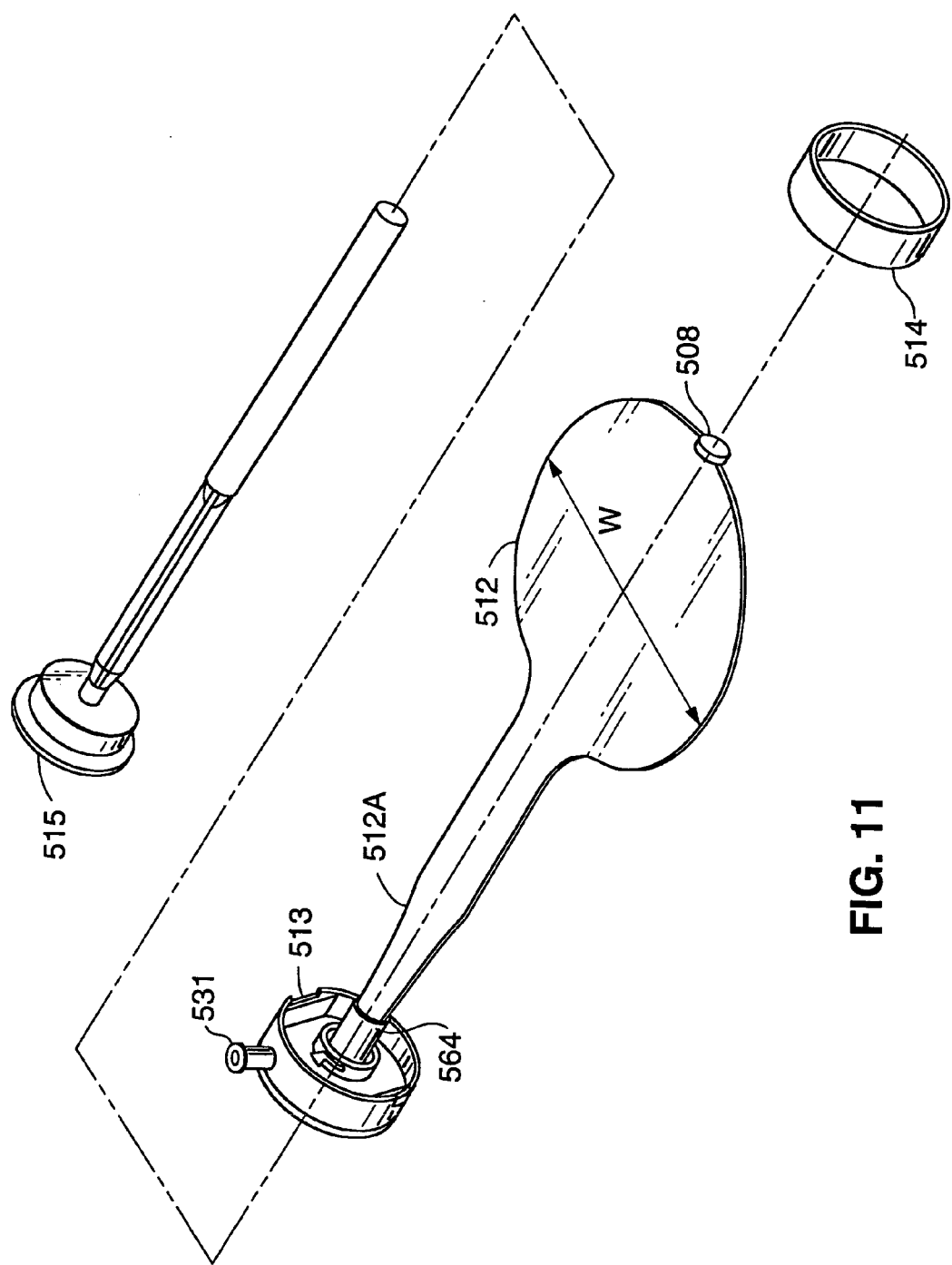
FIG. 11 is an exploded view of obturator 515, retaining ring 514, and the dissection balloon subassembly of the FIG. 10 apparatus.
Figure 12:
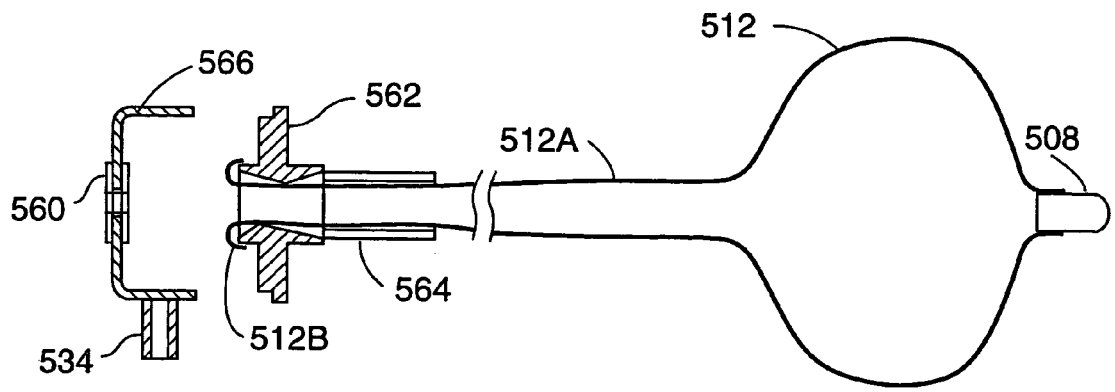
FIG. 12 is an exploded cross-sectional view of the dissection balloon subassembly of the FIG. 10 apparatus.
Figure 19:
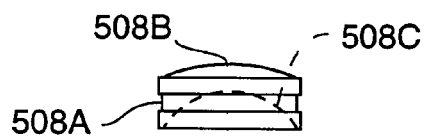
FIG. 19 is a side elevational view of a balloon window for use as window 508 of the FIG. 10 apparatus.
Figure 20:
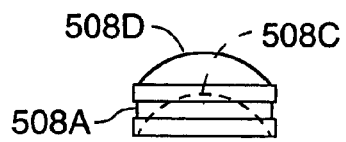
FIG. 20 is a side elevational view of another balloon window for use as window 508 of the FIG. 10 apparatus.
Figure 21:
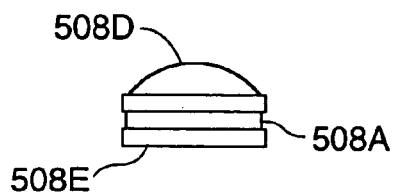
FIG. 21 is a side elevational view of a third balloon window for use as window 508 of the FIG. 10 apparatus.
Figure 13:
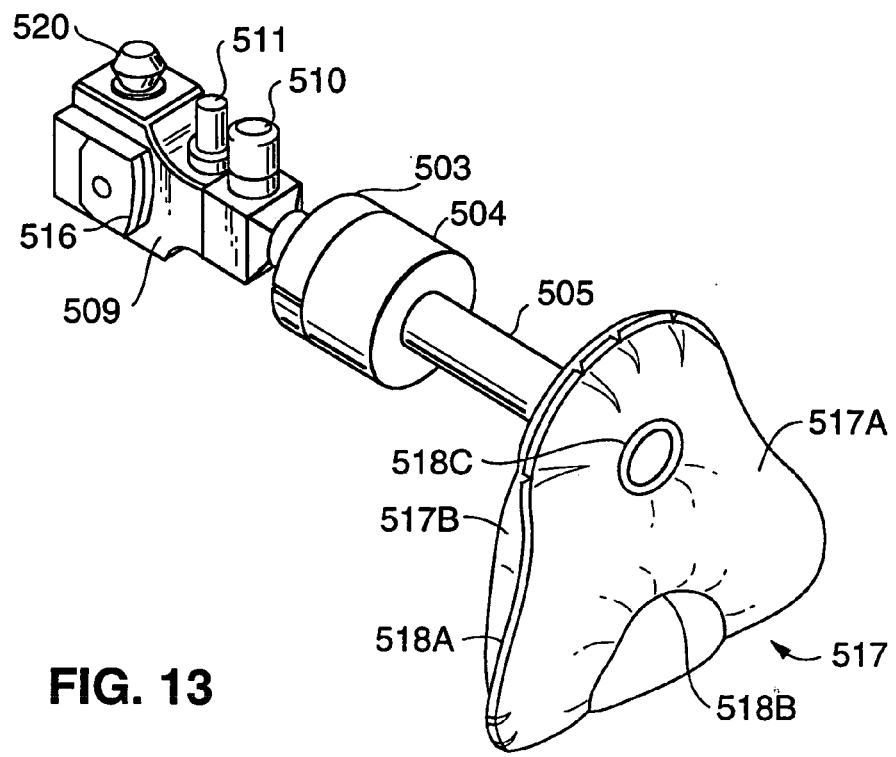
FIG. 13 is a perspective view of the tissue retraction and instrument anchoring subassembly of the FIG. 10 apparatus.
Figure 14:
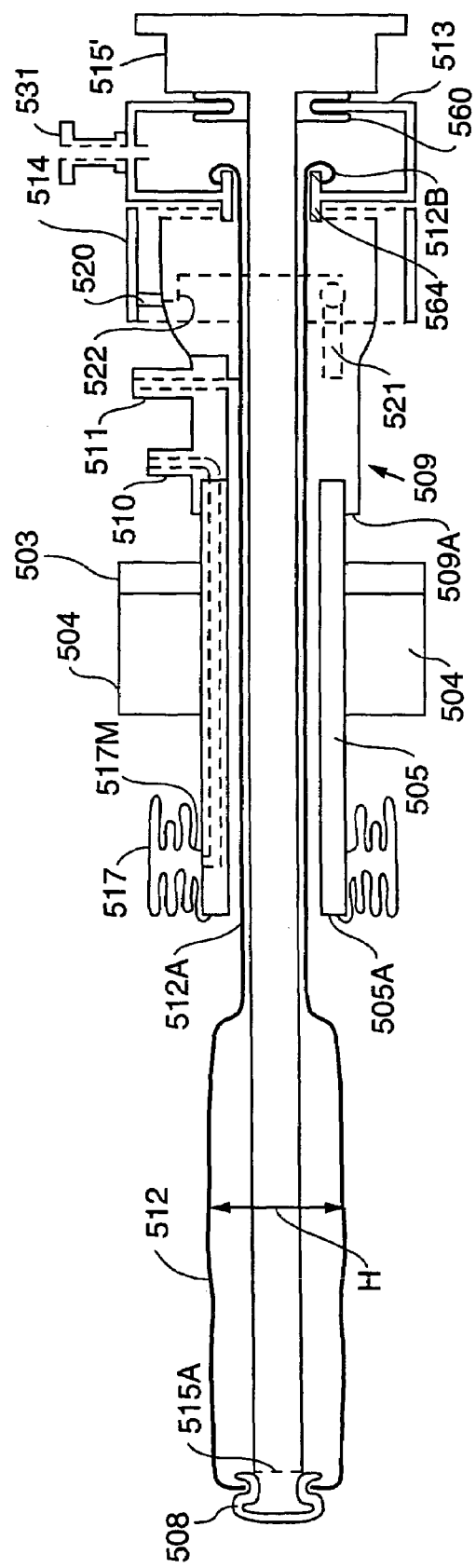
FIG. 14 is a partially side elevational, partially side cross-sectional view of the FIG. 10 apparatus (with balloon 512 inflated and endoscope 515' substituted for obturator 515).

FIG. 10 is a perspective view of apparatus 600. FIG. 14 is a partially side elevational, partially side cross-sectional view of apparatus 600. FIGS. 11, 12, 13, 16, 17, 18, 19, 20, and 21 are views of portions (or substitutes for portions) of apparatus 600. FIG. 11 is an exploded view of obturator 515, retaining ring 514, and the dissection balloon subassembly of apparatus 600. FIG. 12 is an exploded cross-sectional view of the dissection balloon subassembly of apparatus 600. Each of FIGS. 19, 20, and 21 is a side elevational view of a balloon window for use as window 508 of apparatus 600. FIG. 13 is a perspective view of the tissue retraction and instrument anchoring subassembly of apparatus 600.

Figure 15:
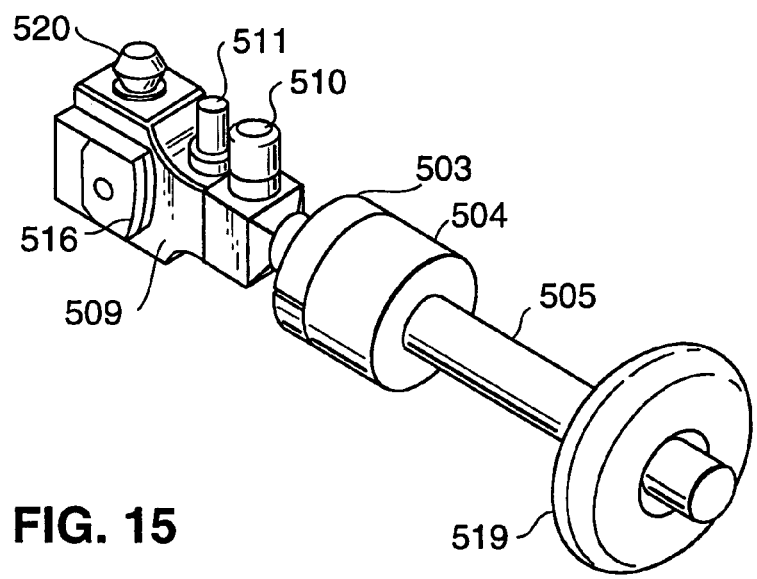
FIG. 15 is a perspective view of an alternative instrument anchoring subassembly, for use in the FIG. 10 apparatus as a substitute for the FIG. 13 subassembly.

The assembly of FIG. 15 is an alternative anchor balloon assembly which can be substituted for that of FIG. 13 in apparatus 600 of FIGS. 10, 11, 12, and 14.

With reference to FIG. 10, apparatus 600 includes housing 509, cannula 505 (connected to housing 509 and extending out from distal face 509A of housing 509), retaining ring 514 (around housing 509), clamp 503 (around cannula 505), foam collar 504 (around cannula 505, and attached to clamp 503 so that clamp 503 and collar 504 can slide together as a unit along cannula 505 until clamp 503 locked in a fixed position along cannula 505), housing 513, dissection balloon 512 having a long neck 512A (shown in FIG. 11) whose free end is attached to housing 513 and which extends through cannula 505, anchor balloon 517 attached to cannula 505 (near distal end 505A of cannula 505 as shown in FIG. 14), sheath 506 which encloses balloons 517 and 512, and obturator 515 (extending through housing 513, housing 509, and cannula 505 into the interior of balloon 512).

Flapper valve 521 is mounted within housing 509, and a biasing spring (not shown) biases valve 521 in a closed position (not shown in FIG. 14) in which valve 521 rests against an elastomeric seal around an end port in the proximal face of housing 509 (the face at the right end of housing 509 in FIG. 14) thus sealing the port. When button 520 is depressed (such as by ring 514 fitted around housing 509), mechanical linkage 522 (connected between button 520 and valve 521) holds valve 521 in the open position shown in FIG. 14, in which obturator 515 (or a similarly shaped endoscope or other instrument) is free to pass into the port through the proximal face of housing 509, and through the central channel extending through housing 509. When button 520 is released (such as when ring 514 is removed), linkage 522 allows spring-biased valve 521 to return to its normally closed position sealing the port in the proximal face of housing 509. The seat of flapper valve 521 (around the end port in the proximal face of housing 509) preferably forms a gas-tight seal with obturator 515 (or an endoscope or other instrument) inserted though the end port and into cannula 505.

During use of the apparatus, after balloon 512 has been inflated (with obturator 515 or another instrument inserted through the end port in the proximal face of housing 509 and into cannula 505), balloon 512 can be deflated as follows. The obturator (or other instrument) is withdrawn through the end port in the proximal face of housing 509 while button 520 remains depressed (e.g., while ring 514 remains in place over button 520), thus allowing the inflating fluid to escape past the open flapper valve 521 out the end port in the proximal face of housing 509. Any remaining inflating fluid within balloon 512 can be pumped out using a deflation bulb (or other pump) positioned against port 531 (port 531 can include a valve, or it can simply be an open port which accepts a hand bulb or syringe), or any such remaining inflating fluid can be forced out by compressing balloon 512.

With housing 513 detached from the proximal face of housing 509, it is sometimes useful to mount a converter in the end port in the proximal face of housing 509, to maintain a fluid seal when an instrument is inserted through the converter (and through the end port) into cannula 505. By using differently sized and shaped converters, instruments of different sizes and shapes can be introduced into cannula 505. When performing a procedure in an insufflated working space in the patient using such an instrument, use of a converter of an appropriate size and shape may be needed to prevent undesired deflation of the working space due to undesired leakage of insufflation gas through the end port in the proximal face of housing 509 around the instrument (if the outer diameter of the instrument is less than the diameter of the end port).

Mouth 512B of dissection balloon 512 is attached (preferably by glue) to tube portion 564 of housing 513, as shown in FIGS. 14 and 12. With reference to FIG. 14, the apparatus is preferably assembled by removably attaching the distal face of housing 513 (the left face in FIG. 14) to the proximal face of housing 509 (such as by snap fitting or bayonet fitting means). Elongated neck 512A of balloon 512 is extended through tube portion 564 of housing 513, through the central channel of housing 509, and through cannula 505. Endoscope 515' is inserted through seal 560 of housing 513, and (within balloon 512) through tube portion 564 of housing 513, the central channel of housing 509, and cannula 505 until the distal end 515A of endoscope 515' abuts window member 508 at the distal end of balloon 512 (as shown in FIG. 14).

In a class of preferred embodiments (to be discussed below), balloon 512 comprises a first sheet of thin elastomeric material (such as polyurethane, latex, or silicone rubber) bonded (e.g., RF-welded) to a second sheet of thin, inelastic (or having relatively low elasticity) material such as polyester, polyethylene, or nylon film. Balloon 512 is preferably formed to have a wide profile when expanded, in the sense that its width (dimension W shown in FIG. 11) when expanded is much greater than its expanded height (dimension H shown in FIG. 14). Another dissection balloon having a different expanded shape can be substituted for balloon 512 in alternative embodiments.

Before the apparatus is first used, balloon 512 is packed against obturator 515 so as to occupy a small volume (as shown in FIG. 10), so that the packed balloon 512 does not significantly impede insertion of obturator 515 into the patient. At an appropriate time during use of the apparatus (e.g., before or during inflation of balloon 512), balloon 512 is expanded (inflated as shown in FIG. 14) to occupy a larger volume. Obturator 515 is withdrawn and replaced by an endoscope (e.g., endoscope 515' of FIG. 14) for viewing the patient through window 508 of balloon 512. Alternatively, before the apparatus is first used, balloon 512 is packed against an endoscope (e.g., endoscope 515') so as to occupy a small volume, so that the packed balloon 512 does not significantly impede insertion of the endoscope into the patient, and allows visualization of anatomy during insertion of the device.

Anchor balloon 517 is attached to cannula 505, near distal end 505A of cannula 505 as shown in FIG. 14. Before the apparatus is first used, balloon 512 is packed against cannula 505 (as shown in FIG. 14) so as to occupy a small volume, so that the packed balloon 517 does not significantly impede insertion of cannula 505 into the patient. Before the apparatus is first inserted into a patient, both packed balloons 512 and 517 are preferably packed into sheath 506 (sheath 506 is shown in FIG. 10, but not in FIG. 14). At an appropriate time during use of the apparatus, balloon 517 is expanded (inflated) to occupy a larger volume (as shown in FIG. 13). Preferably, balloon 517 has a rounded triangular shape when expanded as shown in FIG. 13. In alternative embodiments, another anchor balloon having a different expanded shape (such as toroidal balloon 519 of FIG. 15) can be substituted for balloon 517. As will be described below, balloon 517 is used for retracting tissue layers and for maintaining insufflation fluid in a working space.

When clamp 503 is locked in a position along cannula 505 pressing foam collar 504 against the patient, foam collar 504 helps to immobilize the entire apparatus (including housing 509 and cannula 505) and collar 504 applies a modest compressive force to the tissue between clamp 503 and inflated balloon 517, thereby helping balloon 517 form a seal to limit the escape of insufflation gas during laparoscopic procedures.

Sheath 506 (shown in FIG. 10) is preferably perforated but may be formed in any other manner permitting easy opening. Inflation of balloon 512 tears a perforated sheath 506 along the perforation and releases both balloon 512 and balloon 517. Alternatively, sheath 506 may include an independent opening mechanism, such as a removable thread which binds the sheath together, and which can be opened by the operator at a desired time.

Inflation port 531 of housing 513 is used for inflating and deflating balloon 512. Port 531 is opened by inserting an inflation device, such as bulb 500 of FIG. 10, into it. When opened, port 531 provides a path for inflating balloon 512 by pumping gas (or other fluid) through mouth 512B of balloon 512 into the interior of balloon 512, and for deflating balloon 512 by allowing inflation fluid to escape from balloon 512 out through port 531. A conventional hand bulb 500 or a syringe can be used to inject the fluid through port 531 (or through valves 510 and 511 to be discussed below). Alternatively, port 531 can be a continually open port that accepts a hand bulb or syringe.

Inflation valve 510 of housing 513 is used for inflating and deflating anchor balloon 517. Valve 510 is opened by inserting an inflation device, such as bulb 500 of FIG. 10, into it. When opened, valve 510 provides a path for inflating balloon 517 by pumping gas (or other fluid) through cannula 505 through mouth 517M of balloon 517 into the interior of balloon 517, and for deflating balloon 517 by allowing inflation fluid to escape out from mouth 517M of balloon 517 and then out through valve 510.

Insufflation valve 511 is used to supply insufflation gas or liquid into a working space within the patient. Valve 511 is typically used when obturator 515 (or endoscope 515'), the dissection balloon assembly comprising balloon 512 and housing 513, and ring 514 have been removed from the remaining portion (the tissue retraction and instrument anchoring subassembly) of the FIG. 10 apparatus (and valve 521 has been closed, and the anchoring assembly comprising collar 504 and clamp 503 has been locked to anchor the remaining portion of the apparatus to the patient). Valve 511 is opened by inserting an inflation device into it. When opened, valve 511 provides a path for insufflation fluid to flow through the channel surrounded by cannula 505 into the working space (sealed by expanded balloon 517 and the clamp assembly 503, 504) and provides a path for allowing insufflation fluid to escape out from the working space through valve 511.

We next describe a preferred structure of the dissection balloon assembly in more detail with reference to FIG. 12. To assemble this assembly, mouth 512B of balloon 512 is glued to a cylindrical rim on the left face of base 562 (as shown in FIG. 12) of housing 513. Tube 564 is glued to a cylindrical rim on the opposite face of base 562, and the neck 512A of balloon 512 is pulled to the right through base 562 and tube 564 into the configuration shown in FIG. 12. Then, cover 566 is glued to base 562 to form housing 513. Thus, when inflation port 531 of cover 566 is opened, inflation fluid can be pumped through port 531 and the volume enclosed by housing 513 into mouth 512B of balloon 512. Main seal 560 is glued around the central orifice through cover 566, to provide a fluid seal preventing fluid from escaping out through this orifice when an obturator or other rod-shaped instrument is inserted through the orifice into the interior of balloon 512. Typically, the assembled FIG. 10 apparatus is packaged with an obturator such as obturator 515 extending through seal 560 into the interior of balloon 512. At various times during use of the apparatus, the obturator is removed and replaced by an endoscope (e.g., endoscope 515' of FIG. 14) having the same or similar outer dimensions. Seal 560 is preferably made of rubber or another elastomer.

Next, with reference to FIGS. 13 and 14, we describe a preferred structure of the anchoring and tissue retraction assembly including housing 509 and balloon 517. In some implementations, a converter door 516 (made of rigid plastic) is slidably mounted to the outside of housing 509. In the position shown in FIG. 13, door 516 covers a port (not shown) through the side wall of housing 509. Door 516 can be slid proximally (away from balloon 517) to uncover this port. The port is normally sealed by a closed second flapper valve (similar to valve 521 of FIG. 14) within housing 509. In response to depression of button 520, a second mechanical linkage (similar to linkage 522 of FIG. 14) moves the second flapper valve to open the port, so that (when door 516 is open) an instrument can be inserted through the opened port into housing 509 and then through cannula 505 into the working space within the patient. In some implementations, door 516, the port (through the side wall of housing 509) which can be covered by door 516, and the associated valve means for opening and closing the port, are omitted.

In a preferred implementation of the FIG. 10 apparatus, port 531, housing 513 (including cover 566 and base 562), and housing 509 are made of hard plastic (such as that known as ABS plastic), obturator 515 and ring 514 are made of hard plastic (such as polypropylene or ABS plastic), clamp 503, cannula 505, and dissection balloon window 508 (which can be shaped as a lens) are made of polycarbonate, foam collar 504 is made of polyurethane foam, sheath 506 is made of polyurethane, valves 510 and 511 are made of stainless steel and plastic, the flapper valve assembly comprising button 520, link 522, valve 521, and the seat against which valve 521 rests when closed is made of stainless steel, ABS plastic, and silicone rubber, and the converter door assembly comprising door 516 is mode of silicone rubber and polyetherimide.

Any of the balloon cannula systems of referenced U.S. Ser. No. 08/365,096 can be employed in alternative implementation of the present invention, e.g., to provide a supporting portion which extends into the interior of the dissection balloon to provide support for the dissection balloon during inflation.

With reference again to FIG. 13, anchor balloon 517 is substantially bell-shaped, and composed of two sheets (517A and 517B) bonded together (e.g., by RF-welding) at seams 518A, 518B, and 518C. Outer seam 518A defines the outline of a bell-shape, semi-circular seam 518B reduces pressure induced stresses at the periphery of balloon 517 (and eliminates the need to provide baffles), and seam 518C defines a circular throughhole (through which the longitudinal axis of cannula 505 extends, and through which an instrument such as an endoscope can be extended). Outer seam 518A has a semi-circular upper portion which is substantially concentric with a throughhole defined by seam 518C. Sheet 517A has a mouth portion 517M (shown in FIG. 14), and balloon 517 is attached at mouth portion 517M to cannula 505, so that balloon 517 can be inflated and deflated using valve 510. The shape of balloon 517 and the strength and elasticity of its component sheets (and thus the inflating fluid pressure within it during use) are chosen so that inflated balloon 517 (positioned between two dissected tissue layers) not only anchors cannula 505 to the patient but also retracts the dissected tissue layers by a desired amount and alternatively-shaped and structured anchor balloons will be used for alternative uses. Preferably, sheet 517A is an inelastic plastic sheet (e.g., made of polyester) which does not stretch significantly during inflation of balloon 517 (to define the desired inflated structure of the balloon even with inflating fluid pressure within the balloon that is adequate for retracting the tissue layers by the desired amount). Also preferably, sheet 517B is a highly elastic sheet (e.g., made of polyurethane) which does stretch significantly during inflation. In alternative embodiments (to be described), anchor balloon 517 is replaced by another balloon having nonuniform elasticity tailored for the particular intended use in any of the ways discussed below (e.g., the anchor balloon of the invention can comprise two large sheets of relatively low elasticity as does the balloon of FIG. 23, with relatively elastic insert sheets bonded to the large sheets as in FIG. 23).

FIG. 15 is a perspective view of an alternative anchoring subassembly for use in the FIG. 10 apparatus as a substitute for the FIG. 13 subassembly. The FIG. 15 subassembly differs from that of FIG. 13 only in that the former includes toroidal anchor balloon 519 mounted around cannula 505 while the latter includes above-described anchor balloon 517 mounted around cannula 505. Preferably, anchor balloon 519 of FIG. 15 is made of a thin, highly elastic material such as polyurethane or silicon coated latex, and has a mouth portion at which balloon 519 is mounted to cannula 505 (so that balloon 519 can be inflated or deflated using valve 510). When inflated, balloon 519 functions to anchor cannula 505 to the patient, but typically does not retract dissected tissue layers to the degree that inflated balloon 517 would retract the same layers.

We next describe preferred implementations of dissection balloon 512 (and variations thereon) in more detail. FIGS. 16–18 show a first preferred embodiment of balloon 512.

In the embodiment of FIGS. 16–18, balloon 512 includes: first and second sheets 513A and 513B attached together at seam 512C such as by RF (radio frequency) welding; and neck reinforcing sheet 513C attached to sheet 513A (such as by RF welding) at neck 512A of balloon 512. Preferably, sheets 513A and 513B are polyurethane sheets of 0.002 inch thickness (each having high elasticity so that it stretches substantially during inflation) and sheet 513C is made of material having low elasticity (e.g., polyester film, or a multilayer film commercially available from Rexham comprising polyurethane and polyester layers) so that it does not stretch significantly during inflation. This preferred embodiment (with window 508 attached to its distal end), when inflated, has the appearance shown in FIGS. 18C and 18D, where FIG. 18C is an elevational view of the distal end of the inflated balloon and FIG. 18D is a side elevational view of the distal end of the inflated balloon.

Figure 18A:
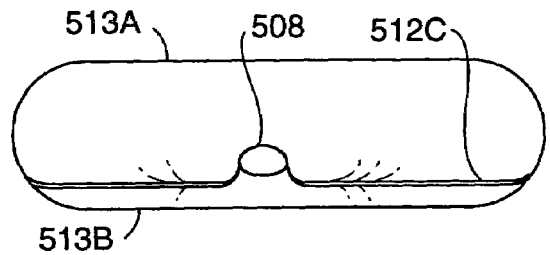
FIG. 18A is an end view of an alternative implementation of the dissection balloon of FIG. 16, when inflated, and with a window attached at its distal end.
Figure 18B:
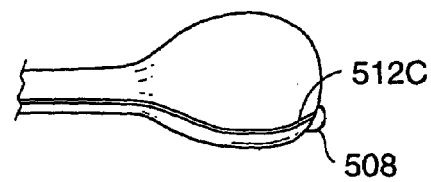
FIG. 18B is a side elevational view of the alternative implementation of the dissection balloon of FIG. 16, when inflated, and with a window attached at its distal end.
Figure 18C:
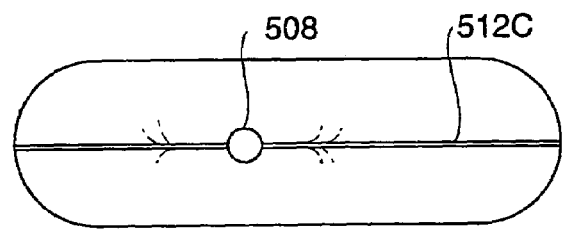
FIG. 18C is an end view of a preferred implementation of the dissection balloon of FIG. 16, when inflated, and with a window attached at its distal end.
Figure 18D:
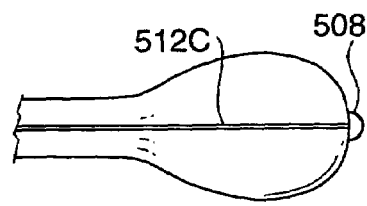
FIG. 18D is a side elevational view of the preferred implementation of the dissection balloon of FIG. 16, when inflated, and with a window attached at its distal end.

In an alternative embodiment, reinforcing sheet 513C is omitted, sheet 513A is made of thin, highly elastic material such as polyurethane or silicon coated latex (having high elasticity so that it stretches substantially during inflation) and sheet 513B is made of material (e.g., a multilayer film commercially available from Rexham comprising polyurethane and polyester layers) having low elasticity so that it does not stretch significantly during inflation. This alternative embodiment (with window 508 attached to its distal end), when inflated, has the appearance shown in FIGS. 18A and 18B, where FIG. 18A is an elevational view of the distal end of the inflated balloon and FIG. 18B is a side elevational view of the distal end of the inflated balloon. If both sheets 513A and 513B were inelastic, there would be relatively high localized stress (and wrinkles) at seam 512C when balloon 512 were inflated. By constructing balloon 512 from two sheets 513A and 513B having substantially different elasticities in accordance with the invention, puckering and wrinkling at seam 512C is reduced when balloon 512 is inflated, and the balloon's inflation characteristics can be tuned for desired results, including but not limited to increased lateral dissection, reduced incidence of epigastric (vein) stripping, and preferential, controlled dissection.

With reference to FIG. 16, distal end portion 512E of balloon 512 (opposite the neck 512A) is shaped to accept the end of an obturator or endoscope for control and manipulation of the balloon, and to receive a window 508 having a groove around a generally cylindrical side wall (best shown in FIGS. 10, 11, and 14).

A preferred technique for manufacturing balloon 512 of FIG. 16 is to bond together sheets 513A and 513B with a weld (indicated by the dashed line around the periphery of FIG. 16) of width X around the sheets' peripheries, and then to bond sheets 513A and 513C together with a weld of width X around their peripheries. Then, the weld is trimmed to a width Y (in FIG. 16), the trimmed weld's outer periphery is the solid line around the periphery of seam 512C. Then, end portion 512E is formed by cutting bonded sheets 513A and 513B along line 512F (shown in FIG. 16). The latter cut gives end portion 512E a cylindrical shape to which a suitable window 508 (made of rigid material) can be glued.

The width W of balloon 512 of FIG. 16 is longer than the length (the distance from line B—B to line 512F) of balloon 512, in order to increase the lateral extent of the tissue layers dissected by this balloon when it is inflated. In a typical implementation of balloon 512 of FIG. 16, width W is 6.8 inches, length L of sheet 513C is 5.875 inches, width Z of reinforcing sheet 513C is 0.82 inch, width X of the original (untrimmed) weld around the periphery of balloon 512 is 0.125 inch, and width Y of the trimmed weld around the periphery of balloon 512 is 0.06 inch.

Each of FIGS. 19, 20, and 21 is a side elevational view of a balloon window for attachment to the distal end of the inventive dissection balloon, as window 508 is attached to the distal end of balloon 512 of apparatus 600 of the embodiment of FIGS. 10–14. The window shown in each of FIGS. 19–21 is preferably composed of transparent, rigid material such as polished, clear polycarbonate or acrylic material. The window of each of FIGS. 19–21 (and window 508 of FIGS. 10 and 14) functions mechanically to separate tissue layers when pushed against the tissue layers by a rigid obturator (or a rigid endoscope such as endoscope 515' of FIG. 14 whose distal end 515A is pushed against window 508 as shown in FIG. 14). In alternative embodiments, the window of the inventive balloon is transparent and either rigid or non-rigid, but sufficiently strong to retain a desired optical shape while (and after) being pushed against tissue layers by a rigid obturator (or other rigid instrument) deployed within the dissection balloon.

The window of each of FIGS. 19–21 has a circular groove 508A around its generally cylindrical side wall, so that end portion 512E of dissection balloon 512 shown in FIG. 16 (or a corresponding end portion of alternative embodiment of the inventive dissection balloon) can be conveniently glued to groove 508A. Alternatively, it can be stepped or formed in another fashion with a surface conducive to gluing or mechanical fastening, and can have a hollow base for accepting the distal end of an endoscope or obturator (as does the window of FIGS. 21A and 21B to be discussed below).

The window of FIG. 19 is a wide angle lens, and each of its front surface 508B and its rear surface 508C (shown in phantom view in FIG. 19) has a curvature chosen to achieve desired wide angle lens optical properties.

The window of FIG. 20 is a lens (but not a magnifying lens), and each of its front surface 508D (having greater curvature than surface 508B of FIG. 19) and its rear surface 508C (shown in phantom view in FIG. 20) has a curvature chosen to achieve the desired lens optical properties.

The window of FIG. 21 is a magnifying lens, having a flat rear surface 508E (not a curved rear surface such as curved surface 508C of FIG. 20). Its front surface 508D has a curvature chosen to achieve the desired lens optical properties.

Figure 21A:
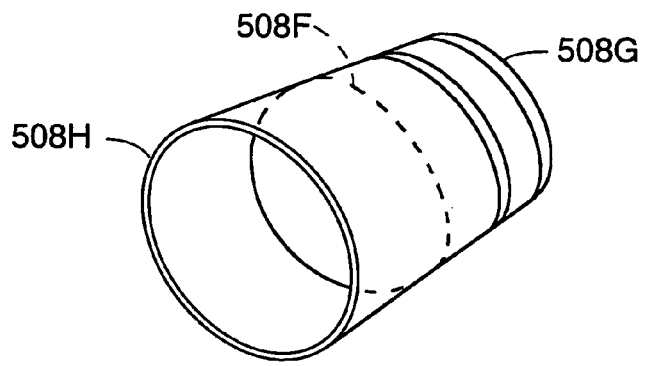
FIG. 21A is a perspective view of a fourth balloon window for use as window 508 of the FIG. 10 apparatus.
Figure 21B:
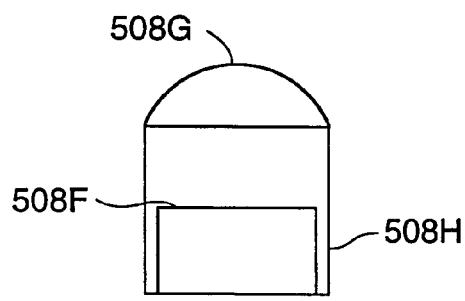
FIG. 21B is a side cross-sectional view of the window of FIG. 21A.

The window of FIGS. 21A and 21B is a lens, which has a flat rear optical surface 508F and a curved front optical surface 508G. Surface 508G has a curvature chosen to achieve the desired lens optical properties. The window of FIGS. 21A and 21B has a cylindrical skirt 508H which extends in the proximal direction (away from front surface 508G) from the periphery of surface 508F. Skirt 508H has multiple functions: to provide a surface conducive to gluing or mechanical fastening of a dissection balloon to the window; and (after the balloon has been attached to the window) to guide the distal end of an endoscope or obturator within the balloon into engagement with surface 508F and allow for positive control and manipulation of the balloon in response to movement of the endoscope or obturator (without tearing the balloon).

Figure 21C:
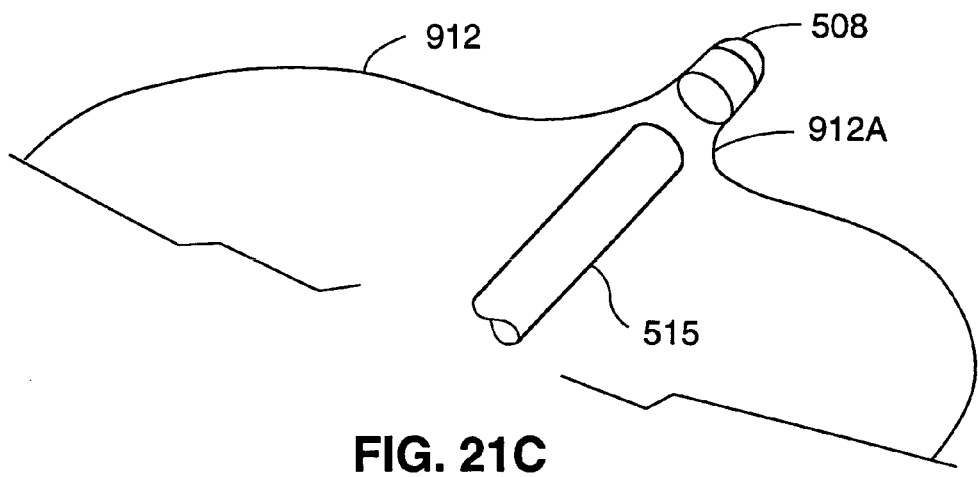
FIG. 21C is an embodiment of the inventive dissection balloon whose distal end portion is tapered to receive and capture an obturator (or endoscope).

As an alternative (or in addition) to employing a cup-shaped window (such as the skirted window of FIGS. 21A and 21B), the balloon itself is shaped so that when the window is attached to the balloon's distal end, the balloon defines a channel that guides the distal end of an endoscope or obturator within the balloon into engagement with the window. Such a channel also allows for positive control and manipulation of the balloon in response to movement of the endoscope or obturator (without tearing the balloon). An example of a dissection balloon having such a shape is dissection balloon 912 of FIG. 21C, whose distal end portion 912A is tapered to define a channel for receiving and capturing an obturator (or endoscope) 515. When obturator (or endoscope) 515 is moved, the force (e.g., frictional force) it exerts on distal end portion 912A allows for positive control and manipulation of balloon 912 in response to such movement.

The dissection balloon of the invention can have the alternative shape shown in FIG. 22. Dissection balloon 512' of FIG. 22 is identical to dissection balloon 512 of FIG. 16 except in that it has a circular cross-section (having radius R in the plane of FIG. 22 as shown) rather than an oblong cross-section (as does balloon 512 in the plane of FIG. 16). As shown in FIG. 22, balloon 512' includes rectangular neck reinforcing sheet 513C', but some alternative versions of balloon 512' do not include such a neck reinforcing sheet. The same materials can be used to manufacture balloon 512' (and each variation on balloon 512') as are used to manufacture each corresponding version of balloon 512. In a typical implementation of balloon 512' including neck reinforcing sheet 513C' as shown in FIG. 22, radius R is 2.125 inches, width Z of the neck reinforcing sheet is 0.82 inch, and length L of the neck reinforcing sheet is 5.875 inches.

It is within the scope of the invention to employ a dissection balloon (and/or an anchoring balloon) having nonuniform elasticity selected to achieve desired inflated shape and pressure characteristics. For example, dissection balloon 512 of FIG. 16 has been described in an embodiment comprising one sheet of relatively inelastic material bonded to another sheet of relatively elastic material (with or without a third sheet of material for reinforcing the balloon neck).

Figure 23:
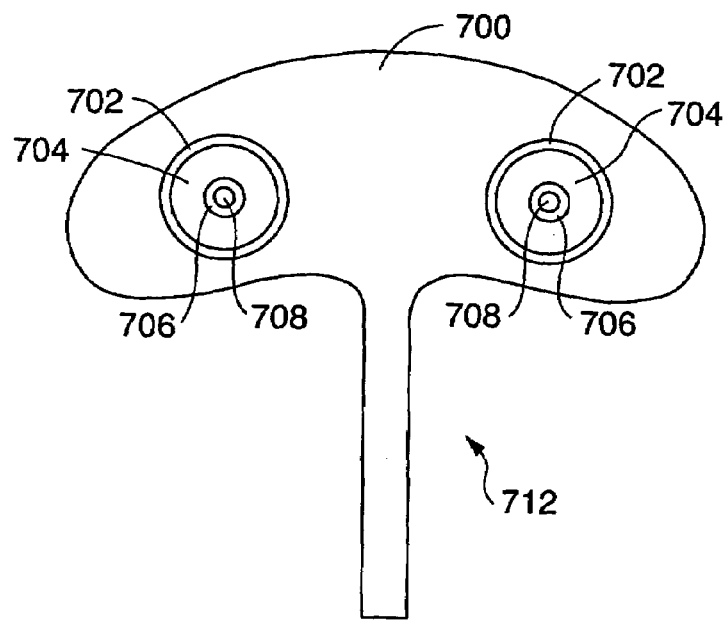
FIG. 23 is a plan view of another dissection balloon designed in accordance with the invention.

Numerous other implementations of dissection balloons (and/or anchoring balloons) having nonuniform elasticity are contemplated. For example, dissection balloon 712 of FIG. 23 has nonuniform elasticity selected to achieve desired inflated shape and pressure. Dissection balloon 712 includes a first large sheet 700 bonded (such as by RF-welding around the periphery of FIG. 23) to a second large sheet (identical to sheet 700 but not visible in FIG. 23). The two large sheets are made of material having low elasticity (preferably a multi-layer film-commercially available from Rexham comprising polyurethane and polyester layers, but alternatively a film of other material such as polyester). Two disk-shaped sheets 704 of material having high elasticity (preferably, polyurethane) are bonded to each large sheet. For example, two disk-shaped sheets 704 are bonded (such as by RF-welding) to sheet 700, each at annular weld region 702 as shown in FIG. 23. Each disk-shaped sheet 704 bonded to large sheet 700 is RF-welded to the corresponding disk-shaped sheet (the disk-shaped sheet below it, and thus not visible in FIG. 23) at annular weld region 708 shown in FIG. 23. Thus, when balloon 712 is inflated, its inelastic large sheets do not stretch significantly, but the elastic annular regions surrounding welds 708 do stretch significantly (and thus function as elastic baffles). As a result, balloon 712 has a very flat profile (in the sense that its inflated height in a direction perpendicular to the plane of FIG. 23 is very small relative to its maximum dimension in the plane of FIG. 23), it can be inflated to a greater pressure (when compared to a balloon made entirely of the inelastic material), and the stresses at its welds are more evenly distributed (when compared to a balloon made of two inelastic sheets bonded together at a single long weld).

Figure 24A:
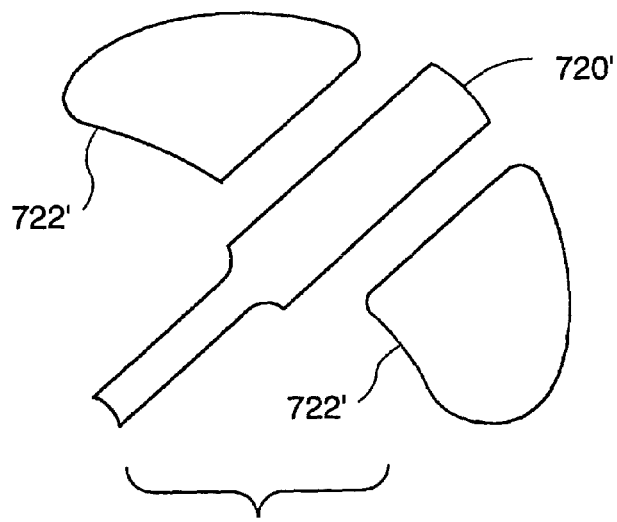
FIG. 24A is a plan view of three component sheets of yet another dissection balloon designed in accordance with the invention
Figure 24:
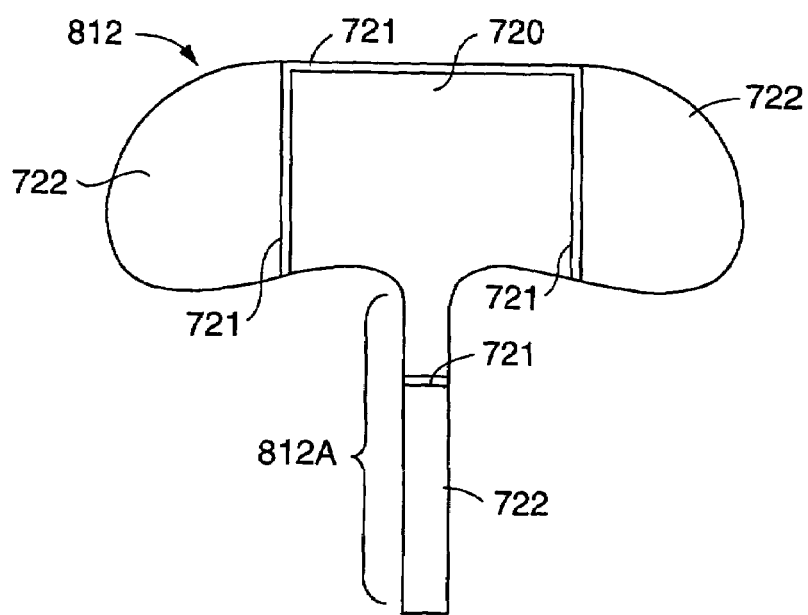
FIG. 24 is a plan view of yet another dissection balloon designed in accordance with the invention.

As another example, dissection balloon 812 of FIG. 24 has nonuniform elasticity selected to achieve desired inflated shape and pressure. Dissection balloon 812 consists of a first large sheet 722 bonded (such as by RF-welding around the periphery of FIG. 24) to a second large sheet (identical to sheet 722 but not visible in FIG. 24), and a reinforcing sheet bonded to the central portion of each large sheet. The two large sheets are made of material having high elasticity (preferably, polyurethane) having a first thickness. A reinforcing sheet 720 (which can be of the same material and can have the same thickness as sheet 722) is bonded to the central region of each large sheet (one such reinforcing sheet 720 is shown in FIG. 24 RF-welded to sheet 722 at weld regions 721). Unreinforced portions of sheet 722 are visible in FIG. 24 at neck portion 812A of balloon 812 and at the lateral end regions of balloon 812. Thus, in the FIG. 24 embodiment, at least part of neck portion 812A and the lateral end regions of balloon 812 have greater elasticity than the central portion to which sheet 720 is bonded. So, when balloon 812 is inflated, it has an hourglass profile (in the sense that its inflated lateral end portions stretch substantially more than its reinforced center portion). This structure is useful for certain tissue dissection applications where it is desired to increase the lateral extent of the tissue layers dissected.

In a variation on the FIG. 24 embodiment to be described with reference to FIG. 24A, the dissection balloon also has nonuniform elasticity selected to achieve desired inflated shape and pressure. This dissection balloon consists of a six sheets (three of which are shown in FIG. 24A, and the other three of which are identical to those shown in FIG. 24A). The six sheets are bonded together (such as by RF-welding). Four of the sheets are lateral end sheets 722' made of material having high elasticity (preferably, polyurethane). The two other sheets 720' are central sheets made of material having lower elasticity (or lower heat deflection temperature sensitivity) than sheets 722'. To construct the balloon, two end sheets 722' are bonded to the lateral edges of each central sheet 720' to make a composite sheet, one composite sheet is placed on the other (with the peripheries of the two composite sheets matched), and the two composite sheets are then bonded together around their matched peripheries.

In another variation on the FIG. 24 embodiment, a dissection balloon consists of two large sheets (having identical shape) bonded together at their peripheries, but at least one of the sheets (and preferably each of the sheets) has greater thickness (and hence lower elasticity) at its central portion and lesser thickness (and hence greater elasticity) at its lateral end portions. For example, each large sheet is made of polyurethane, its central portion has the same size and shape as does sheet 720 of FIG. 24 with 0.004 inch thickness, and its lateral end portions have 0.002 inch thickness.

In other embodiments, the desired nonuniform elasticity of the inventive balloon (either an anchoring balloon or a dissection balloon) is achieved by any one (or combinations of two or more) of the following:

1. at least one portion of the balloon is a sheet having a first thickness and at least one other portion is a sheet having a second thickness different than the first thickness;
2. at least one portion of the balloon is made of multilayer material comprising a first number of layers and at least one other portion is made of multilayer material comprising a second number of layers, where the second number is different than the first number (in such embodiments, all the layers typically have the same thickness, but alternatively some of the layers are thicker than others); and
3. the balloon is made of materials whose elasticity varies with temperature, and at least two different portions of the balloon are made of different materials with different heat deflection temperatures so that these portions have different elasticities (e.g., because the elasticity of each material depends on exposure to heat, and one portion of the balloon stretches more than another portion when both portions are subjected to the same temperature and pressure).

With reference again to FIGS. 10–14, the apparatus of FIGS. 10 and 14 is designed so that insufflation can be performed after obturator 515 (or endoscope 515'), the dissection balloon assembly (comprising balloon 512 and housing 513), and ring 514 have been removed from the anchoring and tissue retraction assembly (comprising elements 509, 503, 504, 505, and 517), and after valve 521 has been closed, balloon 517 has been inflated, and collar 504 and clamp 503 have been locked to anchor the tissue retraction assembly to the patient. After removal of obturator 515, ring 514, and the dissection balloon assembly, an endoscope (or other instrument) can be inserted through the end port of housing 509 (thereby displacing flapper valve 521), and through cannula 505 into the working space within the patient (in order to view the working space or perform some medical procedure therein). However, alternative embodiments of the invention enable such a viewing operation (or medical procedure) to be performed (unimpeded by the dissection balloon) in other ways.

Figure 25:
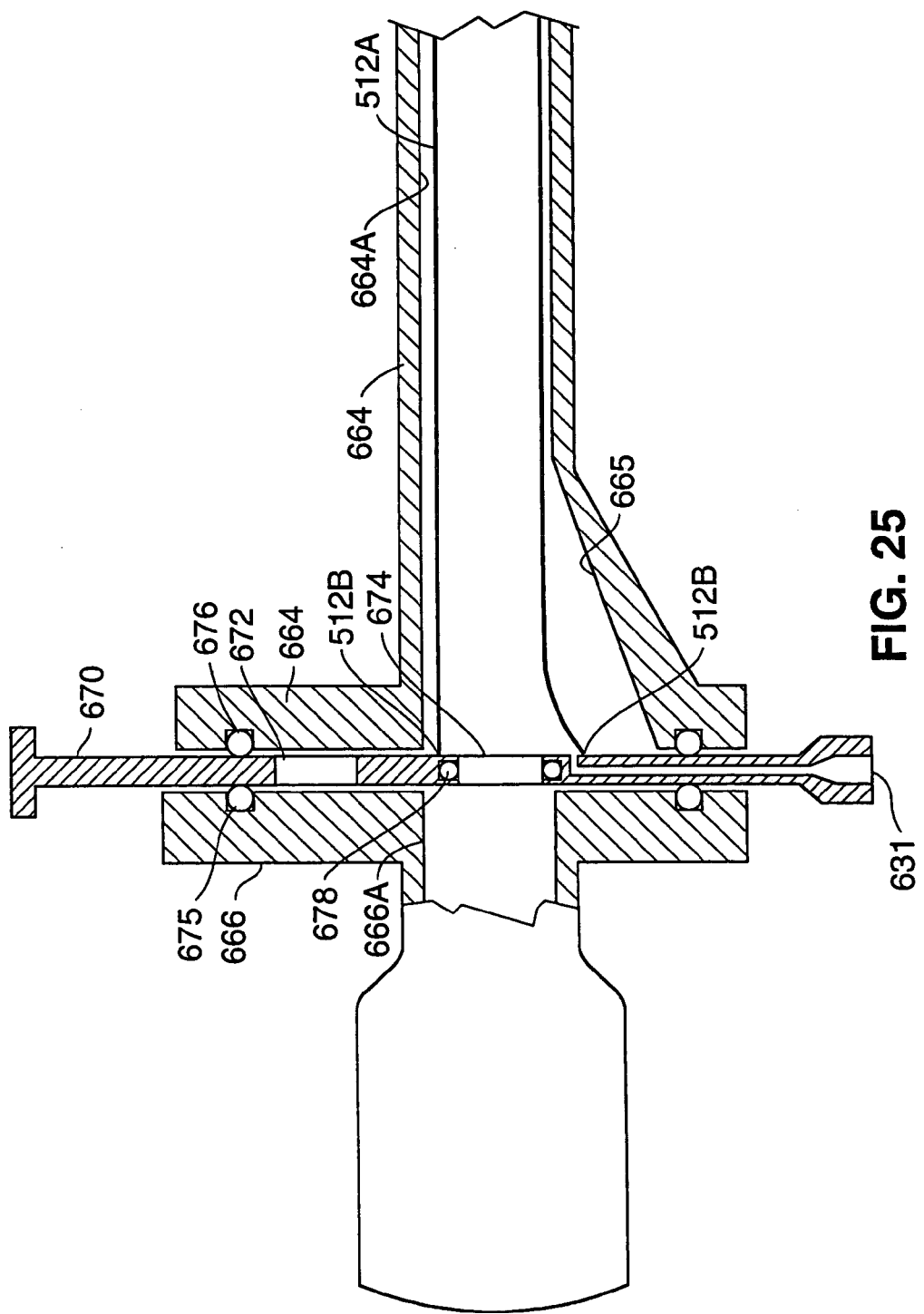
FIG. 25 is a partially side elevational, partially side cross-sectional view of a portion of an alternative embodiment of the inventive apparatus for tissue dissection and instrument anchoring.

For example, the FIG. 25 embodiment enables such a viewing operation (or medical procedure) to be performed in the following manner. The FIG. 25 embodiment is intended to replace the dissection balloon assembly of FIG. 11 (which comprises housing 513 and balloon 512). The FIG. 25 apparatus includes control lever 670 having two ports therethrough: cannula access port 672; and dissection balloon access port 674. Control lever 670 is slidably mounted between housing members 666 and 664. Mouth 512B of dissection balloon 512 is attached around the circular rim of port 674, and balloon 512 is pulled through central channel 664A through member 664 so that elongated neck 512A of balloon 512 extends through channel 664A as shown in FIG. 25. Thus, when lever 670 is moved to its upper position (shown in FIG. 25), with port 674 aligned with channel 664, an endoscope (or obturator) can be inserted through central channel 666A of member 666, through port 674, into the interior of balloon 512 (such as during a tissue dissection and tunneling operation).

To inflate the dissection balloon with the endoscope or obturator in place as described, inflation gas is pumped through port 631 (i.e., through an opened valve, not shown, in port 631) into mouth 512B of the balloon. O-ring seal 675 between lever 670 and member 666, and O-ring seal 676 between lever 670 and member 664, prevent the inflation gas from escaping out from between members 664 and 666. O-ring seal 678 mounted to lever 670 around port 674 is compressed against the endoscope, thus preventing the inflation gas from escaping out through channel 666A around the endoscope. Thus, a tunneling operation can be viewed using the endoscope (with imaging light entering the endoscope through a window such as window 508 mounted at the distal end of balloon 512).

To implement a viewing operation or medical procedure (in a manner unimpeded by dissection balloon 512, such as where it is not desired to view through a window mounted at the balloon's distal end), balloon 512 is deflated (the inflation gas escapes out through the opened valve in port 631), the endoscope or obturator is removed from within balloon 512 and port 674, and lever 670 is then pushed down to align port 672 with aligned channels 664A and 666A. This translation of lever 670 causes lever 670 to move mouth 512B of the balloon downward, so that the portion of balloon neck 512A adjacent to mouth 512B moves against tapered section 665 of member 664, away from the aligned longitudinal axes of channels 664A and 666A. In this configuration, an endoscope (or other instrument) can be inserted though central channel 666A of member 666, through port 672, and through channel 664 (but not into the interior of balloon 512) into the working space within the patient (to enable viewing of the working space, or performance of a medical procedure therein, in a manner unobstructed by the dissection balloon).

As an alternative to implementing the FIG. 25 embodiment (but with use of a long-necked dissection balloon deployed through a cannula such as cannula 505 of FIG. 10, with a rigid window such as window 508 of FIG. 10 attached to the balloon's distal end), it may be desirable to attach the window to the distal end of the dissection balloon non-permanently, such as by a tether or hinge (e.g., a living hinge), rather than permanently (e.g., by glue). Then, at the end of tunneling using the inflated balloon, the balloon is deflated, the obturator or endoscope employed for tunneling is removed from within the balloon, the non-permanently attached window is moved away (e.g., rotated on its hinge, or pushed away but retained on a tether) from the longitudinal axis of the cannula. Then, a surgical instrument or endoscope can be inserted through the cannula into the working space within the patient in a manner unimpeded by the window but without removing the balloon from the cannula. Where the window is tethered, it can be pushed out the distal end of the cannula after tunneling (so as to dangle on the tether in the balloon or between the dissected tissue layers), or the tether can be pulled out through the proximal end of the cannula (to remove the tethered window from the working space within the patient).

Alternative embodiments of the invention employ an alternative means (other than that embodied in the dissection balloon assembly of FIG. 25 or that of FIG. 10) for mounting a long-necked dissection balloon so that the balloon can be deployed through a cannula during dissection, and then positioned (after dissection) so as not to impede or obstruct viewing of a working space or performance of a surgical procedure. For example, some embodiments employ a mechanism to disconnect the mouth of the deflated dissection balloon (after dissection) from a housing to which the balloon mouth is attached during dissection. With the balloon mouth so disconnected from the housing (but with the deflated balloon remaining in the working space), an endoscope or other instrument is inserted through the housing (without entering the mouth or interior of the balloon) and into a working space between the dissected tissue layers.

In other embodiments, the deflated dissection balloon is pulled out of the cannula (through the cannula's proximal end) after dissection. In one of these embodiments, the mouth of the dissection balloon is attached to a sliding element in a housing and the body of the balloon extends through a cannula attached to the housing. The balloon is introduced into a patient and inflated to perform tissue dissection. After dissection, the balloon is deflated, inverted, and pulled back through the cannula. The sliding element is then slid out of the way (e.g., away from the cannula's central longitudinal axis) and an endoscope or other instrument is inserted through the housing and the cannula (without entering the mouth or interior of the balloon) into a working space between the dissected tissue layers.

With reference to FIGS. 26–35, we next describe an embodiment of the inventive method for using an apparatus (such as that of FIGS. 10–14) having a long-necked dissection balloon deployed through a cannula and having a window at its distal end. For specificity, FIGS. 26–35 are described with reference to the embodiment of FIGS. 10–14 which includes dissection balloon 512, deployed through cannula 505, which has a rigid window 508 (which can be a lens) mounted at its distal end, and which also has an endoscope 515' deployed through cannula 505 and balloon 512 (with the distal end of the endoscope abutting window 508). For the purpose of illustration only, the method is described in the context of separating the peritoneum from the properitoneal fascia in the course of repairing a hernia. Variations on the described embodiment (and in the apparatus employed to perform it) are useful for performing other medical procedures throughout the body.

Figure 26:
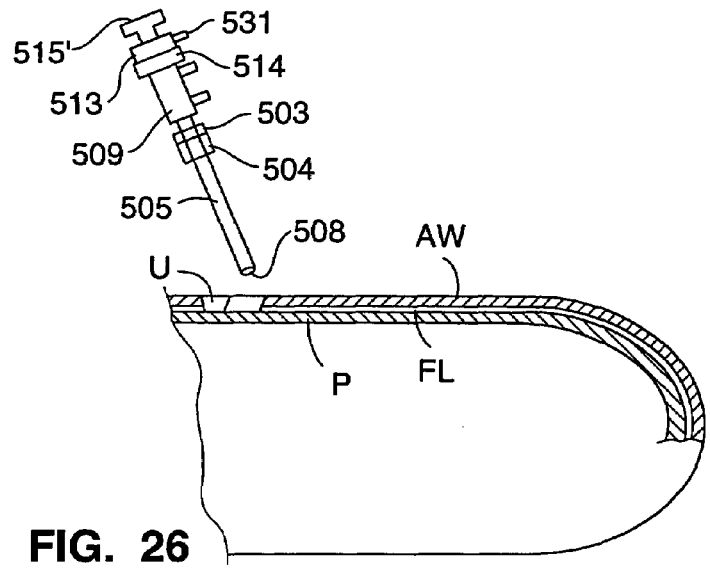
FIGS. 26–35 show a method of using the inventive apparatus (such as that of FIGS. 10–14) to separate the peritoneum from the overlying layer near the groin, with the apparatus inserted through an incision near the umbilicus.
Figure 27:
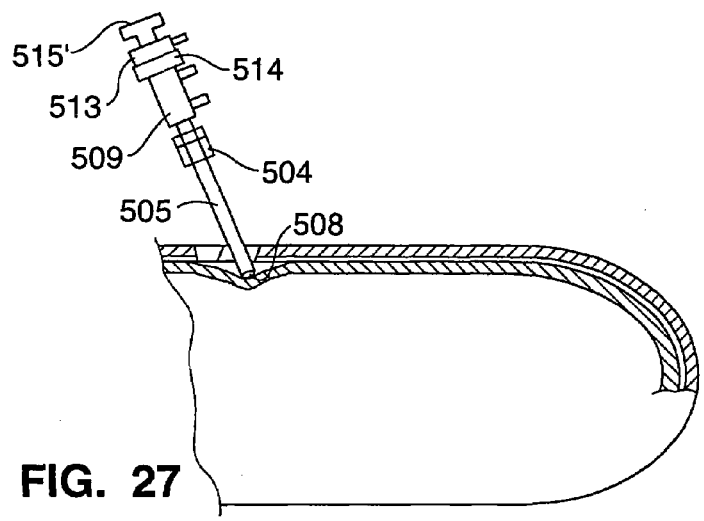

As shown in FIG. 26, an incision about 12–15 mm long is made in the abdominal wall AW, and is carried through the abdominal wall as far as, and including, the properitoneal fat layer FL. The incision is made at the umbilicus U. The distal end of the apparatus (i.e., window 508 and the distal portion of balloon 512 to which window 508 is attached) is lubricated and then inserted into the incision to bring the distal end into contact with the peritoneum. Additional gentle pressure is exerted on the proximal end of endoscope 515', which presses window 508 against the peritoneum, thereby detaching the part of the peritoneum in the immediate vicinity of the incision from the overlying layer (as shown in FIG. 27). In subsequent steps, the apparatus is advanced along the posterior surface of the peritoneum (toward the right in FIG. 26) until the distal end of the device is located at or near the groin.

Alternatively, in any of the dissection steps of the method, an obturator or other instrument (having substantially the same shape as endoscope 515') can be substituted for endoscope 515'. Such other instrument can be removed and replaced by an endoscope at any time to enable viewing of the space within the dissected tissue using the endoscope.

Figure 28:
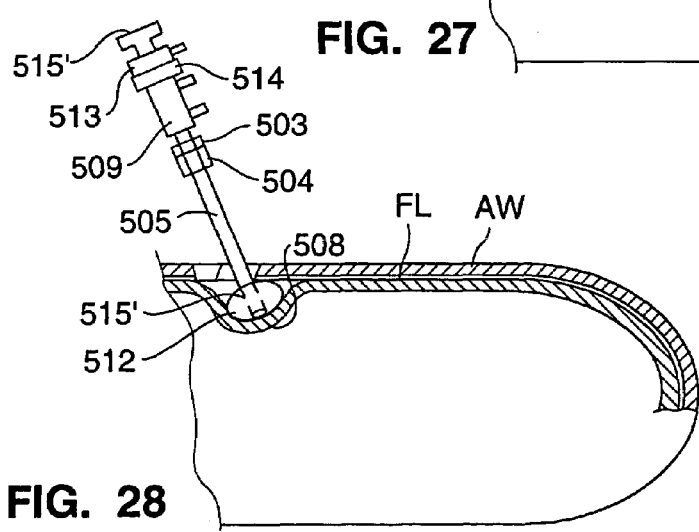

At any time, including during inflation of dissection balloon 512 and during advancement of window 508 between layers of tissue in the patient, the patient can be viewed by light that has propagated through window 508 into endoscope 515'. To inflate balloon 512, a source of a suitable inflation fluid (not shown, but as previously described), is connected to port 531 which protrudes from dissection balloon housing 513, and the flow of inflation fluid is turned to inflate dissection balloon 512 at least partially (as shown in FIG. 28). Balloon 512 expands between the peritoneum P and the properitoneal fat layer FL and progressively detaches an increasing area of the peritoneum from the overlying tissue over the entire dissection area. When using the preferred embodiment of the apparatus in which balloon 512 has an oval profile when expanded (in the sense that its expanded width is much greater than its expanded height), balloon 512 should be packed and the apparatus deployed so that expanded balloon 512's largest cross-sectional area is parallel to the tissue layers being dissected (the largest cross-sectional area should be oriented in a plane perpendicular to the plane of FIG. 28 to maximize the area of the tissue dissection while minimizing trauma to the patient).

Figure 29:
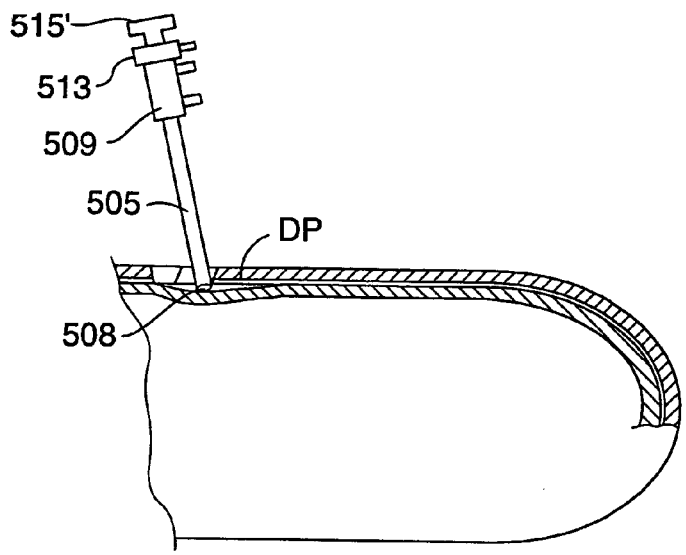
Figure 30:
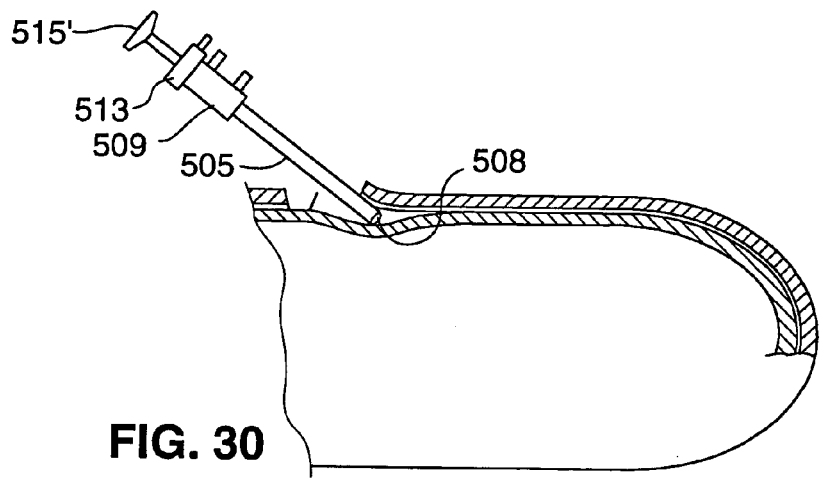

With reference to FIGS. 29–32, balloon 512 may be inflated and deflated a number of times, rather than just once, to dissect progressively the tissue layers. After inflating balloon 512 the first time (thereby partially dissecting the tissue layers), the inflation fluid in balloon 512 is vented and balloon 512 returns to its collapsed state, as shown in FIG. 29. The peritoneum DP that was separated by balloon 512 remains detached from the overlying layer. The apparatus, including collapsed dissection balloon 512, is then manipulated to advance the distal end (window 508) to the limit of detached peritoneum DP in the direction of the groin, as shown in FIG. 30. Endoscope 515' enables the position of the distal end relative to the detached part of the peritoneum to be observed.

Figure 31:
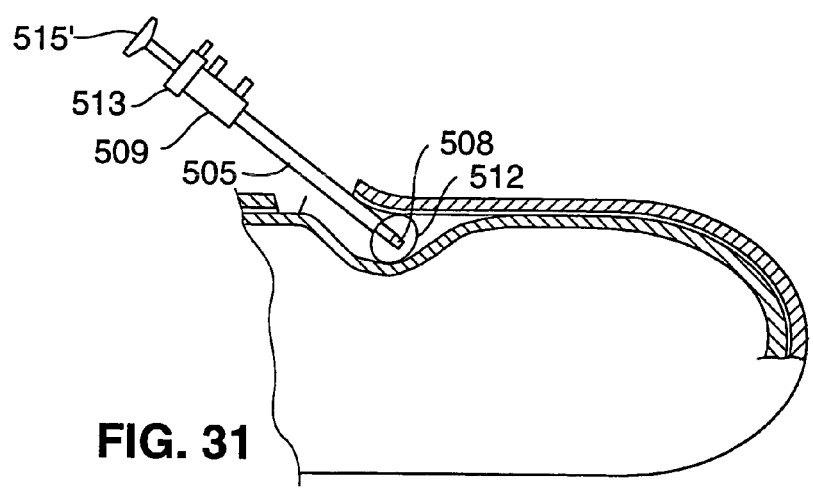
Figure 32:
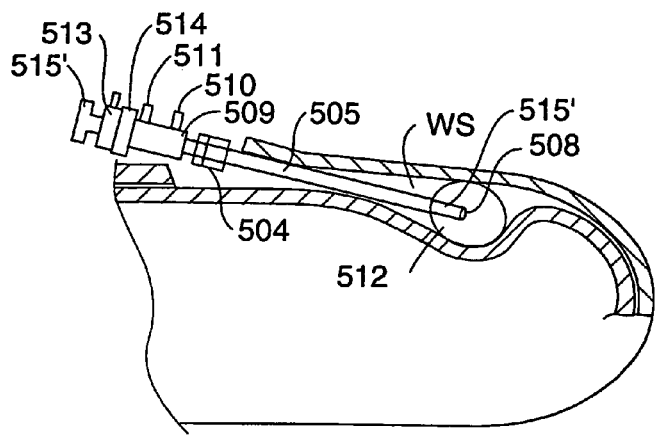
Figure 33:
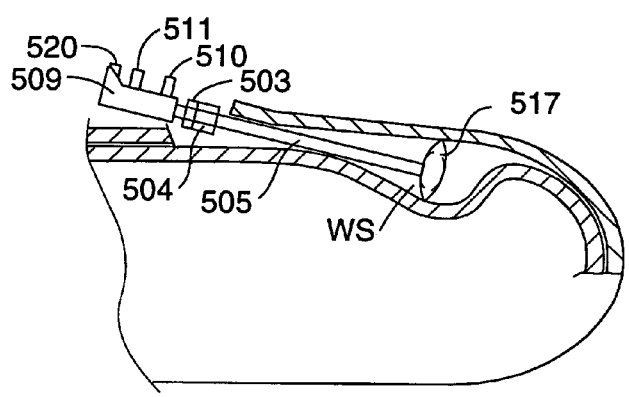

Balloon 512 is then inflated again thereby increasing the extent of the detached part of the peritoneum towards the groin, as shown in FIG. 31. The extent of the detached part of the peritoneum is increased in the direction from the umbilicus to the groin, but is not significantly increased in the direction transverse to this direction. Endoscope 515' is again used to observe the extent of the separation (in the manner described above).

The "tunneling" process of collapsing dissection balloon 512, advancing the distal end of the apparatus to the limit of the detached part of the peritoneum in the direction of the groin, holding the distal end in position, and re-inflating the dissection balloon, is repeated until the detached part of the peritoneum includes the site of the hernia. Care should be exercised to avoid dissecting tissue below the pubic bone, and to avoid forcing the dissection balloon downward into the deep pelvis in a manner that would cause trauma to the bladder.

Then, dissection balloon 512 is deflated (by removing endoscope 515' from the proximal end of the apparatus while ring 514 remains in place to hold the flapper valve within housing 509 open). Then, the dissection balloon assembly (comprising housing 513 and deflated balloon 512) and ring 514 are removed from the retraction and anchoring assembly of the apparatus, leaving the retraction and anchoring assembly shown in FIG. 33 (with the flapper valve within housing 509 closed as a result of removal of ring 514). Then, a suitable source of inflation fluid is attached to anchor balloon inflation valve 510, and anchor balloon 517 is inflated, leaving the retraction and anchoring assembly in the configuration shown in FIG. 33. When fully inflated, anchor balloon 517 should not be in direct contact with the bladder's surface.

Figure 34:
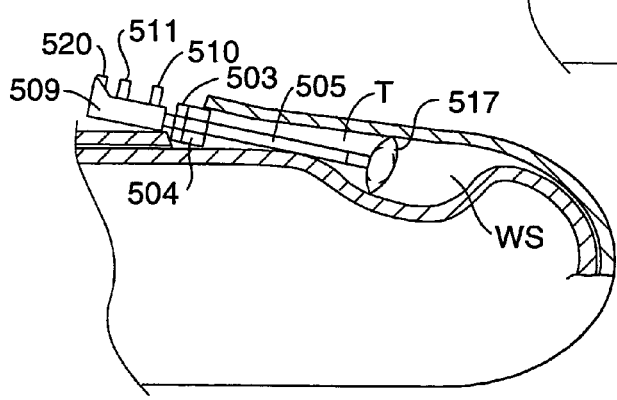

Then clamp 503 is advanced along cannula 505 toward the incision in the patient (preferably also, housing 509 is pulled back away from the incision in the patient), and clamp 503 is locked in a position along cannula 505 in which clamp 503 compresses foam collar 504 against the patient (as shown in FIG. 34). In this configuration, collar 504 helps to immobilize the anchoring and retraction assembly (including housing 509 and cannula 505) to the patient, and collar 504 applies a modest compressive force to the tissue between clamp 503 and inflated anchoring balloon 517, thereby helping balloon 517 form a seal to limit the escape of insufflation gas from working space WS within the patient out through tunnel T (between collar 504 and balloon 517 in the patient) during subsequent medical procedures. Inflated anchor balloon 517 itself preferably provides a substantially gas-tight seal with the entrance of the tunnel T. Of course, in alternative embodiments, anchor balloon 519 (described with reference to FIG. 15) is employed rather than anchor balloon 517 shown in various ones of FIGS. 26–35.

Figure 35:
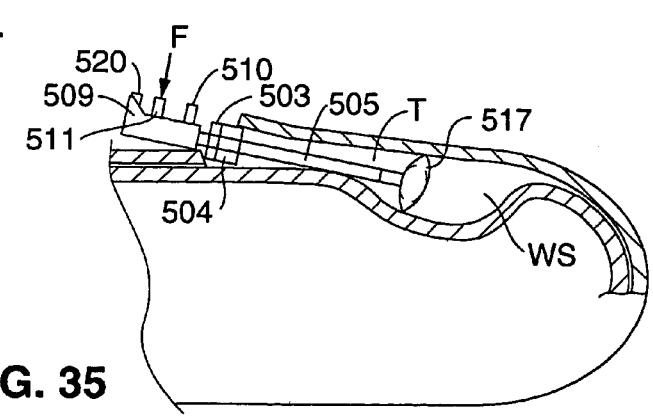

With reference to FIG. 35, the working space WS at the site of the hernia is then insufflated if necessary, by providing insufflation fluid (indicated by arrow F in FIG. 35) through valve 511 and cannula 505 into the working space WS. The hernia is then repaired using a known procedure. During such procedure, instruments can be removed from or inserted through the end port in housing 509 and cannula 505 (and/or instruments can be introduced into the working space through other incisions in the abdominal wall of the patient). At the end of the procedure, the extraperitoneal cavity can be quickly deflated by pressing button 511 to open the flapper valve within housing 509.

In other embodiments of the inventive method (also employing a long-necked dissection balloon deployed through a cannula), after dissection using the balloon, the balloon is deflated and retracted before a repair operation is performed in a working space between the dissected tissue layers. In alternative embodiments (also employing a long-necked dissection balloon deployed through a cannula), after dissection using the balloon, the balloon is deflated but retained in the patient during performance of a repair operation. In other embodiments employing a long-necked dissection balloon deployed through a cannula, where the balloon has lobes or other portions shaped so that instruments can be positioned between them, the balloon remains inflated in the patient after tissue is dissected using the balloon, instruments are then positioned between the dissected tissue layers without being obstructed by the inflated balloon (e.g., between lobes or other separated portions of the inflated balloon), and the instruments are manipulated to perform a repair operation.

Figure 36:
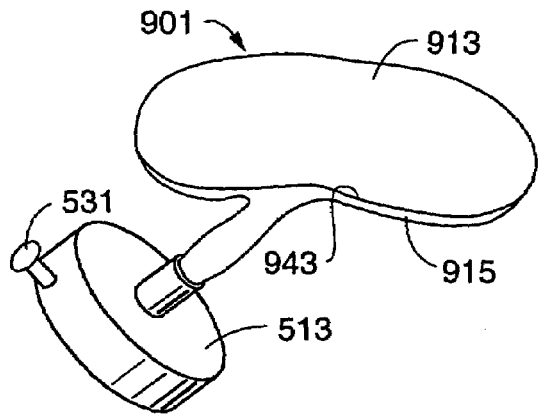
FIG. 36 is a perspective view of a balloon assembly for use in alternative embodiments of the invention.
Figure 37:
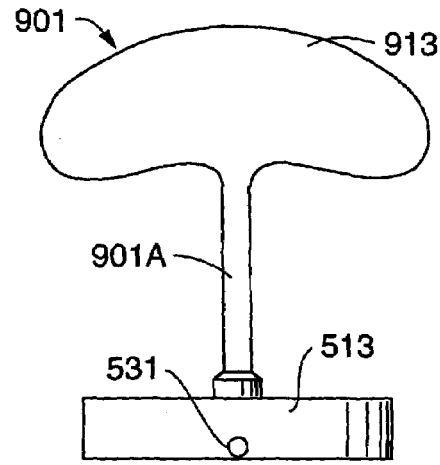
FIG. 37 is a plan view of the FIG. 36 assembly.

FIGS. 36 and 37 show a preferred dissection balloon 901 for use in the FIG. 10 apparatus (for dissecting the preperitoneal space) as a substitute for balloon 512 of FIG. 10. When inflated, balloon 901 has an oval profile, with an oblong cross-section (as shown in FIG. 37) in the plane containing its longest dimension. It is understood that the present invention may be practiced using a dissection balloon of any of a wide variety of shapes (suitable for deploying the balloon through a cannula) and that the shape of balloon 901 in FIG. 37 is merely an example. For example, balloon 901 may be spherical, flat, kidney-shaped, cylindrical, or may have any other shape suited for the particular dissection and/or retraction contemplated.

Balloon 901 is preferably mounted to housing 513 (of the type described with reference to FIGS. 11 and 12) as shown in FIGS. 36 and 37 but may alternatively be attached to any other housing. Elongated neck 901A of balloon 901 has a circular cross-section that can accommodate an endoscope.

As shown in FIG. 36, balloon 901 is formed from first sheet 913 and second sheet 915 (connected at seam 943) in a manner described above with reference to FIGS. 16–18. Balloon 901 is preferably made of the materials and fabricated in the manner described above in connection with FIGS. 16–24, and can be elastic, inelastic, or partially elastic and partially inelastic.

Figure 38:
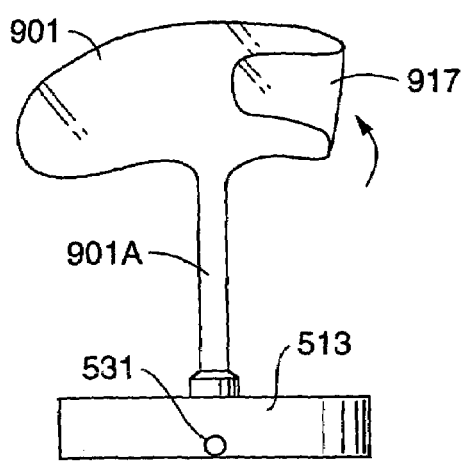
FIG. 38 is a plan view of the FIG. 36 assembly with a portion of the balloon displaced inwardly.

A preferred method of packing balloon 901 will be described with reference to FIGS. 38–42. As shown in FIG. 38, first lateral portion 917 of balloon 901 is initially displaced inwardly (i.e., pushed "inside-out" into the interior of the balloon). Although it is preferred to displace first portion 917 in a direction perpendicular to the longitudinal axis of the balloon's neck 901A, first portion 917 can alternatively be displaced inwardly in any other direction.

Figure 39:
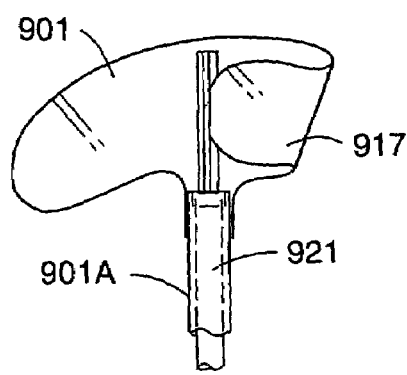
FIG. 39 shows the FIG. 38 assembly with a rolling device grasping an end of the first, inwardly-displaced balloon portion between two rods.
Figure 40:
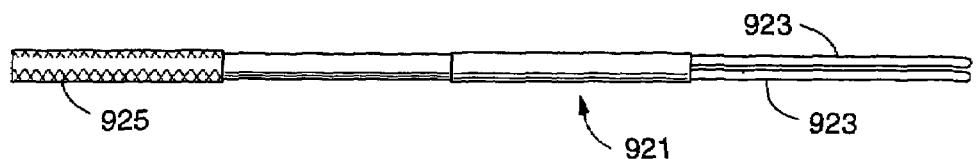
FIG. 40 is an elevational view of the rolling device of FIG. 39.

Inwardly-displaced portion 917 is then rolled up using a rolling device 921 inserted through neck 901A. Referring to FIGS. 39 and 40, rolling device 921 includes two rolling rods 923 for grasping first inwardly-displaced portion 917, when rods 923 are disposed in the interior of the balloon. Each rod 923 has a diameter of about ⅛ inch and rods 923 are separated by a gap of preferably less than 1/16 inch. The gap size and diameter of the rods 923 may vary, depending on the thickness of the balloon material. Furthermore, the rolling device 921 may include any other feature for grasping the inwardly displaced portion, such as a pair of jaws, a clamp or a pair of elastically deformable arms. The rolling device has a knurled handle 925 which is gripped to manipulate it.

Figure 41:
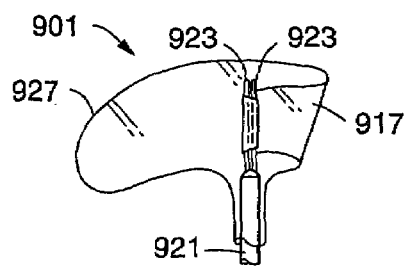
FIG. 41 shows the FIG. 39 assembly during rolling of the first balloon portion.
Figure 42:
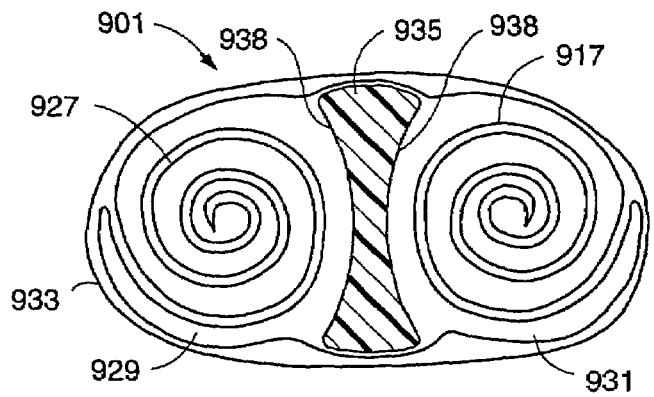
FIG. 42 is a cross-sectional view of the FIG. 36 assembly with first and second inwardly-displaced portions of the balloon rolled up into first and second rolls with an obturator positioned therebetween.

Rolling device 921 is rotated to roll the portion 917 as shown in FIG. 41 into a roll 931 (shown in FIG. 42). After portion 917 has been rolled into a sufficiently compact roll 931, second lateral portion 927 of balloon 901 (opposite first portion 917) is displaced inwardly and rolled in the same manner as portion 917 to form a roll 929 (shown in FIG. 42). An obturator (or endoscope) 935 is positioned through neck 901A of balloon 901 between rolls 929 and 931 to provide structural support for balloon 901 during insertion into the patient. Rolls 929, 931 are positioned on opposite sides of obturator (or endoscope) 935 with obturator (or endoscope) 935 preferably including concave portions 938 for receiving the rolls 929, 931. The two rolls 929, 931 (and the portion of element 935 between them) are then encased within sheath 933, which is similar or identical to sheath 506 described above in conjunction with the apparatus of FIGS. 10–14.

Figure 43:
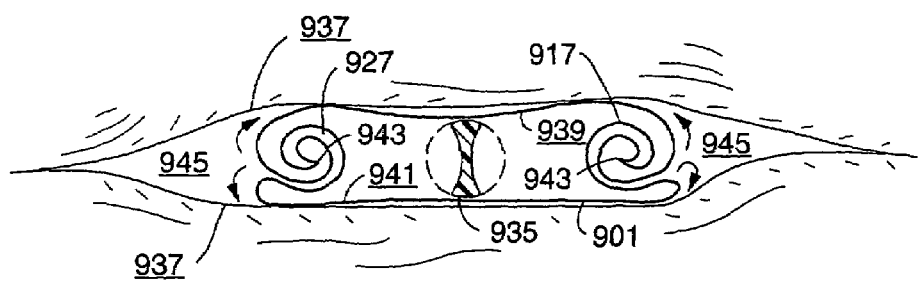
FIG. 43 shows the FIG. 42 assembly, deployed between tissue layers and partially inflated.

The compact, deflated, sheathed balloon 901 is introduced into the patient between two tissue layers to be separated and is then inflated. Balloon 901 may be used for dissecting and/or retracting tissue planes throughout the body. Referring to FIG. 43 which shows balloon 901 during inflation in the peritoneum, the inwardly-displaced portions evert during inflation so that differential motion between balloon 901 and adjacent tissue layers 937 is minimized thereby reducing trauma to the tissue layers.

Figure 44:
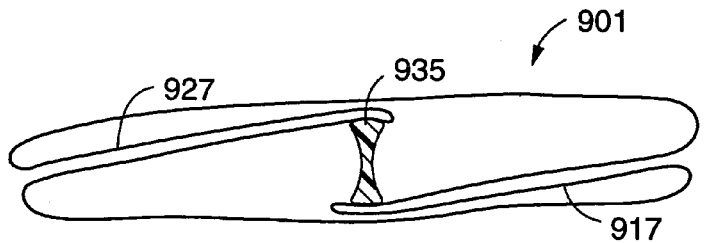
FIGS. 44 and 45 are cross-sectional views of the FIG. 36 assembly with the balloon in different stages of packing in accordance with an alternative method.
Figure 45:
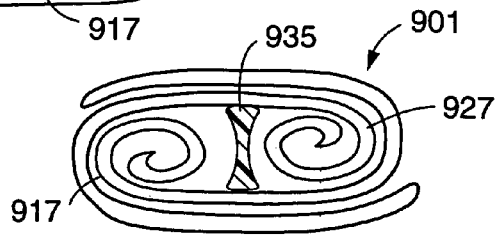

Although it is preferred to roll the first and second inwardly-displaced portions into first and second rolls 929, 931 within the interior of balloon 901 (after pushing these portions inside-out into the balloon's interior), balloon 901 may be packed in any other manner so long as an inwardly-displaced portion is provided which everts during inflation. For example, with reference to FIGS. 44 and 45, inwardly-displaced portions 917, 927 can be displaced to a side opposite the initial displacement and then rolled into rolls 929, 931 as previously described.

Figure 46:
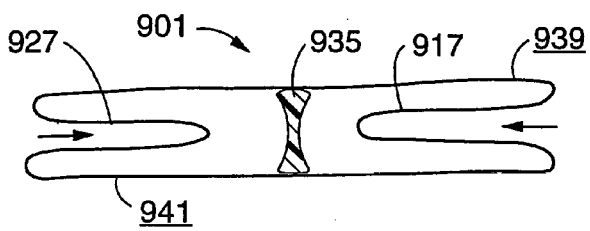
FIGS. 46 and 47 are cross-sectional views of the FIG. 36 assembly with the balloon in different stages of packing in accordance with another alternative method.
Figure 47:
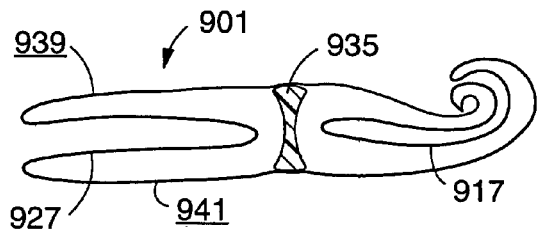

First and second inwardly-displaced portions 917, 927 can alternatively be rolled in a conventional manner from opposing lateral sides after portion 917, 927 have been displaced inward as shown in FIGS. 46 and 47. In this case, displaced first and second portions 917, 927 divide balloon 901 into an upper part 939 and a lower part 941. The upper part 939, first portion 917, and lower part 941 are then rolled up in a conventional manner as shown in FIG. 47. When balloon 901 is rolled in the manner shown in FIGS. 46–47, the balloon 901 will suffer the problem of relatively high differential motion between balloon 901 and the adjacent tissue layers during initial inflation and deployment, however, during the end of the inflation, the balloon will have relatively low differential motion relative to the tissue layers. This method of packing a balloon is useful when problematic internal structures are positioned laterally outward from the obturator. When the balloon is formed from first and second sheets 913, 915, the upper and lower parts 939, 941 are preferably formed by the first and second sheets, respectively. By configuring balloon 901 in this manner, the first and second portions include a part of seam 943 between the first and second sheets 913, 915. When coupling the first and second sheets 913, 915 together with an RF weld, seam 943 forms a relatively thin, rigid periphery which can cut or otherwise traumatize the tissue layers. Referring to FIG. 43, seam 943 everts into a space 945 between the tissue layers along the lateral edges of balloon 901 thereby minimizing contact between seam 943 and the tissue layers.

Figure 48:
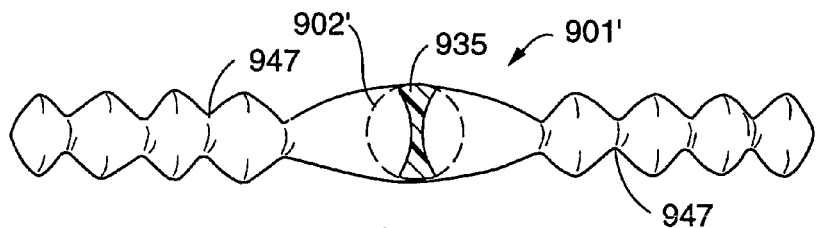
FIG. 48 is a cross-sectional view of a variation on the FIG. 36 assembly, with a balloon having accordion-folds.
Figure 49:
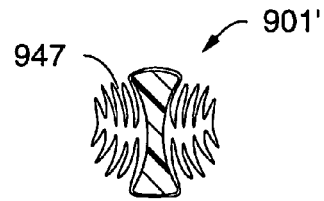
FIG. 49 is a cross-sectional view of the FIG. 48 assembly with the balloon having accordion-folds and packed in a compact state.

A balloon 901' having a number of inwardly-displaced portions in the form of accordion-folds 947 (when inflated) as shown in FIG. 48 can be employed in place of balloon 901 of FIGS. 36–37. FIG. 48 also shows obturator (or endoscope) 935 within balloon 901' (having been inserted through neck 902' of balloon 901'). FIG. 49 shows balloon 901' of FIG. 48 in a compact, deflated state.

Although preferred balloon packing techniques have been described, the invention can be practiced using other packing techniques or combinations of features of the described techniques. For example, a small roll may be formed in the manner shown in the FIGS. 39 and 41 followed by the procedure described with reference to FIG. 47.

Figure 50A:
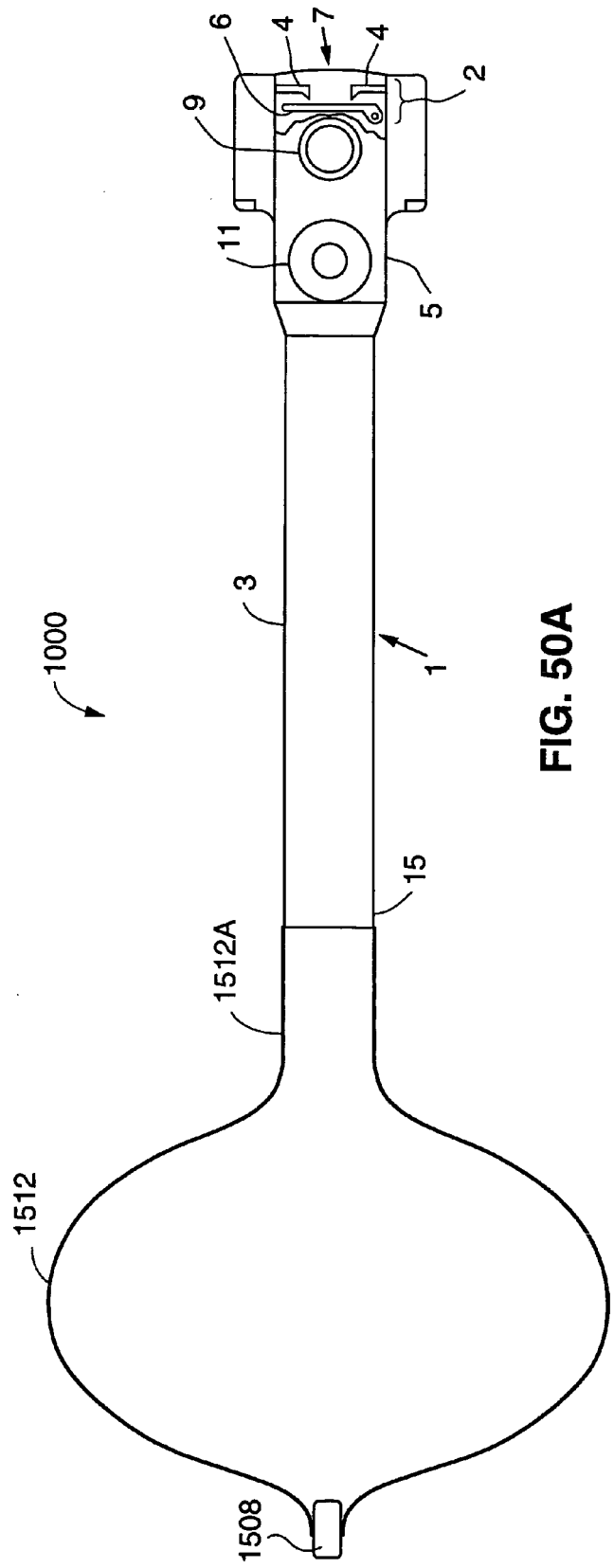
FIG. 50A is an alternative embodiment of a tissue dissection apparatus in which the dissection balloon is mounted to the distal end of a trocar. The dissection balloon is shown in an inflated condition.

FIG. 50A shows a simplified version of an apparatus 1000 according to the present invention. This apparatus 1000 comprises an introducer tube or trocar 1 which may be similar to the introducer tube 1 described in referenced application Ser. No. 07/911,714 and described herein with respect to FIGS. 1A–1B and 2A–2C. Trocar 1 includes a cannula 3 which has a rigid tube having a bore with a circular cross section that can accommodate an endoscope.

The proximal end of trocar 1 is preferably fitted with a port 5, in the proximal end 7 of which is mounted a flapper valve 2. Shutter 6 of flapper valve is operated by button 9. Seat 4 of the flapper valve additionally forms a gas-tight seal with an endoscope or other instrument inserted though the flapper valve into the bore of trocar 1. Port 5 is also fitted with a valve 11 to which a supply of a suitable inflation fluid can be connected. Naturally, trocar 1 may be provided with various other types of seals and ports without diverging from the scope of the present invention.

Attached to distal end 15 of the cannula 3 is a dissection balloon 1512 preferably having the materials, features, and construction of dissection balloon 512 of FIG. 10 (including any of the implementations of balloon 512 discussed above, such as those in which balloon 512 has nonuniform elasticity) but preferably having a shorter neck 1512A than balloon 512 (see elongate neck 512A of FIG. 11). Balloon 1512 can be attached to the distal end 15 of cannula 3 by stretching neck 1512A over the distal end of the trocar and held in place by friction resulting from the tension caused by stretching. A suitable adhesive, such as an epoxy or cyanoacrylate adhesive, may additionally or alternatively be used. Other means of attaching the balloon to the inside or the outside of the cannula can be used.

The balloon 1512 is preferably packed inside or around the distal end of an obturator and covered with a sheath prior to insertion of the balloon 1512 into the patient in a manner similar to that described with respect to the embodiment of FIG. 10 (see obturator 515 and sheath 506 described with respect to the embodiment of FIG. 10; an obturator may be inserted through cannula 3 in a similar manner). Once the trocar is positioned within the patient, an inflation medium is supplied to the balloon via the valve 11 in the trocar 1. An endoscope may be inserted into the balloon before inflation for observation through the lens, or during and/or after inflation for viewing through the balloon wall, to permit observation of balloon position and surrounding tissue.

The apparatus 1000 is simpler than the previously described embodiments in that it may be provided without a subassembly and anchor balloon 517 such as those shown in FIG. 13. Moreover, because the balloon 1512A is itself mounted on the trocar 1, rather than on a narrower tube such as the cannula 505 which during use is normally inserted into and withdrawn from the body through a trocar, balloon 1512 can be a larger and bulkier balloon than balloon 512 of FIGS. 10–12 will typically be.

Figure 50B:
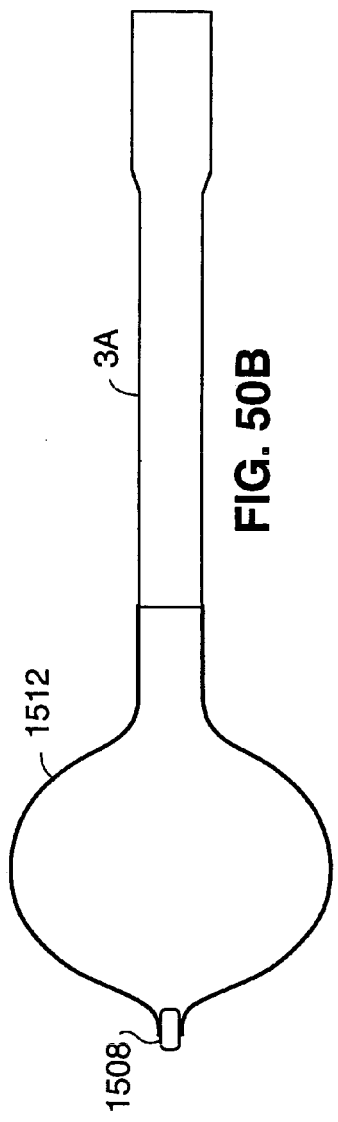
FIG. 50B is an alternative embodiment of a tissue dissection apparatus in which the dissection balloon is mounted to the distal end of a semi-rigid obturator. The dissection balloon is shown in an inflated condition.
Figure 50C:
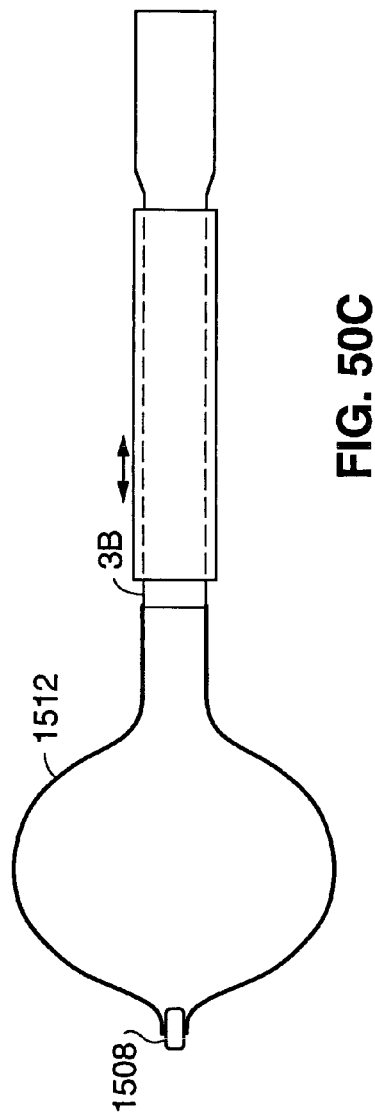
FIG. 50C is an alternative embodiment of a tissue dissection apparatus in which the dissection balloon is mounted to the distal end of a rigid obturator. The dissection balloon is shown in an inflated condition.

From this example it should be apparent that the balloons described herein may be delivered to an anatomical site within a patient by a variety of cannulas or other means in addition to those described with respect to the assembly of FIG. 10 and the trocar 1 of FIG. 50A. For example, a balloon of the type described herein may be attached to the distal end of a semi-rigid obturator (designated 3A in FIG. 50B) for insertion into a patient's body, or it may be attached to a flexible obturator (designated 3B in FIG. 50C) and contained within a rigid sheath 3C telescopically received over the flexible obturator 3B and slidably withdrawn from the balloon prior to inflation (FIG. 50C). As with the previously described embodiments, an obturator having a cannula to which the balloon 1512 is attached would preferably include a sealed port at its proximal end through which instruments and inflation fluid may be introduced for passage into the balloon. Moreover, although the balloon 1512 shown in FIGS. 50A–50C is of the type having a lens 1508 (which can be identical to above-described lens 508, or any of the above-described variations on lens 508), it should be appreciated that the configuration of FIG. 50A, 50B, or 50C can be used with any type of balloon, including those of various shapes and sizes, those formed of various materials, and those provided without viewing windows.

An alternative balloon packing technique is illustrated in FIGS. 51A–51D. This technique is one which allows the balloon to be packaged in a manner in which the overall length of the package is decreased. Such a technique may be desirable for a number of reasons.

For example, if a procedure is being carried out on a smaller patient using a dissecting balloon which is packaged in a manner which gives the packaged balloon substantial length, the distal end of the balloon may reach its destination within the body before essential features of the device (e.g., the anchor balloon 517 of FIG. 10) have passed into the fascia. Utilizing shorter balloons in such instances is not necessarily desirable because smaller balloons have less dissecting capacity than do larger balloons and thus may not provide effective dissection.

Packing the balloon to have a shortened packaged length is also advantageous in that it decreases the amount of packaging materials needed for the device and it thereby reduces packaging costs.

A new packing method according to the invention is one in which the overall packaged length of the device is shortened by packaging the device without including an obturator within the packaged device. Referring to FIG. 51A, as with several of the embodiments described above, dissection balloon 512 is provided attached to a distal portion of a flexible or rigid tube such as the cannula designated 3D (see, for example, trocar 1 of FIG. 50A, or obturators 3A and 3B of FIGS. 50B and 50C, respectively). The cannula 3D may be formed of a single piece of molded flexible polymer having a port 11A for delivering inflation fluid to the balloon and further having an integral self-sealing seal 2A. The seal 2A permits passage of instruments (such as obturator 515B shown in FIG. 51C) into the cannula and seals itself around such instruments to prevent loss of inflation pressure.

Although the balloon 512 shown in the drawings is of the type having a lens 508 as described above, it should be appreciated that this packing technique may be used for any type of balloon, including those of various shapes and sizes, those formed of various materials, and those provided without viewing windows.

To pack the balloon 512 according to the present embodiment, the balloon is flattened and then folded proximally against the cannula 3D to the orientation shown in FIG. 51A (top view) and 51B (side view), in a manner similar to that in which an umbrella closes around its shaft. Next, the balloon 512 is folded into a sheath such as sheath 506 described above with respect to the embodiment of FIG. 10.

This packing technique differs from the techniques previously described herein in that with those techniques the balloon is folded tightly against an obturator (such as obturator 515 of FIG. 11) inserted through the balloon. In such embodiments, if the obturator is removed prior to deployment of the balloon, a "tunnel" remains within the packaged balloon and a laparoscope may subsequently be inserted into the "tunnel" if desired. However, if the apparatus is packaged and shipped without the obturator in place, portions of the balloon will migrate into the tunnel during shipping and will therefore impede insertion of a laparoscope through the balloon prior to inflation.

When the balloon is folded over the flexible or rigid neck or cannula as described above, the neck maintains a tunnel through the folded and compressed balloon. This facilitates insertion of a laparoscope or other instrument (such as an obturator) through the tunnel and into the balloon to provide visualization and/or to provide stiffness which facilitates insertion of the balloon into the body cavity.

In the present embodiment, an obturator 515B may, but need not, be positioned within the cannula 3D during packing. Referring to FIG. 51C, when the apparatus is to be used for large patients an obturator 515B may be advanced through the cannula 3D to push the balloon 512 distally so as to increase the overall length of the apparatus. Doing so helps the balloon 512 to reach the desired depth within the patient for dissection.

It is contemplated that numerous modifications of and variations on the disclosed embodiments can be made without departing from the scope of the invention as defined by the following claims.

What is claimed is:

1. A device for dissecting tissue layers comprising:
    an elongate tubular member having a proximal end and a distal end defining a bore therein;
    an inflatable member including a neck, the inflatable member having an inflated and an uninflated state; and
    means for releasably attaching the inflatable member adjacent the distal end of the elongate tubular member including a circumferential groove defined in an inner wall of the distal end of the elongate tubular member that is adapted and configured for receiving the neck of the inflatable member and a cord disposed in the elongate tubular member, wherein a first end of the cord is attached to the neck of the inflatable member and a second end of the cord extends proximally for at least the length of the tubular member.

2. The device of claim 1, wherein the inflatable member in the uninflated state is configured and adapted to fit within the bore of the tubular member.

3. The device of claim 2, wherein the inflatable member in the uninflated state is further configured and adapted to be pulled proximally through the bore.

4. The device of claim 3, wherein the bore is dimensioned to receive a surgical instrument.

5. A device for dissecting tissue layers comprising:
    a tubular member having a proximal end and a distal end and defining a bore therein;
    a first inflatable member releasably attached adjacent the distal end of the tubular member and having inflated and uninflated states, the first inflatable member having a neck and being in fluid communication with the inner tube;
    a second inflatable member having inflated and uninflated states, the second inflatable member being disposed around an outer surface of the tubular member, wherein the second inflatable member is longitudinally spaced from the first inflatable member; and
    means for releasably attaching the first inflatable member to the distal end of the tubular member including a circumferential groove formed on an inner wall of the tubular member adjacent the open distal end of the tubular member that is adapted and configured for receiving the neck of the first inflatable member, and wherein the first inflatable member is releasably attached to the tubular member.

6. The device of claim 5, wherein the tubular member comprises a tube assembly having an open proximal end and an open distal end, the tube assembly further including an outer tube and an inner tube, the inner tube coaxially mounted inside the outer tube and defining a space, the space extending along at least a portion of the circumference of the outer tube and extending along at least a portion of the length of the outer tube.

7. The device of claim 6 wherein the second inflatable member forms a chamber and further comprising a radial passage communicating with the space, the radial passage communicating with the chamber of the second inflatable member.

8. The device of claim 6, further including a cord disposed in the inner tube, a first end of the cord being attached to the neck of balloon and a second end of the cord extends proximally for at least the length of the tube assembly.

9. The device of claim 6, wherein the first inflatable member in the uninflated state is configured and adapted to fit within the inner tube of the tube assembly.

10. The device of claim 9, wherein the first inflatable member in the uninflated state is further configured and adapted to be pulled proximally through the inner tube.

11. The device of claim 5, wherein the second inflatable member in the uninflated state is substantially flush with an outer surface of the tubular member and has a predetermined shape in the inflated state.

12. The device of claim 5 further comprising a cord disposed in the tubular member where a first end of the cord is attached to the neck of the first inflatable member and a second end of the cord extends proximally for at least the length of the tubular member.

13. The device of claim 12, wherein the bore of the tubular member is dimensioned to receive a surgical instrument.

14. A method of creating a working space in a patient comprising the steps of:
   making an incision in tissue of the patient;
   inserting a surgical device into the incision, the surgical device including
      a tubular member having a proximal end, a distal end and a bore therein, and
      first and second inflatable members where the first inflatable member is attached to the tubular member adjacent the distal end and the second inflatable member is disposed adjacent a distal end of the tubular member, the first and second inflatable members each having inflated and uninflated states;
   inflating the first inflatable member to separate layers of tissue within the patient to create the working space while the second inflatable member is in an uninflated state, wherein the first inflatable member is releasably attached to the tubular member; and
   deflating the first inflatable member and releasing the first inflatable member from the proximal end of the tubular member.

15. The method of claim 14, further comprising the steps of:
   advancing the surgical device into the incision; and
   inflating the second inflatable member.

16. The method of claim 15, further comprising the steps of:
   insufflating the working space; and
   inserting a surgical instrument into the working space through the bore of the tube assembly.

17. A method of creating a working space in a patient comprising the steps of:
   making an incision in tissue of the patient;
   inserting a surgical device into the incision, the surgical device including:
      a tubular member having a proximal end, a distal end and a bore therein, and
      first and second inflatable members where the first inflatable member is attached to the tubular member adjacent the distal end and the second inflatable member is disposed adjacent a distal end of the tubular member, the first and second inflatable members each having inflated and uninflated states;
   inflating the first inflatable member to separate layers of tissue within the patient to create the working space while the second inflatable member is in an uninflated state, wherein the first inflatable member is releasably attached to the tubular member; and
   removing the first inflatable member by pulling the first inflatable member through the bore of the tubular member such that the first inflatable member exits the proximal end of the tubular member.

18. A method of creating a working space in a patient comprising the steps of:
   making an incision in tissue of the patient;
   inserting a surgical device into the incision, the surgical device including:
      a tubular member having a proximal end, a distal end and a bore therein,
      first and second inflatable members where the first inflatable member is releasably attached to the tubular member adjacent the distal end and the second inflatable member is disposed adjacent a distal end of the tubular member, the first and second inflatable members each having inflated and uninflated states, and
      means for releasably attaching the first inflatable member to the tubular member, including a circumferential groove adjacent the distal end of the tubular member that is adapted and configured for receiving a neck of the first inflatable member and a cord;
   inflating the first inflatable member to separate layers of tissue within the patient to create the working space while the second inflatable member is in an uninflated state; and
   pulling the cord to release the first inflatable member and withdrawing the first inflatable member through the proximal end of the tubular member.

* * * * *